(12) United States Patent
Flower

(10) Patent No.: US 10,041,042 B2
(45) Date of Patent: Aug. 7, 2018

(54) METHODS FOR PRODUCTION AND USE OF SUBSTANCE-LOADED ERYTHROCYTES (S-IES) FOR OBSERVATION AND TREATMENT OF MICROVASCULAR HEMODYNAMICS

(71) Applicant: Novadaq Technologies ULC, Burnaby (CA)

(72) Inventor: Robert W. Flower, Hunt Valley, MD (US)

(73) Assignee: NOVADAQ TECHNOLOGIES ULC, Burnaby (CA)

( * ) Notice: Subject to any disclaimer, the term of this patent is extended or adjusted under 35 U.S.C. 154(b) by 0 days.

(21) Appl. No.: 14/177,050

(22) Filed: Feb. 10, 2014

(65) Prior Publication Data

US 2014/0308656 A1 Oct. 16, 2014

Related U.S. Application Data

(63) Continuation of application No. 12/917,849, filed on Nov. 2, 2010, now abandoned, which is a continuation-in-part of application No. PCT/US2009/042606, filed on May 1, 2009.

(60) Provisional application No. 61/126,344, filed on May 2, 2008.

(51) Int. Cl.
  *C12N 5/078* (2010.01)
  *A61K 9/50* (2006.01)
  *A61K 49/00* (2006.01)

(52) U.S. Cl.
  CPC .......... *C12N 5/0641* (2013.01); *A61K 9/5063* (2013.01); *A61K 49/0034* (2013.01); *A61K 49/0097* (2013.01)

(58) Field of Classification Search
  CPC .............. A61K 9/5063; A61K 49/0034; A61K 49/0097; C12N 5/0641
  See application file for complete search history.

(56) References Cited

U.S. PATENT DOCUMENTS

| | | |
|---|---|---|
| 4,109,647 A | 8/1978 | Stern et al. |
| 4,162,405 A | 7/1979 | Chance et al. |
| 4,200,801 A | 4/1980 | Schuresko |
| 4,263,916 A | 4/1981 | Brooks et al. |
| 4,394,199 A | 7/1983 | Barnhard, IV et al. |
| 4,473,841 A | 9/1984 | Murakoshi et al. |
| 4,532,918 A | 8/1985 | Wheeler |
| 4,541,438 A | 9/1985 | Parker et al. |
| 4,556,057 A | 12/1985 | Hiruma et al. |
| 4,619,249 A | 10/1986 | Landry |
| 4,718,417 A | 1/1988 | Kittrell et al. |
| 4,719,508 A | 1/1988 | Sasaki et al. |
| 4,768,513 A | 9/1988 | Suzuki |
| 4,773,097 A | 9/1988 | Suzaki et al. |
| 4,774,568 A | 9/1988 | Matsuo |
| 4,786,813 A | 11/1988 | Svanberg et al. |
| 4,805,597 A | 2/1989 | Iwakoshi |
| 4,815,848 A | 3/1989 | Hadeishi |
| 4,821,117 A | 4/1989 | Sekiguchi |
| 4,827,908 A | 5/1989 | Matsuo |
| 4,852,579 A | 8/1989 | Gilstad et al. |
| 4,858,001 A | 8/1989 | Milbank et al. |
| 4,860,731 A | 8/1989 | Matsuura |
| 4,867,137 A | 9/1989 | Takahashi |
| 4,868,647 A | 9/1989 | Uehara et al. |
| 4,900,934 A | 2/1990 | Peeters et al. |
| 4,930,516 A | 6/1990 | Alfano et al. |
| 4,938,205 A | 6/1990 | Nudelman |
| 4,957,114 A | 9/1990 | Zeng et al. |
| 4,993,404 A | 2/1991 | Lane |
| 4,995,396 A | 2/1991 | Inaba et al. |
| 4,995,398 A | 2/1991 | Turnidge |
| 4,998,972 A | 3/1991 | Chin et al. |
| 5,003,977 A | 4/1991 | Suzuki et al. |
| 5,042,494 A | 8/1991 | Alfano |
| 5,071,417 A | 12/1991 | Sinofsky |
| 5,078,150 A | 1/1992 | Hara et al. |
| 5,090,400 A | 2/1992 | Saito |
| 5,091,652 A | 2/1992 | Mathies et al. |
| 5,115,137 A | 5/1992 | Andersson-Engels et al. |

(Continued)

FOREIGN PATENT DOCUMENTS

| | | |
|---|---|---|
| AT | 409451 B | 8/2002 |
| CA | 2212257 A1 | 8/1996 |

(Continued)

OTHER PUBLICATIONS

Liu Q.P. et al., "Bacterial glycosidases for the production of universal red blood cells" Nature Biotechnology, Apr. 2007, vol. 25, No. 7, pp. 454-464.*
Perez M.T. et al., "In Vivo Studies on Mouse Erythrocytes Linked to Transferrin", IUBMB Life, 2002, vol. 54, pp. 115-121.*
Satpathy G.R. et al., "Loading red blood cells with trehalose: a step towards biostabilization", Cryobiology, 2004, vol. 49, pp. 123-136.*
Daniels G. et al., "Towards universal red blood cell", News and Views, Nature Biotechnology, Apr. 2007, vol. 25, No. 7, pp. 427-428.*
Batliwala H. et al., Methane-induced haemolysis of human erythrocytes, Biochemical Journal, 1995, vol. 307, pp. 433-438.*
Magnani M. et al., "Erythrocyte engineering for drug delivery and targeting", Biotechnol. Appl. Biochem., 1998, vol. 28, pp. 1-6. (Year: 1998).*
Jun. 11, 2014 European Office Action issued in application No. 13178642.8.

(Continued)

*Primary Examiner* — Satyendra K Singh
(74) *Attorney, Agent, or Firm* — Morrison & Foerster LLP

(57) ABSTRACT

Disclosed herein are methods, kits, and compositions for medical imaging relating to fluorescent dyes entrapped in erythrocytes. Also disclosed therein are methods, and compositions further comprising erythrocytes entrapping at least one therapeutically active agent, as well as methods for releasing the entrapped therapeutically active agent(s). Disclosed herein also are methods for preparation of the cells entrapping dye and therapeutically active agent(s) in a freeze-dried form that makes them readily available and easy to use in a clinical environment.

17 Claims, 18 Drawing Sheets

(56) References Cited

U.S. PATENT DOCUMENTS

| | | |
|---|---|---|
| 5,117,466 A | 5/1992 | Buican et al. |
| 5,125,404 A | 6/1992 | Kittrell et al. |
| 5,131,398 A | 7/1992 | Alfano et al. |
| 5,134,662 A | 7/1992 | Bacus et al. |
| 5,165,079 A | 11/1992 | Schulz-Hennig |
| 5,178,616 A | 1/1993 | Uemiya et al. |
| 5,196,928 A | 3/1993 | Karasawa et al. |
| 5,214,503 A | 5/1993 | Chiu et al. |
| 5,225,883 A | 7/1993 | Carter et al. |
| 5,255,087 A | 10/1993 | Nakamura et al. |
| 5,279,298 A | 1/1994 | Flower |
| 5,318,023 A | 6/1994 | Vari et al. |
| 5,318,024 A | 6/1994 | Kittrell et al. |
| 5,318,869 A | 6/1994 | Hashimoto et al. |
| 5,340,592 A | 8/1994 | Goodrich, Jr. et al. |
| 5,361,769 A | 11/1994 | Nilsson |
| 5,365,057 A | 11/1994 | Morley et al. |
| 5,371,355 A | 12/1994 | Wodecki |
| 5,375,603 A | 12/1994 | Feiler |
| 5,377,676 A | 1/1995 | Vari et al. |
| 5,377,686 A | 1/1995 | O'Rourke et al. |
| 5,394,199 A | 2/1995 | Flower |
| 5,419,323 A | 5/1995 | Kittrell et al. |
| 5,420,628 A | 5/1995 | Poulsen et al. |
| 5,421,337 A | 6/1995 | Richards-Kortum et al. |
| 5,421,339 A | 6/1995 | Ramanujam et al. |
| 5,424,841 A | 6/1995 | Van Gelder et al. |
| 5,430,476 A | 7/1995 | Hätele et al. |
| 5,437,274 A | 8/1995 | Khoobehi et al. |
| 5,438,989 A | 8/1995 | Hochman et al. |
| 5,453,448 A | 9/1995 | Narciso, Jr. |
| 5,465,718 A | 11/1995 | Hochman et al. |
| 5,496,369 A | 3/1996 | Howard, III |
| 5,507,287 A | 4/1996 | Palcic et al. |
| 5,514,127 A | 5/1996 | Shanks |
| 5,519,534 A | 5/1996 | Smith et al. |
| 5,576,013 A | 11/1996 | Williams et al. |
| 5,590,660 A | 1/1997 | MacAulay et al. |
| 5,623,930 A | 4/1997 | Wright et al. |
| 5,627,907 A | 5/1997 | Gur et al. |
| 5,647,368 A | 7/1997 | Zeng et al. |
| 5,656,498 A | 8/1997 | Iijima et al. |
| 5,662,644 A | 9/1997 | Swor |
| 5,664,574 A | 9/1997 | Chance |
| 5,673,701 A | 10/1997 | Chance |
| 5,689,241 A | 11/1997 | Clarke, Sr. et al. |
| 5,699,798 A | 12/1997 | Hochman et al. |
| 5,707,986 A | 1/1998 | Miller et al. |
| 5,732,707 A | 3/1998 | Widder et al. |
| 5,741,648 A | 4/1998 | Hemstreet, III et al. |
| 5,743,266 A | 4/1998 | Levene et al. |
| 5,756,541 A | 5/1998 | Strong et al. |
| 5,785,965 A | 7/1998 | Pratt et al. |
| 5,803,914 A | 9/1998 | Ryals et al. |
| 5,827,190 A | 10/1998 | Palcic et al. |
| 5,845,639 A | 12/1998 | Hochman et al. |
| 5,851,181 A | 12/1998 | Talmor |
| 5,865,754 A | 2/1999 | Sevick-Muraca et al. |
| 5,910,510 A | 6/1999 | Strong et al. |
| 5,919,616 A | 7/1999 | Aurelian et al. |
| 5,927,284 A | 7/1999 | Borst et al. |
| 5,935,942 A | 8/1999 | Zeimer |
| 5,951,980 A | 9/1999 | Collen |
| 5,956,435 A | 9/1999 | Buzug et al. |
| 5,965,356 A | 10/1999 | Aurelian et al. |
| 5,999,841 A | 12/1999 | Aoyagi et al. |
| 6,008,889 A | 12/1999 | Zeng et al. |
| 6,013,265 A | 1/2000 | Aurelian |
| 6,021,344 A | 2/2000 | Lui et al. |
| 6,032,070 A | 2/2000 | Flock et al. |
| 6,054,131 A | 4/2000 | Aurelian |
| 6,069,689 A | 5/2000 | Zeng et al. |
| 6,074,627 A | 6/2000 | Dean et al. |
| 6,081,612 A | 6/2000 | Gutkowicz-Krusin et al. |
| 6,093,149 A | 7/2000 | Guracar et al. |
| 6,122,042 A | 9/2000 | Wunderman et al. |
| 6,140,314 A | 10/2000 | Zeimer |
| 6,148,227 A | 11/2000 | Wagniéres et al. |
| 6,149,671 A | 11/2000 | Nordquist et al. |
| 6,162,242 A | 12/2000 | Peyman |
| 6,178,340 B1 | 1/2001 | Svetliza |
| 6,179,421 B1 | 1/2001 | Pang |
| 6,186,628 B1 | 2/2001 | Van de Velde |
| 6,196,226 B1 | 3/2001 | Hochman et al. |
| 6,207,168 B1 | 3/2001 | Aurelian |
| 6,211,953 B1 | 4/2001 | Niino et al. |
| 6,217,848 B1 | 4/2001 | Achilefu et al. |
| 6,223,069 B1 | 4/2001 | Pfeiffer et al. |
| 6,233,480 B1 | 5/2001 | Hochman et al. |
| 6,241,672 B1 | 6/2001 | Hochman et al. |
| 6,246,901 B1 | 6/2001 | Benaron |
| 6,248,727 B1 | 6/2001 | Zeimer |
| 6,263,227 B1 | 7/2001 | Boggett et al. |
| 6,272,374 B1 | 8/2001 | Flock et al. |
| 6,280,386 B1 | 8/2001 | Alfano et al. |
| 6,293,911 B1 | 9/2001 | Imasizumi et al. |
| 6,319,273 B1 | 11/2001 | Cheen et al. |
| 6,331,703 B1 | 12/2001 | Yarnall et al. |
| 6,335,429 B1 | 1/2002 | Cai et al. |
| 6,351,663 B1 | 2/2002 | Flower et al. |
| 6,351,667 B1 | 2/2002 | Godie |
| 6,353,750 B1 | 3/2002 | Kimura et al. |
| 6,399,354 B1 | 6/2002 | Knipe et al. |
| 6,440,950 B1 | 8/2002 | Zeimer |
| 6,443,976 B1 | 9/2002 | Flower et al. |
| 6,447,443 B1 | 9/2002 | Keogh et al. |
| 6,485,413 B1 | 11/2002 | Boppart et al. |
| 6,498,945 B1 | 12/2002 | Alfheim et al. |
| 6,544,183 B2 | 4/2003 | Thorn Leeson et al. |
| 6,566,641 B1 | 5/2003 | Suda |
| 6,603,552 B1 | 8/2003 | Cline et al. |
| 6,621,917 B1 | 9/2003 | Vilser |
| 6,631,286 B2 | 10/2003 | Pfeiffer et al. |
| 6,671,540 B1 | 12/2003 | Hochman |
| 6,757,554 B2 | 6/2004 | Rubinstein et al. |
| 6,804,549 B2 | 10/2004 | Hayashi |
| 6,821,946 B2 | 11/2004 | Goldspink et al. |
| 6,840,933 B1 | 1/2005 | Pang et al. |
| 6,853,857 B2 | 2/2005 | Pfeiffer et al. |
| 6,882,366 B1 | 4/2005 | Kijima et al. |
| 6,899,675 B2 | 5/2005 | Cline et al. |
| 6,915,154 B1 | 7/2005 | Docherty et al. |
| 6,936,043 B2 | 8/2005 | Peyman |
| 6,944,493 B2 | 9/2005 | Alam et al. |
| 7,113,817 B1 | 9/2006 | Winchester, Jr. et al. |
| 7,236,815 B2 | 6/2007 | Richards-Kortum et al. |
| 7,364,574 B2 | 4/2008 | Flower |
| 7,381,400 B2 | 6/2008 | Woltering |
| 7,400,753 B2 | 7/2008 | Seino et al. |
| 7,400,755 B2 | 7/2008 | West et al. |
| 7,482,318 B2 | 1/2009 | Aurelian et al. |
| 7,581,191 B2 | 8/2009 | Rice et al. |
| 7,881,777 B2 | 2/2011 | Docherty et al. |
| 7,885,438 B2 | 2/2011 | Uppaluri et al. |
| 8,036,437 B2 | 10/2011 | Arditi et al. |
| 8,073,224 B2 | 12/2011 | Strobel et al. |
| 8,144,958 B2 | 3/2012 | Nahm et al. |
| 8,185,176 B2 | 5/2012 | Mangat et al. |
| 8,194,981 B2 | 6/2012 | Suzuki |
| 8,285,353 B2 | 10/2012 | Choi et al. |
| 8,361,775 B2 | 1/2013 | Flower |
| 8,406,860 B2 | 3/2013 | Dvorsky et al. |
| 8,480,579 B2 | 7/2013 | Serov et al. |
| 8,521,260 B2 | 8/2013 | Grinvald et al. |
| 8,538,107 B2 | 9/2013 | Röttger |
| 8,647,605 B2 | 2/2014 | Mangat et al. |
| 8,892,190 B2 | 11/2014 | Docherty et al. |
| 8,929,974 B2 | 1/2015 | Hauger et al. |
| 8,965,488 B2 | 2/2015 | Dvorsky et al. |
| 9,129,366 B2 | 9/2015 | Nahm et al. |
| 9,351,644 B2 | 5/2016 | Nahm et al. |
| 9,357,931 B2 | 6/2016 | Nahm et al. |
| 9,421,280 B2 | 8/2016 | Mangat et al. |
| 9,610,021 B2 | 4/2017 | Dvorsky et al. |

(56) References Cited

U.S. PATENT DOCUMENTS

| | | |
|---|---|---|
| 2002/0025541 A1* | 2/2002 | Nelson et al. .................. 435/7.9 |
| 2002/0038120 A1 | 3/2002 | Duhaylongsod et al. |
| 2002/0099279 A1 | 7/2002 | Pfeiffer et al. |
| 2002/0099295 A1 | 7/2002 | Gil et al. |
| 2002/0146369 A1 | 10/2002 | Goldenberg |
| 2002/0181752 A1 | 12/2002 | Wallo et al. |
| 2002/0183621 A1 | 12/2002 | Pfeiffer et al. |
| 2003/0032885 A1 | 2/2003 | Rubinstein et al. |
| 2003/0050543 A1 | 3/2003 | Hartmann |
| 2003/0060718 A1 | 3/2003 | Alam et al. |
| 2003/0060722 A1 | 3/2003 | Pfeiffer et al. |
| 2003/0064025 A1 | 4/2003 | Yang et al. |
| 2003/0093064 A1 | 5/2003 | Peyman |
| 2003/0093065 A1 | 5/2003 | Peyman |
| 2003/0156252 A1 | 8/2003 | Morris et al. |
| 2003/0187349 A1 | 10/2003 | Kaneko et al. |
| 2003/0232016 A1 | 12/2003 | Heinrich |
| 2003/0236458 A1 | 12/2003 | Hochman |
| 2004/0066961 A1 | 4/2004 | Spreeuwers et al. |
| 2004/0077952 A1 | 4/2004 | Rafter et al. |
| 2004/0109231 A1 | 6/2004 | Haisch et al. |
| 2004/0156782 A1 | 8/2004 | Alam et al. |
| 2004/0162489 A1 | 8/2004 | Richards-Kortum et al. |
| 2004/0171827 A1 | 9/2004 | Peng et al. |
| 2004/0174495 A1 | 9/2004 | Levine |
| 2005/0019744 A1 | 1/2005 | Bertuglia |
| 2005/0020891 A1 | 1/2005 | Rubinstein et al. |
| 2005/0033145 A1 | 2/2005 | Graham et al. |
| 2005/0069525 A1 | 3/2005 | Mikael |
| 2005/0089866 A1 | 4/2005 | Hinuma et al. |
| 2005/0107380 A1 | 5/2005 | Nimmo et al. |
| 2005/0182321 A1 | 8/2005 | Frangioni |
| 2005/0182327 A1 | 8/2005 | Petty et al. |
| 2005/0182431 A1 | 8/2005 | Hausen et al. |
| 2005/0182434 A1 | 8/2005 | Docherty et al. |
| 2005/0187477 A1 | 8/2005 | Serov et al. |
| 2005/0197583 A1 | 9/2005 | Chance |
| 2005/0254008 A1 | 11/2005 | Ferguson et al. |
| 2006/0013768 A1 | 1/2006 | Woltering |
| 2006/0079750 A1 | 4/2006 | Fauci et al. |
| 2006/0108509 A1 | 5/2006 | Frangioni et al. |
| 2006/0118742 A1 | 6/2006 | Levenson et al. |
| 2006/0147897 A1 | 7/2006 | Grinvald et al. |
| 2006/0239921 A1 | 10/2006 | Mangat et al. |
| 2006/0241499 A1 | 10/2006 | Irion et al. |
| 2007/0122344 A1 | 5/2007 | Golijanin |
| 2007/0122345 A1 | 5/2007 | Golijanin |
| 2007/0203413 A1 | 8/2007 | Frangioni |
| 2007/0254276 A1 | 11/2007 | Deutsch et al. |
| 2008/0007733 A1 | 1/2008 | Marks et al. |
| 2008/0015446 A1 | 1/2008 | Mahmood et al. |
| 2008/0025918 A1 | 1/2008 | Frangioni et al. |
| 2008/0044073 A1 | 2/2008 | Bernhardt et al. |
| 2008/0161744 A1 | 7/2008 | Golijanin et al. |
| 2008/0221421 A1 | 9/2008 | Choi et al. |
| 2008/0221648 A1 | 9/2008 | Flower |
| 2008/0239070 A1 | 10/2008 | Westwick et al. |
| 2008/0319309 A1 | 12/2008 | Bredno et al. |
| 2009/0005693 A1 | 1/2009 | Brauner et al. |
| 2009/0042179 A1 | 2/2009 | Peltie et al. |
| 2009/0048516 A1 | 2/2009 | Yoshikawa et al. |
| 2009/0054788 A1 | 2/2009 | Hauger et al. |
| 2009/0118623 A1 | 5/2009 | Serov et al. |
| 2009/0137902 A1 | 5/2009 | Frangioni et al. |
| 2009/0252682 A1 | 10/2009 | Hillman |
| 2009/0297004 A1 | 12/2009 | Baumgart |
| 2010/0022898 A1 | 1/2010 | Rubinstein et al. |
| 2010/0036217 A1 | 2/2010 | Choi et al. |
| 2010/0061604 A1 | 3/2010 | Nahm et al. |
| 2010/0222673 A1 | 9/2010 | Mangat et al. |
| 2010/0286529 A1 | 11/2010 | Carroll et al. |
| 2011/0001061 A1 | 1/2011 | Ishihara |
| 2011/0013002 A1 | 1/2011 | Thompson et al. |
| 2011/0063427 A1 | 3/2011 | Fengler et al. |
| 2011/0071403 A1 | 3/2011 | Sevick-Muraca et al. |
| 2011/0098685 A1 | 4/2011 | Flower |
| 2011/0306877 A1 | 12/2011 | Dvorsky et al. |
| 2012/0026325 A1 | 2/2012 | Bunker et al. |
| 2012/0078093 A1 | 3/2012 | Flower |
| 2012/0165662 A1 | 6/2012 | Nahm et al. |
| 2013/0230866 A1 | 9/2013 | Miyashita et al. |
| 2013/0245456 A1 | 9/2013 | Ferguson, Jr. et al. |
| 2013/0286176 A1 | 10/2013 | Westwick et al. |
| 2013/0296715 A1 | 11/2013 | Lasser et al. |
| 2013/0345560 A1 | 12/2013 | Ferguson, Jr. et al. |
| 2014/0099007 A1 | 4/2014 | Sarkar et al. |
| 2014/0316262 A1 | 10/2014 | Havens |
| 2015/0112192 A1 | 4/2015 | Docherty et al. |
| 2015/0112193 A1 | 4/2015 | Docherty et al. |
| 2015/0196208 A1 | 7/2015 | Dvorsky et al. |
| 2015/0230710 A1 | 8/2015 | Nahm et al. |
| 2015/0230715 A1 | 8/2015 | Nahm et al. |
| 2016/0038027 A1 | 2/2016 | Brzozowski et al. |
| 2016/0110870 A1 | 4/2016 | Moriyama et al. |
| 2016/0199515 A1 | 7/2016 | Flower |
| 2016/0371834 A1 | 12/2016 | Watanabe et al. |
| 2017/0039710 A1 | 2/2017 | Minai et al. |
| 2017/0303800 A1 | 10/2017 | Flower et al. |
| 2018/0020933 A1 | 1/2018 | Dvorsky et al. |

FOREIGN PATENT DOCUMENTS

| | | |
|---|---|---|
| CA | 2413033 A1 | 3/2000 |
| CN | 1049781 A | 3/1991 |
| CN | 1200174 A | 11/1998 |
| CN | 1399528 A | 2/2003 |
| CN | 101264014 A | 9/2008 |
| DE | 3906860 A1 | 9/1989 |
| DE | 19608027 A1 | 9/1996 |
| DE | 10028233 A1 | 1/2002 |
| DE | 10120980 A1 | 11/2002 |
| DE | 69727220 T2 | 12/2004 |
| EP | 0091805 A2 | 10/1983 |
| EP | 0215772 A2 | 3/1987 |
| EP | 0512965 A1 | 11/1992 |
| EP | 0792618 A1 | 9/1997 |
| EP | 0826335 A1 | 3/1998 |
| EP | 1761171 | 3/2007 |
| EP | 1874181 | 1/2008 |
| GB | 2203831 A | 10/1988 |
| JP | S59-069721 A | 4/1984 |
| JP | S59-070903 A | 4/1984 |
| JP | S58-222331 A | 10/1988 |
| JP | H01-236879 A | 9/1989 |
| JP | 02-200237 A | 8/1990 |
| JP | H03-115958 A | 5/1991 |
| JP | 04-297236 A | 10/1992 |
| JP | H05-264232 A | 10/1993 |
| JP | H06-007353 A | 1/1994 |
| JP | 06-335451 A | 12/1994 |
| JP | 07-065154 A | 3/1995 |
| JP | 07-079955 A | 3/1995 |
| JP | H07-155285 A | 6/1995 |
| JP | H07-155286 A | 6/1995 |
| JP | H07-155290 A | 6/1995 |
| JP | H07-155291 A | 6/1995 |
| JP | H07-155292 A | 6/1995 |
| JP | 07-222712 A | 8/1995 |
| JP | H07-204156 A | 8/1995 |
| JP | H07-222723 A | 8/1995 |
| JP | H07-25812 A | 10/1995 |
| JP | H07-250804 A | 10/1995 |
| JP | 08-024227 A | 1/1996 |
| JP | H08-224208 A | 9/1996 |
| JP | H08-224209 A | 9/1996 |
| JP | H08-224240 A | 9/1996 |
| JP | H09-120033 A | 5/1997 |
| JP | H09-305845 A | 11/1997 |
| JP | H09-308609 A | 12/1997 |
| JP | H09-309845 A | 12/1997 |
| JP | H10-503480 A | 3/1998 |
| JP | H10-085222 A | 4/1998 |
| JP | H10-104070 A | 4/1998 |
| JP | H10-506440 A | 6/1998 |

(56) References Cited

FOREIGN PATENT DOCUMENTS

| | | |
|---|---|---|
| JP | H10-506550 A | 6/1998 |
| JP | H10-201700 A | 8/1998 |
| JP | H10-201707 A | 8/1998 |
| JP | H11-137517 A | 5/1999 |
| JP | H10-151104 A | 6/1999 |
| JP | H11-155812 A | 6/1999 |
| JP | H11-509748 A | 8/1999 |
| JP | 2002-219129 A | 8/2002 |
| JP | 2003-510121 A | 3/2003 |
| JP | 2003-144401 A | 5/2003 |
| JP | 2004-528917 A | 9/2004 |
| JP | 2006-503620 A | 2/2006 |
| JP | 2006-192280 A | 7/2006 |
| JP | 2007-021006 A | 2/2007 |
| JP | 3896176 B2 | 3/2007 |
| JP | 2008-525126 A | 7/2008 |
| JP | 2008-535600 A | 9/2008 |
| JP | 2008-231113 A | 10/2008 |
| JP | 2010-505582 A | 2/2010 |
| JP | 2011-509768 A | 3/2011 |
| JP | 2011-519589 A | 7/2011 |
| JP | 5918532 B2 | 5/2016 |
| KR | 90-0005434 B1 | 7/1990 |
| KR | 2002-0064287 A | 8/2002 |
| RU | 2288633 C1 | 12/2006 |
| WO | WO-1986/02730 A1 | 5/1986 |
| WO | WO-1990/10219 A1 | 9/1990 |
| WO | WO-1990/12536 A1 | 11/1990 |
| WO | WO-1993/25141 A1 | 12/1993 |
| WO | WO-1994/12092 A1 | 6/1994 |
| WO | WO-1995/00171 A1 | 1/1995 |
| WO | WO-1995/26673 A2 | 10/1995 |
| WO | WO-1996/09435 A1 | 3/1996 |
| WO | WO-1996/09792 A1 | 4/1996 |
| WO | WO-1996/18415 A1 | 6/1996 |
| WO | WO-1996/23524 A1 | 8/1996 |
| WO | WO-1996/39925 A1 | 12/1996 |
| WO | WO-1997/08538 A1 | 3/1997 |
| WO | WO-1998/24360 A1 | 6/1998 |
| WO | WO-1998/30144 A1 | 7/1998 |
| WO | WO-1998/46122 A1 | 10/1998 |
| WO | WO-1999/00053 A1 | 1/1999 |
| WO | WO-1999/47940 A1 | 9/1999 |
| WO | WO-1999/53832 A1 | 10/1999 |
| WO | WO-2000/42910 A1 | 7/2000 |
| WO | WO-2000/47107 A1 | 8/2000 |
| WO | WO-2001/08552 A1 | 2/2001 |
| WO | WO-2001/17561 A1 | 3/2001 |
| WO | WO-2001/22870 A1 | 4/2001 |
| WO | WO-2001/39764 A2 | 6/2001 |
| WO | WO-2001/69244 A2 | 9/2001 |
| WO | WO-2001/80734 A1 | 11/2001 |
| WO | WO-2001/82786 A2 | 11/2001 |
| WO | WO-2002/061390 A2 | 8/2002 |
| WO | WO-2003/006658 A1 | 1/2003 |
| WO | WO-2004/006963 A1 | 1/2004 |
| WO | WO-2004/052195 A1 | 6/2004 |
| WO | WO 2005026319 A2 * | 3/2005 ............... A01N 1/02 |
| WO | WO-2005/034747 A1 | 4/2005 |
| WO | WO-2005/079238 A2 | 9/2005 |
| WO | WO-2006/111836 A1 | 10/2006 |
| WO | WO-2006/111909 A1 | 10/2006 |
| WO | WO-2006/116634 A2 | 11/2006 |
| WO | WO-2006/119349 A1 | 11/2006 |
| WO | WO-2006/121631 A2 | 11/2006 |
| WO | WO-2006/121631 A3 | 11/2006 |
| WO | WO-2006/123742 A1 | 11/2006 |
| WO | WO-2007/028032 A2 | 3/2007 |
| WO | WO-2008/044822 A1 | 4/2008 |
| WO | WO-2008/070269 A2 | 6/2008 |
| WO | WO-2008/070269 A3 | 6/2008 |
| WO | WO-2008/087869 A1 | 7/2008 |
| WO | WO-2009/046985 A2 | 4/2009 |
| WO | WO-2009/046985 A3 | 4/2009 |
| WO | WO-2009/048660 A2 | 4/2009 |
| WO | WO-2009/092162 A1 | 7/2009 |
| WO | WO-2009/127972 A2 | 10/2009 |
| WO | WO-2012/038824 A1 | 3/2012 |
| WO | WO-2012/096878 A2 | 7/2012 |
| WO | WO-2013/190391 A2 | 12/2013 |

OTHER PUBLICATIONS

Database Biosis [online] Biosciences Information Service, Philadelphia, PA, US; 2005 Peiretti et al.: "Human erythrocyte-ghost-mediated choroidal angiography and photocoagulation." XP002725023, Database accession No. Prev200600056121 (abstract).
Gothoskar A.V., Resealed Erythrocytes: A Review, Pharmaceutical Technology, Mar. 2004, pp. 140, 142, 144, 146, 148, 150, 152 and 154-158.
Peiretti E. et al., Human Erythrocyte-Ghost-Mediated Choroidal Angiography and Photocoagulation, Invest. Ophthalmol. Vis. Sci., 2005, vol. 46, E-Abstract 4282-B640 (ARVO 2005 Meeting Abstract, pp. 1-2; accessed online ON Oct. 25, 2012 at the web http://abstracts.iovs.org/cgi/content/abstract/46/5/4282).
Alvarez, F.J. et al., "Behaviour of isolated rat and human red blood cells upon hypotonic-dialysis encapsulation of carbonic anhydrase and dextran", Biotechnology and Applied Biochemistry, 1996, vol. 23, No. 2, pp. 173-179.
Flower, R. W. et al., "Observation of erythrocyte dynamics in the retinal capillaries and choriocapillaris using ICG-loaded erythrocyte ghost cells", Annual Meeting of the Macula Society, Mar. 26, 2008-Mar. 29, 2008, Abstract.
Magnani, M. et al., "Targeting antiretroviral nucleoside analogues in phosphorylated form to macrophasges: in vitro and in vivo studies", Proceedings of the National Academy of Sciences in the USA, National Academy of Science, Washington, DC, US, vol. 89, Jul. 1, 1992, pp. 6477-6481.
Flower, Robert W., et al., "Observation of Erythrocyte Dynamics in the Retinal Capillaries and Choriocapillaris Using ICG-loaded Erythrocyte Ghost Cells", Investigative Ophthalmology & Visual Science, Associate for Research in Vision and Ophthalmology, US, vol. 49, No. 12, Dec. 1, 2008, pp. 5510-5516.
International Search Report of Corresponding Application No. PCT/US2009/042606 dated Sep. 11, 2009.
Akintunde, A. et al. (Oct.-Nov. 1992). "Quadruple Labeling of Brain-Stem Neurons: A Multiple Retrograde Fluorescent Tracer Study of Axonal Collateralization," *Journal of Neuroscience Methods* 45(1-2):15-22.
Alander, J.T. et al. (Jan. 1, 2012). "A Review of Indocyanine Green Fluorescent Imaging in Surgery," *International Journal of Biomedical Imaging* 2012:1-26, article ID 940585.
Alfano et al. (Oct. 1987). "Fluorescence Spectra from Cancerous and Normal Human Breast and Lung Tissues," *IEEE Journal of Quantum Electronics* QE-23(10):1806-1811.
Alm, A. et al. (Jan. 1, 1973). "Ocular and Optic Nerve Blood Flow at Normal and Increased Intraocular Pressures in Monkeys (*Macaca irus*): A Study with Radioactively Labelled Microspheres Including Flow Determinations in Brain and Some Other Tissues," *Experimental Eye Research* 15(1):15-29.
Alonso-Burgos, A. et al.(2006). "Preoperative planning of deep inferior epigastric artery perforator flap reconstruction with multi-slice-CT angiography: imaging findings and initial experience," *Journal of Plastic, Reconstructive & Aesthetic Surgery* 59:585-593.
Ancalmo, N. et al. (1997). "Minimally invasive coronary artery bypass surgery: really minimal?" *Ann. Thorac. Surg.* 64:928-929.
Andersson-Engels, S. et al. (1991). "Fluorescence Characteristics of Atherosclerotic Plaque and Malignant Tumors," in *Optical Methods for Tumor Treatment and Early Diagnosis: Mechanisms and Techniques*, T. J. Dougherty (Ed.), The Society of Photo-optical instrumentation Engineers (SPIE) 1426:31-43, fourteen pages.
Andersson-Engels, S. et al. (Mar. 1989). "Tissue Diagnostics Using Laser-Induced Fluorescence," *Berichte der Bunsengesellschaft für physikalische Chemie* 93(3):335-342.
Angelov, D.N. et al. (Apr. 1999). "Contralateral Trigeminal Nerve Lesion Reduces Polyneuronal Muscle Innervation after Facial Nerve Repair in Rats," *European Journal of Neuroscience* 11(4):1369-1378.

(56) References Cited

OTHER PUBLICATIONS

Annese, V. et al. (2005). "Erthrocytes-Mediated Delivery of Dexamethasone in Steroid-Dependent IBD Patients-a Pilot Uncontrolled Study," *American Journal of Gastroenterology* 100:1370-1375.
Argus-50/CA, Inter cellular CA2+ (calcium ion) Image Analysis system (Feb. 1992). "Observation and 2-dimensional analysis of Ca2+ concentration distribution. Fura-2 and Indo-1 compatible. Ca2+ concentrations are calculated from the fluorescence ratio," pp. 1-10.
Author Unknown. (Jun. 4, 2008)."Invitrogen," Material Safety Data Sheet, p. 1-4.
Awano, T. et al. (Jun. 2010). "Intraoperative EC-IC Bypass Blood Flow Assessment with Indocyanine Green Angiography in Moyamoya and Non-moyamoya Ischemic Stroke," *World Neurosurg.* 73(6):668-674.
Azuma, R. et al. (2008, presented in part Jun. 2007). "Detection of Skin Perforators by Indocyanine Green Fluorescence Nearly Infrared Angiography," *PRS Journal* 122(4):1062-1067.
Balacumarswami, L. et al. (Aug. 2004). "Does Off-Pump Total Arterial Grafting Increase the Incidence of Intraoperative Graft Failure?," *The Journal of Thoracic and Cardiovascular Surgery* 128(2):238-244.
Barton, J.K. et al. (1999) "Simultaneous irradiation and imaging of blood vessels during pulsed laser delivery," *Lasers in Surgery and Medicine* 24(3):236-243.
Bassingthwaighte, J.B. et al. (Apr. 1974). "Organ Blood Flow, Wash-in, Washout, and Clearance of Nutrients and Metabolites," *Mayo Clin. Proc.* 49(4):248-255.
Bek, T. (1999). "Diabetic Maculopathy Caused by Disturbances in Retinal Vasomotion: A New Hypothesis," *Acta Ophthalmologica Scandinavica* 77:376-380.
Benson, R.C. et al. (1978). "Fluorescence Properties of Indocyanine Green as Related to Angiography," *Phys. Med. Biol.* 23(1):159-163.
Black's Medical Dictionary, "Perfusion," 42nd Edition (2009), two pages.
Boer, F.et al. (1994). "Effect of Ventilation on First-Pass Pulmonary Retention of Alfentaril and Sufentanil in Patients Undergoing Coronary Artery Surgery," *British Journal Anesthesia* 73:458-463.
Boldt, J. et al. (Feb. 1990). "Lung management during cardiopulmonary bypass: influence on extravascular lung water," *Journal of Cardiothoracic Anesthesia* 4(1):73-79.
Boldt, J. et al. (1991). "Does the technique of cardiopulmonary bypass affect lung water content?" *European Journal of Cardio-Thoracic Surgery* 5:22-26.
Bütter, A. et al. (May 2005). "Melanoma in Children and the Use of Sentinel Lymph Node Biopsy," *Journal of Pediatric Surgery* 40(5):797-800.
C2741, Compact High Performance video camera for industrial applications with Built-in contrast enhancement circuit, Jun. 1998.
Canada Health. (1997). "Coronary Bypass Surgery and Angioplasty, 1982-1995, Heart Disease and Stroke in Canada," Canada Health, located at <http:/www.hc-sc.gc.ca/hpb>, eighty two pages.
Coffey, J.H. et al. (1984). "Evaluation of Visual Acuity During Laser Photoradiation Therapy of Cancer," *Lasers in Surgery and Medicine* 4(1):65-71.
Conley, M.P. et al. (Oct. 2004). "Anterograde Transport of Peptide-Conjugated Fluorescent Beads in the Squid Giant Axom Identifies a Zip-Code for Synapse," *Biological Bulletin* 207(2):164, one page.
Costa, R.A. et al. (Oct. 2001). "Photodynamic Therapy with Indocyanine Green for Occult Subfoveal Choroidal Neovascularization Caused by Age-Related Macular Degeneration," *Curr. Eye Res.* 23(4):274-275.
Cothren, R.M. et al. (Mar. 1990). "Gastrointestinal Tissue Diagnosis by Laser-Induced Fluorescence Spectroscopy at Endoscopy," *Gastrointestinal Endoscopy* 36(2):105-111.
Dail, W.G. et al. (Oct. 1999). "Multiple Vasodilator Pathways from the Pelvic Plexus to the Penis of the Rat," *International Journal of Impotence Research* 11(5):277-285.

Dan, A.G. et al. (Nov. 2004). "1% Lymphazurin vs 10% Fluorescein for Sentinel Node Mapping in Colorectal Tumors," *Arch Surg.* 139(11):1180-1184.
De Flora, A. (Sep. 1986). "Encapsulation of Adriamycin in human erythrocytes," *Proc. Natl. Acad. Sci., USA* 83(18):7029-7033.
De-Grand, A.M. et al. (Dec. 2003). "An Operational Near Infrared Fluorescence Imaging System Prototype for Large Animal Surgery," *Technology in Cancer Research & Treatment* 2(6):1-10.
Deloach, J.R. (ed.) et al. (1985). *Red Blood Cells as Carriers for Drugs. A Method for Disseminating Chemotherapeutics, Hormones, Enzymes and Other Therapeutic Agents cvia the Circulatory System*, Karger, Basel, CH, pp. v-vii, (Table of Contents).
Deloach, J.R. (Jun. 1983). "Encapsulation of Exogenous Agents in Erythrocytes and the Circulating Survival of Carrier Erythrocytes," *Journal of Applied Biochemistry* 5(3):149-157.
Demos (May/Jun. 2004). "Near-Infrared Autofluorescence Imaging for Detection of Cancer," *Journal of Biomedical Optics* 9(3):587-592.
Desai, N.D. et al. (Oct. 18, 2005, e-published on Sep. 28, 2005) "Improving the Quality of Coronary Bypass Surgery with Intraoperative Angiography," *Journal of the American College of Cardiology* 46(8):1521-1525.
Detter, C. et al. (Aug. 1, 2007). "Fluorescent Cardiac Imaging: A Novel Intraoperative Method for Quantitative Assessment of Myocardial Perfusion During Graded Coronary Artery Stenosis," *Circulation* 116(9):1007-1014.
Detter, C. et al. (Jun. 2011). "Near-Infrared Fluorescence Coronary Angiography: A New Noninvasive Technology for Intraoperative Graft Patency Control." *The Heart Surgery Forum* #2001-6973 5(4):364-369.
Dietz, F.B. et al. (Feb. 2003). "Indocyanine Green: Evidence of Neurotoxicity in Spinal Root Axons," *Anesthesiology* 98(2):516-520.
Digital CCD Microscopy (date unknown). Chapter 14, pp. 259-282.
Dougherty, T.J. et al. (1990). "Cutaneous Phototoxic Occurrences in Patients Receiving Photofrin," *Lasers in Surgery and Medicine* 10(5):485-488.
Draijer, M.J. et al. (Jun. 17-19, 2007). "Laser Doppler Perfusion Imaging with a High-Speed CMOS-Camera," in *Novel Optical Instrumentation for Biomedical Applications III*, C. Depeursinge, ed., Proceedings of SPIE-OSA, Biomedical Optics (Optical Society of America, 2007), SPIE-OSA, 6631:0N1-0N7, nine pages.
Dünne, A. et al. (Nov. 2001)."Value of Sentinel lymphonodectomy in Head and Neck Cancer Patients without Evidence of Lymphogenic Metastatic Disease," *Auris Nasus Larynx* 28(4):339-344.
Ekstrand, M.I. et al. (Feb. 14, 2008). "The Alpha-Herpesviruses: Molecular Pathfinders in Nervous System Circuits," *Trends in Molecular Medicine, Elsevier Current Trends* 14(3):134-140.
Emery R.W. et al. (Aug. 1996). "Revascularization Using Angioplasty and Minimally Invasive Techniques Documented by Thermal Imaging," *The Annals of Thoracic Surgery* 62(2):591-593.
Eren, S. et al. (Dec. 1995). "Assessment of Microcirculation of an Axial Skin Flap Using Indocyanine Green Fluorescence Angiography," *Plast. Reconstr. Surg.* 96(7):1636-1649.
Flower, R. et al. (Apr.-Jun. 1999). "Effects of free and liposome-encapsulated hemoglobin on choroidal vascular plexus blood flow, using the rabbit eye as a model system," *European Journal of Ophthalmology* 9(2):103-114.
Flower, R.W. (1992)."Choroidal Angiography Today and Tomorrow," *Retina* 12(3):189-190.
Flower, R.W. (Apr. 2000). "Experimental Studies of Indocyanine Green Dye-Enhanced Photocoagulation of Choroidal Neovascularization Feeder Vessels," *American Journal of Ophthalmology* 129(4):501-512.
Flower, R.W. (Aug. 2002). "Optimizing Treatment of Choroidal Neovascularization Feeder Vessels Associated with Age-Related Macular Degeneration," *American Journal of Ophthalmology* 134(2):228-239.
Flower, R.W. (Dec. 1973). "Injection Technique for Indocyanine Green and Sodium Fluorescein Dye Angiography of the Eye," *Investigative Opthamology* 12(12):881-895.

(56) References Cited

OTHER PUBLICATIONS

Flower, R.W. (Sep. 1, 1994). "Does Preinjection Binding of Indocyanine Green to Serum Actually Improve Angiograms?," *Arch Ophthalmol.* 112(9):1137-1139.

Flower, R.W. et al. (Aug. 1977). "Quantification of Indicator Dye Concentration in Ocular Blood Vessels," *Exp. Eye Res.* 25(2):103-111.

Forrester et al. (Nov. 1, 2002). "Comparison of Laser Speckle and Laser Doppler Perfusion Imaging: Measurement in Human Skin and Rabbit Articular Tissue," *Medical and Biological Engineering and Computing* 40(6):687-697.

Frangioni, J.V. (Oct. 2003). "In Vivo Near-Infrared Fluorescence Imaging," *Current Opinion in Chemical Biology* 7(5):626-634.

Frenzel H. et al. (Apr. 18, 2008). "In Vivo Perfusion Analysis of Normal and Dysplastic Ears and its Implication on Total Auricular Reconstruction," *Journal of Plastic, Reconstructive and Aesthetic Surgery* 61(Supplement1):S21-S28.

Fritzsch, B. et al. (Aug. 1991)."Sequential Double Labeling With Different Fluorescent Dyes Coupled to Dextran Amines as a Tool to Estimate the Accuracy of Tracer Application and of Regeneration," *Journal of Neuroscience Methods* 39(1):9-17.

Gagnon, A.R. et al. (2006). "Deep and Superficial Inferior Epigastric Artery Perforator Flaps," *Cirugia Plástica Ibero-Latinoamericana* 32(4):7-13.

Gardner, T.J. (1993). "Coronary Artery Disease and Ventricular Aneurysms," in *Surgery, Scientific Principles and Practice*, Greenfield, L.J. (ed.) et al., J.B. Lippincott Co., Philadelphia, PA, pp. 1391-1411, twenty three pages.

Garrett, W.T. et al. (Jul. 8, 1991). "Fluoro-Gold's Toxicity makes it Inferior to True Blue for Long-Term Studies of Dorsal Root Ganglion Neurons and Motoneurons," *Neuroscience Letters* 128(1):137-139.

Geddes, C. D. et al. (2003, e-published on Mar. 20, 2003). "Metal-Enhanced Fluorescence (MEF) Due to Silver Colloids on a Planar Surface: Potential Applications of Indocyanine Green to in Vivo Imaging," *Journal of Physical Chemistry A* 107(18):3443-3449.

Gipponi, M. et al. (Mar. 1, 2004). "New Fields of Application of the Sentinel Lymph Node Biopsy in the Pathologic Staging of Solid Neoplasms: Review of Literature and Surgical Perspectives," *Journal of Surgical Oncology* 85(3):171-179.

Giunta, R.E. et al. (Jul. 2005). "Prediction of Flap Necrosis with Laser Induced Indocyanine Green Fluorescence in a Rat Model," *British Journal of Plastic Surgery* 58(5):695-701.

Giunta, R.E. et al. (Jun. 2000). "The Value of Preoperative Doppler Sonography for Planning Free Perforator Flaps," *Plastic and Reconstructive Surgery* 105(7):2381-2386.

Glossary, Nature, downloaded from the internet <http://www.nature.com/nrg/journal/v4/nl0/glossary/nrgl 183_glossary.html>> HTML on Jun. 30, 2014.

Glover, J.C. et al. (Nov. 1986). "Fluorescent Dextran-Amines Used as Axonal Tracers in the Nervous System of the Chicken Embryo," *Journal of Neuroscience Methods* 18(3):243-254.

Goldstein, J.A. et al. (Dec. 1998). "Intraoperative Angiography to Assess Graft Patency After Minimally Invasive Coronary Bypass," *Ann. Thorac. Surg.* 66(6):1978-1982.

Granzow, J.W. et al. (Jul. 2007)."Breast Reconstruction with Perforator Flaps" *Plastic and Reconstructive Surgery* 120(1):1-12.

Green, H.A. et al. (Jan. 1992). "Burn Depth Estimation Using Indocyanine Green Fluorescence," *Arch Dermatol* 128(1):43-49.

Haglund, M. et al. (Feb. 1996). "Enhanced Optical Imaging of Human Gliomas and Tumor Margins," *Neurosurgery* 38(2):308-317.

Haglund, M.M. et al. (Nov. 1994). "Enhanced Optical Imaging of Rat Gliomas and Tumor Margins," *Neurosurgery* 35(5):930-941.

Hallock, G.G. (Jul. 2003). "Doppler sonography and color duplex imaging for planning a perforator flap," *Clinics in Plastic Surgery* 30(3):347-357.

Hamamatsu Brochure. (May 1997). Specifications for Real-time Microscope Image Processing System: ARGUS-20 with C2400-75i.

Hayashi, J. et al. (Nov. 1993). "Transadventitial Localization of Atheromatous Plaques by Fluorescence Emission Spectrum Analysis of Mono-L Aspartyl-Chlorin e6," *Cardiovascular Research* 27(11):1943-1947.

Hayata, Y. et al. (Jul. 1982). "Fiberoptic Bronchoscopic Laser Photoradiation for Tumor Localization in Lung Cancer," *Chest* 82(1):10-14.

He, Z. (Feb. 2009). "Fluorogold Induces Persistent Neurological Deficits and Circling Behavior in Mice Over-Expressing Human Mutant Tau," *Current Neurovascular Research* 6(1):54-61.

Herts, B.R. (May 2003). "Imaging for Renal Tumors," *Current Opin.. Urol.*13(3):181-186.

Hirano et al. (1989). "Photodynamic Cancer Diagnosis and Treatment System Consisting of Pulse Lasers and an Endoscopic Spectro-Image Analyzer," *Laser in Life Sciences* 3(2):99-116.

Holm, C. et al. (2002). "Monitoring Free Flaps Using Laser-Induced Fluorescence of Indocyanine Green: A Preliminary Experience," *Microsurgery* 22(7):278-287.

Holm, C. et al. (Apr. 2003, e-published on Feb. 25, 2003). "Laser-Induced Fluorescence of Indocyanine Green: Plastic Surgical Applications," *European Journal of Plastic Surgery* 26(1):19-25.

Holm, C. et al. (Dec. 1, 2002). "Intraoperative Evaluation of Skin-Flap Viability Using Laser-Induced Fluorescence of Indocyanine Green", *British Journal of Plastic Surgery* 55(8):635-644.

Humblet, V. et al. (Oct. 2005). "High-Affinity Near-Infrared Fluorescent Small-Molecule Contrast Agents for In Vivo Imaging of Prostate-Specific Membrane Antigen," *Molecular Imaging* 4(4):448-462.

Hung, J. et al. (1991). "Autofluorescence of Normal and Malignant Bronchial Tissue," *Lasers in Surgery and Medicine* 11(2) :99-105.

Ikeda, S. (Jul. 1989). "Bronichial Telivision Endoscopy," *Chest* 96(1):41S-42S.

Jaber, S.F. et al. (Sep. 1998). "Role of Graft Flow Measurement Technique in Anastomotic Quality Assessment in Minimally Invasive CABG," *Ann. Thorac. Surg.* 66(3):1087-1092.

Jagoe, J.R. et al. (1989). "Quantification of retinal damage during cardiopulmonary bypass," Third International Conference on Image Processing and its Applications (Conf. Publ. No. 307), IEE, pp. 319-323.

Jamis-Dow, C.A. et al. (Mar. 1996). "Small (< or = 3-cm) Renal Masses: Detection with CT versus US and Pathologic Correlation," *Radiology* 198(3):785-788.

Jolion, J. et al. (Aug. 1991). "Robust Clustering with Applications in Computer Vision," *IEEE Transactions on Pattern Analysis and Machine Intelligence* 13(8):791-802.

Kamolz, L.-P. et al. (Dec. 2003). "Indocyanine Green Video Angiographies Help to Identify Burns Requiring Operation," *Burns* 29(8):785-791.

Kapadia, C.R. et al. (Jul. 1990). "Laser-Induced Fluorescence Spectroscopy of Human Colonic Mucosa. Detection of Adenomatous Transformation," *Gastroenterology* 99(1):150-157.

Kato, H. et al. (Jun. 1985). "Early Detection of Lung Cancer by Means of Hematoporphyrin Derivative Fluorescence and Laser Photoradiation," *Clinics in Chest Medicine* 6(2):237-253.

Kato, H. et al. (Jun. 1990). "Photodynamic Diagnosis in Respiratory Tract Malignancy Using an Excimer Dye Laser System," *Journal of Photochemistry and Photobiology, B. Biology* 6(1-2):189-196.

Keon, W.J. et al. (Dec. 1979). "Coronary Endarterectomy: An Adjunct to Coronary Artery Bypass Grafting," *Surgery* 86(6):859-867.

Kim, S. et al. (2004, e-published Dec. 7, 2003). "Near-Infrared Fluorescent Type II Quantum Dots for Sentinel Lymph Node Mapping," *Nature Biotechnology* 22(1):93-97.

Kiryu, J. et al. (Sep. 1994). "Noninvasive Visualization of the Choriocapillaris and its Dynamic Filling," *Investigative Ophthalmology & Visual Science* 35(10):3724-3731.

Kitai, T. et al. (Jul. 2005). "Fluorescence Navigation with Indocyanine Green for Detecting Sentinel Lymph Nodes in Breast Cancer," *Breast Cancer* 12(3):211-215.

Kleszmńska, H. et al. (Mar. 2005). "Hemolysis of Erythrocytes and Erythrocyte Membrane Fluidity Changes by New Lysosomotropic Compounds," *Journal of Fluorescence* 15(2):137-141.

(56) References Cited

OTHER PUBLICATIONS

Köbbert, C. et al. (Nov. 2000). "Current Concepts in Neuroanatomical Tracing," *Progress in Neurobiology* 62(4):327-351.

Kömürcü, F. et al. (Feb. 2005). "Management Strategies for Peripheral Iatrogenic Nerve Lesions," *Annals of Plastic Surgery* 54(2):135-139.

Krishnan, K. G. et al. (Apr. 1, 2005). "The Role of Near-Infrared Angiography in the Assessment of Post-Operative Venous Congestion in Random Pattern, Pedicled Island and Free Flaps", *British Journal of Plastic Surgery* 58(3):330-338.

Kuipers, J.A. et al. (1999). "Recirculatory and Compartmental Pharmacokinetic Modeling of Alfentanil Pigs, the Influence of Cardiac Output," *Anesthesiology* 90(4):1146-1157.

Kupriyanov, V.V. et al. (Nov. 2004). "Mapping Regional Oxygenation and Flow in Pig Hearts in Vivo Using Near-infrared Spectroscopic Imaging," *Journal of Molecular and Cellular Cardiology* 37(5):947-957.

Kurihara, K. et al. (Jun. 1984). "Nerve Staining with Leucomethylene Blue: An Experimental Study," *Plastic and Reconstruction Surgery* 73(6):960-964.

Kyo, S. "Use of Ultrasound Cardiology during Coronary Artery Bypass Surgery," *Heart and Blood Vessel Imaging II*.

Lam, S. et al. (1991). "Mechanism of Detection of Early Lung Cancer by Ratio Fluorometry," *Lasers in Life Sciences* 4(2):67-73.

Lam, S. et al. (Feb. 1990). "Detection of Early Lung Cancer Using Low Dose Photofrin II," *Chest* 97(2):333-337.

Lam, S. et al. (Jul. 1, 1990). "Detection of Lung Cancer by Ratio Fluorometry With and Without Photofrin II," *Proc. SPIE—Optical Fibers in Medicine V* 1201:561-568.

Lam, S. et al. (Nov. 1-4, 1990). "Fluorescence Imaging of Early Lung Cancer," *Annual International Conference of the IEEE Engineering in Medicine and Biology Society* 12(3):1142-1143.

Lam, S.C. et al. (1993). "Fluorescence Detection," Chapter 20 in *Lung Cancer*, Roth, J.A. (ed.), et al., Blackwell Scientific Publications Inc., 238 Main Street, Cambridge, Massachusetts, 02142, pp. 325-338, sixteen pages.

Lanciego, J.L. et al. (Jun. 1998). "Multiple Neuroanatomical Tracing in Primates," *Brain Research Protocols* 2(4):323-332.

Lanciego, J.L. et al. (Oct. 1998). "Multiple Axonal Tracing: Simultaneous Detection of Three Tracers in the Same Section," *Histochemistry and Cell Biology* 110(5):509-515.

Laub, G.W. et al. (Nov./Dec. 1989). "Experimental Use of Fluorescein for Visualization of Coronary Arteries," *Vascular and Endovascular Surgery* 23(6):454-457.

Lee, E.T. et al. (Mar. 1997). "A New Method for Assessment of Changes in Retinal Blood Flow," *Medical Engineering & Physics* 19(2):125-130.

Leissner, J. et al. (Jan. 2004). "Extended Radical Lymphadenectomy in Patients with Urothelial Bladder Cancer: Results of a Prospective Multicenter Study," *The Journal of Urology* 171(1):139-144.

Leithner, "Untersuchung der Sauerstoffkonzentrationsveranderungen in der Mikrozirkulation des Hirnkortex von Ratten bei funktioneller Stimulation mittels Phosphorescence Quenching," [dissertation], Jul. 14, 2003; retrieved from the Internet: <http://edoc.hu-berlin.de/dissertationen/leith nerch ristoph-2003-07-14/> [English Abstract and Machine Translation].

Liedberg et al. (2003). "Sentinel-Node-Diagnostik Beim Invasiven (Bladder Cancer and the Sentinel Node Concept)," *Aktuel Urol.* 34:115-118 (English Abstract Only).

Liedberg, F. et al. (Jan. 2006). "Intraoperative Sentinel Node Detection Improves Nodal Staging in Invasive Bladder Cancer," *The Journal of Urology* 175(1):84-89.

Lippincott's New Medical Dictionary. "Perfusion," p. 707 (1897), three pages.

Liptay, M.J. (Mar. 2004). "Sentinel Node Mapping in Lung Cancer," *Annals of Surgical Oncology* 11(Supplement 3):271S-274S.

Lund, F. et al. (Nov. 1997). "Video Fluorescein Imaging of the Skin: Description of an Overviewing Technique for Functional Evaluation of Regional Cutaneous Blood Evaluation of Regional Cutaneous Perfusion in Occlusive Arterial Disease of the Limbs," *Clinical Physiology* 17(6):619-633.

Mack, M.J. et al. (Sep. 1998). "Arterial Graft Patency in Coronary Artery Bypass Grafting: What Do We Really Know?," *Ann. Thorac. Surg.* 66(3)1055-1059.

Magnani, M. et al. (Aug. 1998). "Erythrocyte Engineering for Drug Delivery and Targeting," *Biotechnology and Applied Biochemistry* 28(Part 1):1-6.

Malmstrom et al. (Nov. 2002). "Early Metastatic Progression of Bladder Carcinoma: Molecular Profile of Primary Tumor and Sentinel Lymph Node," *The Journal of Urology* 168(5):2240-2244.

Malmström, P.U. et al. (Jul. 2004). "RE: Extended Radical Lymphadenectomy in Patients With Urothelial Bladder Cancer: Results of a Prospective Multicenter Study," *J. of Urol.* 172(1):386, one page.

Marangos, N. et al. (Dec. 2001). "In Vivo Visualization of the Cochlear Nerve and Nuclei with Fluorescent Axonal Tracers," *Hearing Research* 162(1-2):48-52.

Martinez-Pérez, M. et al. (Sep. 19, 1996). "Unsupervised Segmentation Based on Robust Estimation and Cooccurrence Data," *Proceedings of the International Conference on Miage Processing (ICIP) Lausanne* 3:943-945.

May, S. (May/Jun. 1995). "Photonic Approaches to Burn Diagnostics," *Biophotonics International* pp. 44-50.

McKee, T.D. et al. (Mar. 1, 2006). "Degradation of Fibrillar Collagen in a Human Melanoma Xenograft Improves the Efficacy of an Oncolytic Herpes Simplex Virus Vector," *Cancer Research* 66(5):2509-2513.

Merriam Webster Medline Plus Medical Dictionary. "Perfusion," located at http://www.merriam-webster.com/medlineplus/perfusion, last visited on Apr. 15, 2015, one page.

Minciacchi, D. et al. (Jul. 1991). "A Procedure for the Simultaneous Visualization of Two Anterograde and Different Retrograde Fluorescent Tracers—Application to the Study of the Afferent-Efferent Organization of Thalamic Anterior Intralaminar Nuclei" *Journal of Neuroscience Methods* 38(2-3):183-191.

Mitaka USA, Inc. (2015). "PDE Breast Free Flap Evaluation," located at <http://mitakausa.comicategory/pde_education/flaps/, last visited on Dec. 29, 2015, four pages.

Mitaka USA, Inc. (2015). "PDE-Neo" located at <http://mitakausa.com/pde-neo/>, last visited on Dec. 29, 2015, two pages.

Mohr, F.W. et al. (May 1997). "Thermal Coronary Angiography: A Method for Assessing Graft Patency and Coronary Anatomy in Coronary Bypass Surgery," *Ann Thorac. Surgery* 63(5):1506-1507.

Montán, S. et al. (Feb. 1, 1985). "Multicolor Imaging and Contrast Enhancement in Cancer-Tumor Localization Using Laser-Induced Fluorescence in Hematoporphyrin-Derivative-Bearing Tissue," *Optics Letters* 10(2):56-58.

Mothes, H. et al. (Nov. 2004). "Indocyanine-Green Fluorescence Video Angiography Used Clinically to Evaluate Tissue Perfusion in Microsurgery," *The Journal of Trauma Injury, Infection, and Critical Care* 57(5):1018-24.

Motomura et al. (1999). "Sentinel Node Biopsy Guided by Indocyanine Green Dye in Breast Cancer Patients," *Japan J. Clin. Oncol.* 29(12):604-607.

Mullooly, V.M. et al. (1990). "Dihematoporphyrin Ether-Induced Photosensitivity in Laryngeal Papilloma Patients," *Lasers in Surgery and Medicine* 10(4):349-356.

Murphy (2001). "Digital CCD Microscopy," Chapter 14 in *Fundamentals of Light Microscopy and Electronic Imaging*, John Wiley and Sons, pp. i-xi and 259-281.

Nahlieli, O. et al. (Mar. 2001). "Intravital Staining with Methylene Blue as an Aid to Facial Nerve Identification in Parotid Gland Surgery" *J. Oral Maxillofac. Surgery* 59(3):355-356.

Nakamura, T. et al. (1964). "Use of Novel Dyes, Coomassie Blue and Indocyanine Green in Dye Dilution Method," Tohoka University, Nakamura Internal Department, The Tuberculosis Prevention Society, Tuberculosis Research Laboratory, 17(2):1361-1366.

Nakayama, A. et al. (Oct. 2002). "Functional Near-Infrared Fluorescence Imaging for Cardiac Surgery and Targeted Gene Therapy," *Molecular Imaging* 1(4):365-377.

(56) References Cited

OTHER PUBLICATIONS

Naumann, T. et al. (Nov. 15, 2000). "Retrograde Tracing with Fluoro-Gold: Different Methods of Tracer Detection at the Ultrastructural Level and Neurodegenerative Changes of Back-Filled Neurons in Long-Term Studies," *Journal of Neuroscience Methods* 103(1):11-21.
Newman et al. (Oct. 31, 2008). "Update on the Application of Laser-Assisted Indocyanine Green Fluorescent Dye Angiography in Microsurgical Breast Reconstruction," American Society of Plastic Surgeons, Plastic Surgery 2008, 2 pages.
Nimura, H. et al. (May 2004, e-published on Mar. 22, 2004). "Infrared Ray Electronic Endoscopy Combined with Indocyanine Green Injection for Detection of Sentinel Nodes of Patients with Gastric Cancer," *British Journal of Surgery* 91(5):575-579.
Novadaq Technologies Inc. (Jan. 29, 2007). "Novadaq Imaging System Receives FDA Clearance for use During Plastic Reconstructive Surgery," *PR Newswire* three pages.
Oddi, A. et al. (Jun. 1996). "Intraoperative Biliary Tree Imaging with Cholyl-Lysyl-Fluorescein: An Experimental Study in the Rabbit" *Surgical Laparoscopy & Endoscopy* 6(3):198-200.
Ogata, F. et al. (Jun. 2007). "Novel Lymphography Using Indocyanine Green Dye for Near-Infrared Fluorescence Labeling," *Annals of Plastic Surgery* 58(6):652-655.
Ohnishi, S. et al. (Jul.-Sep. 2005). "Organic Alternatives to Quantum Dots for Intraoperative Near-Infrared Fluorescent Lymph Node Mapping" *Molecular Imaging* 4(3):172-181.
Ooyama, M. (Oct. 12-15, 1994). The 8th Congress of International YAG Laser Symposium, The 15th Annual Meeting of Japan Society for Laser Medicine, Sun Royal Hotel, Japan.
Oxford Concise Medical Dictionary. "Perfusion," p. 571 (1980), three pages.
Pagni, S. et al. (Jun. 1997). "Anastomotic Complications in Minimally Invasive Coronary Bypass Grafting," *Ann. Thorac. Surg.* 63(6 Suppl):S64-S67.
Palcic et al. (1991). "Lung Imaging Fluorescence Endoscope: A Device for Detection of Occult Lung Cancer," *Medical Design and Material*, thirteen pages.
Palcic, B. et al. (1990). "Development of a Lung Imaging Fluorescence Endoscope," *Annual International Conference of the IEEE Engineering in Medicine and Biology Society* 12(1):0196-0197.
Palcic, B. et al. (Aug. 1, 1990). "The Importance of Image Quality for Computing Texture Features in Biomedical Specimens," *Proc. SPIE* 1205:155-162.
Palcic, B. et al. (Jun. 1, 1991). "Lung Imaging Fluorescence Endoscope: Development and Experimental Prototype," *Proc. SPIE* 1448:113-117.
Palcic, B. et al. (Mar. 1991). "Detection and Localization of Early Lung Cancer by Imaging Techniques," *Chest* 99(3):742-743.
Pandharlpande, P.V. et al. (Mar. 2005). "Perfusion Imaging of the Liver: Current Challenges and Future Goals," *Radiology* 234(3):661-673.
Paques, M. et al. (Mar. 2003). "Axon-Tracing Properties of Indocyanine Green," *Arch Ophthalmol.* 121(3):367-370.
Parungo, C.P. et al. (Apr. 2005). "Intraoperative Identification of Esophageal Sentinel Lymph Nodes with Near-Infrared Fluorescence Imaging," *The Journal of Thoracic and Cardiovascular Surgery* 129(4):844-850.
Parungo, C.P. et al. (Dec. 2004, e-published on Nov. 15, 2004). "In Vivo Optical Imaging of Pleural Space Drainage to Lymph Nodes of Prognostic Significance," *Annals of Surgical Oncology* 11(12):1085-1092.
Peak, M.J. et al. (1986). "DNA-to-Protein Crosslinks and Backbone Breaks Caused by Far-and Near-Ultraviolet and Visible Light Radiations in Mammalian Cells," in *Mechanism of DNA Damage and Repair, Implications for Carcinogenesis and Risk Assessment*, SIMIC, M.G. (ed.) et al., Plenum Press, 233 Spring Street, New York, N.Y. 10013, pp. 193-202.
Pfister, A.J. et al. (Dec. 1992). "Coronary Artery Bypass Without Cardiopulmonary Bypass," *Ann. Thorac. Surg.* 54(6)1 085-1092, (Discussion by S.R. Gundry).

Phillips, R.P. et al. (1991). "Quantification of Diabetic Maculopathy by Digital Imaging of the Fundus," *Eye* 5(1):130-137.
Piermarocchi, S. et al. (Apr. 2002). "Photodynamic Therapy Increases the Eligibility for Feeder Vessel Treatment of Choroidal Neovascularization Caused by Age-Related Macular Degeneration," *American Journal of Ophthalmology* 133(4):572-575.
Profio, A.E. et al. (Jul.-Aug. 1984). "Fluorometer for Endoscopic Diagnosis of Tumors," *Medical Physics* 11(4):516-520.
Profio, A.E. et al. (Jun. 1, 1991). "Endoscopic Fluorescence Detection of Early Lung Cancer," *Proc. SPIE* 1426:44-46.
Profio, A.E. et al. (Nov./Dec. 1979). "Laser Fluorescence Bronchoscope for Localization of Occult Lung Tumors," *Medical Physics* 6:523-525.
Profio, A.E. et al. (Sep.-Oct. 1986). "Digital Background Subtraction for Fluorescence Imaging," *Medical Physics* 13(5):717-721.
Puigdellivol-Sanchez, A. et al. (Apr. 15, 2002). "On the Use of Fast Blue, Fluoro-Gold and Diamidino Yellow for Retrograde Tracing After Peripheral Nerve Injury: Uptake, Fading, Dye Interactions, and Toxicity," *Journal of Neuroscience Methods* 115(2):115-127.
Pyner, S. et al. (Nov. 2001). "Tracing Functionally Identified Neurones in a Multisynaptic Pathway in the Hamster and Rat Using Herpes Simplex Virus Expressing Green Fluorescent Protein," *Experimental Physiology* 86(6):695-702.
Raabe et al. (2009, e-published on Nov. 12, 2008). "Laser Doppler Imaging for Intraoperative Human Brain Mapping", *NeuroImage* 44:1284-1289.
Raabe, A. et al. (Jan. 2003). "Near-Infrared Indocyanine Green Video Angiography: A New Method for Intraoperative Assessment of Vascular Flow," *Neurosurgery* 52(1):132-139.
Rava, R.P. et al. (Jun. 1, 1991). "Early Detection of Dysplasia in Colon and Bladder Tissue Using Laser-Induced Fluorescence," *Proc. SPIE* 1426:68-78.
Razum, N. et al. (Nov. 1987). "Skin Photosensitivity: Duration and Intensity Following Intravenous Hematoporphyrin Derivatives, HpD and DHE, " *Photochemistry and Photobiology* 46(5):925-928.
Report on Observation by C2400-75i and ARGUS20 Under Low illumination conditions, Jan. 17, 2008.
Reuthebuch, O et al. (Feb. 2004). "Novadaq SPY: Intraoperative Quality Assessment in Off Pump Coronary Artery Bypass Grafting," *Chest* 125(2):418-424.
Reuthebuch, O.T. et al. (May 2003). "Graft Occlusion After Deployment of the Symmetry Bypass System," *Ann. Thorac. Surg.* 75(5):1626-1629.
Richards-Kortum, R. et al. (Jun. 1991). "Spectroscopic Diagnosis of Colonic Dysplasia: Spectroscopic Analysis," *Biochemistry and Photobiology* 53(6):777-786.
Roberts, W.W. et al. (Dec. 1997). "Laparoscopic Infrared Imaging," *Surg. Endoscopy* 11(12):1221-1223.
Rodnenkov, O.V. et al. (May 2005). "Erythrocyte Membrane Fluidity and Haemoglobin Haemoporphyrin Conformation: Features Revealed in Patients with Heart Failure," *Pathophysiology* 11(4):209-213.
Ropars, C. (ed.) et al. (1987). *Red Blood Cells as Carriers for Drugs. Potential therapeutic Applications*, Pergamon Press, Oxford, New York, pp. v-viii, (Table of Contents only).
Ross, G.L. et al. (Dec. 2002). "The Ability of Lymphoscintigraphy to Direct Sentinel Node Biopsy in the Clinically N0 Neck for Patients with Head and Neck Squamous Cell Carcinoma," *The British Journal of Radiology* 75(900):950-958.
Ross, G.L. et al. (Jul. 2004, e-published on Jun. 14, 2000). "Sentinel Node Biopsy in Head and Neck Cancer: Preliminary Results of a Multicenter Trial," *Annals of Surgical Oncology* 11(7):690-696.
Rossi, L. et al. (2001). "Erthrocyte-Mediated Delivery of Dexamethasone in Patients with Chronic Obstructive Pulmonary Disease," *Biotechnol. Appl. Biochem.* 33:85-89.
Rossi, L. et al. (1999). "Heterodimer-Loaded Erthrocytes as Bioreactors for Slow Delivery of the Antiviral Drug Azidothymidine and the Antimycobacterial Drug Ethambutol," *Aids Research and Human Retroviruses* 15(4):345-353.
Rossi, L. et al. (2004). "Low Doses of Dexamethasone Constantly Delivered by Autologous Erythrocytes Slow the Progression of Lung Disease in Cystic Fibrosis Patients," *Blood Cells, Molecules, and Diseases* 33:57-63.

(56) References Cited

OTHER PUBLICATIONS

Rozen, W.M. et al. (Jan. 2008). "Preoperative Imaging for DIEA Perforator Flaps: A Comparative Study of Computed Tomographic Angiography and Doppler Ultrasound," *Plastic and Reconstructive Surgery* 121(1):9-16.

Rubben, A. et al. (Mar. 1994). "Infrared Videoangiofluorography of the Skin with Indocyanine Green—Rat Random Cutaneous Flap Model and Results in Man," *Microvascular Research* 47(2):240-251.

Rubens, F.D. et al. (2002). "A New and Simplified Method for Coronary and Graft Imaging During CABG," *The Heart Surgery Forum* 5(2):141-144.

Sakatani, K. et al. (Nov. 1997). "Noninvasive Optical Imaging of the Subarchnoid Space and Cerebrospinal Fluid Pathways Based on Near Infrared Fluorescence," *J. Neurosurg.* 87(5):738-745.

Salmon, E.D. et al. (Oct. 1994). "High Resolution Multimode Digital Imaging System for Mitosis Studies in Vivo and in Vitro," *Biol. Bull* 187(2):231-232.

Sato, et al., (1991). "Development of a Visualization Method for the Microcirculation of Deep Viscera Using an Infrared Intravital Microscope System," *Research on ME Devices and ME Technology*, five pages, (with English Translation).

Schaff, H.V. et al. (Oct. 15, 1996). "Minimal Thoracotomy for Coronary Artery Bypass: Value of Immediate Postprocedure Graft Angiography," *Supplement to Circulation* 94(8):I-51, (Abstract No. 0289), two pages.

Schellingerhout, D. et al. (Oct. 2000). "Quantitation of HSV Mass Distribution in a Rodent Brain Tumor Model," *Gene Therapy* 7(19):1648-1655.

Schmued, L. et al. (Aug. 27, 1990). "In Vivo Anterograde and Retrograde Axonal Transport of the Fluorescent Rhodamine-Dextran-Amine, Fluoro-Ruby, Within the CNS," *Brain Research* 526(1):127-134.

Schmued, L.C. et al. (Oct. 29, 1993). "Intracranial Injection of Fluoro-Gold Results in the Degeneration of Local but not Retrogradely Labeled Neurons," *Brain Research* 626(1-2):71-77.

Schneider Jr., H.C. et al. (Jan. 1975). "Fluorescence of Testicle, An Indication of Viability of Spermatic Cord After Torsion," *Urology* V(1):133-136.

Seeman, P. (Jan. 1, 1967). "Transient Holes in the Erythrocyte Membrane During Hypotonic Hemolysis and Stable Holes in the Membrane After Lysis by Saponin and Lysolecithin," *Journal of Cell Biology* 32(1):55-70.

Sekijima, M. et al. (Sep. 2004). "An Intraoperative Fluorescent Imaging System in Organ Transplantation," *Transplantation Proceedings* 36(7):2188-2190.

Serov, A. et al. (Mar. 1, 2002). "Laser Doppler Perfusion Imaging with a Complimentary Metal Oxide Semiconductor Image Sensor," *Optics Letters* 27(5):300-302.

Serov, A.N. et al. (Sep. 23, 2003). "Quasi-Parallel Laser Doppler Perfusion Imaging Using a CMOS Image Sensor," *Proc. SPIE* 5067:73-84.

Sezgin, M. et al. (Jan. 2004). "Survey Over Image Thresholding Techniques and Quantitative Performance Evaluation," *Journal of Electronic Imaging* 13(1):146-165.

Sherif, A. et al. (Sep. 2001). "Lymphatic Mapping and Detection of Sentinel Nodes in Patients with Bladder Cancer," *The Journal of Urology* 166(3):812-815.

Sheth, S.A. et al. (Apr. 22, 2004)"Linear and Nonlinear Relationships between Neuronal Activity, Oxygen Metabolism, and Hemodynamic Responses," *Neuron* 42(2):347-355.

Shoaib, T. et al. (Jun. 1, 2001). "The Accuracy of Head and Neck Carcinoma Sentinel Lymph Node Biopsy in the Clinically NO Neck," *Cancer* 91(11):2077-2083.

Siemers, B.M. et al. (Nov. 2001). "The Acoustic Advantage of Hunting at Low Heights Above Water: Behavioual Experiments on the European 'Trawling' Bats Myotis Capaccinii, M Dasycneme and M. Daubentonii," *J. Eperimental Biol.* 204(Pt. 22):3843-3854.

Skalidis, E.I. et al. (Nov. 16, 2004). "Regional Coronary Flow and Contractile Reserve in Patients with Idiopathic Dilated Cardiomyopathy," *Journal of the American College of Cardiology* 44(10):2027-2032.

Slakter, J.S. et al. (Jun. 1995). "Indocyanine-Green Angiography," *Current Opinion in Ophthalmology* 6(III):25-32.

Smith, G.A. et al. (Mar. 13, 2001). "Herpesviruses Use Bidirectional Fast-Axonal Transport to Spread in Sensory Neurons," *Proceedings of the National Academy of Sciences of the United States of America* 98(6):3466-3470.

Soltesz, E.G. et al. (Jan. 2005). "Intraoperative Sentinel Lymph Node Mapping of the Lung Using Near-Infrared Fluorescent Quantum Dots," *Ann. Thorac. Surg.* 79(1):269-277.

Staurenghi, G. et al. (Dec. 2001)."Combining Photodynamic Therapy and Feeder Vessel Photocoagulation: A Pilot Study," *Seminars in Ophthalmology* 16(4):233-236.

Stern, M.D. (Mar. 6, 1975). "In Vivo Evaluation of Microcirculation by Coherent Light Scattering," *Nature* 254(5495):56-58.

Still, J. et al. (Mar. 1999). "Evaluation of the Circulation of Reconstructive Flaps Using Laser-Induced Fluorescence of Indocyanine Green," *Ann. Plast. Surg.* 42(3):266-274.

Still, J.M. et al. (Jun. 2001). "Diagnosis of Burn Depth Using Laser-Induced Indocyanine Green Fluorescence: A Preliminary Clinical Trial," *Burns* 27(4):364-371.

Stoeckli, S.J. et al. (Sep. 2001). "Sentinel Lymph Node Evaluation in Squamous Cell Carcinoma of the Head and Neck," *Otolaryngol Head Neck Surg.* 125(3):221-226.

Subramanian, V.A. et al. (Oct. 15, 1995). "Minimally Invasive Coronary Bypass Surgery: A Multi-Center Report of Preliminary Clinical Experience," *Supplement to Circulation* 92(8):I-645, (Abstract No. 3093), two pages.

Sugi, K. et al. (Jan. 2003). "Comparison of Three Tracers for Detecting Sentinel Lymph Nodes in Patients with Clinical N0 Lung Cancer," *Lung Cancer* 39(1):37-40.

Sugimoto, K. et al. (Jun. 2008, e-published on Mar. 19, 2008). "Simultaneous Tracking of Capsid, Tegument, and Envelope Protein Localization in Living Cells Infected With Triply Fluorescent Herpes Simplex Virus 1," *Journal of Virology* 82(11):5198-5211.

Suma, H. et al. (2000). "Coronary Artery Bypass Grafting Without Cardiopulmonary Bypass in 200 Patients," *J. Cardiol.* 36(2):85-90, (English Abstract only).

Taggart, D.P. et al. (Mar. 2003). "Preliminary Experiences with a Novel Intraoperative Fluorescence Imaging Technique to Evaluate the Patency of Bypass Grafts in Total Arterial Revascularization," *Ann Thorac Surg.* 75(3):870-873.

Taichman, G.C. et al. (Jun. 1987). "The Use of Cardio-Green for lntraoperative Visualization of the Coronary Circulation: Evaluation of Myocardial Toxicity," *Texas Heart Institute Journal* 14(2):133-138.

Takahashi, M. et al. (Sep. 2004). "SPY: An Innovative Intra-Operative Imaging System to Evaluate Graft Patency During Off-Pump Coronary Artery Bypass Grafting," *Interactive Cardio Vascular and Thoracic Surgery* 3(3):479-483.

Takayama, T. et al. (Apr. 1992). "Intraoperative Coronary Angiography Using Fluorescein Basic Studies and Clinical Application," *Vascular and Endovascular Surgery* 26(3):193-199.

Takayama, T. et al. (Jan. 1991). "Intraoperative Coronary Angiography Using Fluorescein" *The Annals of Thoracic Surgery* 51(1):140-143.

Tanaka, E. et al. (Jul. 2009). "Real-time Assessment of Cardiac Perfusion, Coronary Angiography, and Acute Intravascular Thrombi Using Dual-channel Near-infrared Fluorescence Imaging," *The Journal of Thoracic and Cardiovascular Surgery* 138(1):133-140.

Tang, G.C. et al. (1989). "Spectroscopic Differences between Human Cancer and Normal Lung and Breast Tissues," *Lasers in Surgery and Medicine* 9(3):290-295.

Taylor, K.M. (Apr. 1998). "Brain Damage During Cardiopulmonary Bypass," *Annals of Thoracic Surgery* 65(4):S20-S26.

The American Heritage Medical Dictionary. "Perfuse." p. 401 (2008), three pages.

Thelwall, P.E. et al. (Oct. 2002). "Human Erythrocyte Ghosts: Exploring the Origins of Multiexponential Water Diffusion in a

(56) References Cited

OTHER PUBLICATIONS

Model Biological Tissue with Magnetic Resonance," *Magnetic Resonance in Medicine* 48(4):649-657.

Torok, B. et al. (May 1996). "Simultaneous Digital Indocyanine Green and Fluorescein Angiography," *Klinische Monatsblatter Fur Augenheilkunde* 208(5):333-336, (Abstract only), two pages.

Tsutsumi, D. et al. "Moisture Detection of road surface using infrared camera," Reports of the Hokkaido Industrial Research Institute (No. 297), Issued on Nov. 30, 1998, two pages.

Tubbs, R.S. et al. (Apr. 2005). "Anatomic Landmarks for Nerves of the Neck: A Vade Mecum for Neurosurgeons," *Neurosurgery* 56(2 Suppl.):ONS256-ONS260.

Unno, N. et al. (Feb. 2008, e-published on Oct. 26, 2007). "Indocyanine Green Fluorescence Angiography for intraoperative assessment of Blood flow: A Feasibility Study," *Eur J Vasc Endovasc Surg.* 35(2):205-207.

Uren, R.F. (Jan. 2004). "Cancer Surgery Joins the Dots," *Nature Biotechnology* 22(1):38-39.

Valero-Cabré, A. et al. (Jan. 15, 2001). "Superior Muscle Reinnervation after Autologous Nerve Graft or Poly-L-Lactide-ϵ-Caprolactone (PLC) Tube Implantation in Comparison to Silicone Tube Repair," *Journal of Neuroscience Research* 63(2):214-223.

Van Son, J.A.M. et al. (Nov. 1997). "Thermal Coronary Angiography for Intraoperative Testing of Coronary Patency in Congenital Heart Defects," *Ann Thorac Surg.* 64(5):1499-1500.

Verbeek, X. et al. (2001). "High-Resolution Functional Imaging With Ultrasound Contrast Agents Based on RF Processing in an In Vivo Kidney Experiment", *Ultrasound in Med. & Biol.* 27(2):223-233.

Wachi, A. et al. (Apr. 1995). "Characteristics of Cerebrospinal Fluid Circulation in Infants as Detected With MR Velocity Imaging," *Child's Nery Syst* 11(4):227-230.

Wagnieres, G.A. et al. (Jul. 1, 1990). "Photodetection of Early Cancer by Laser Induced Fluorescence of a Tumor-Selective Dye: Apparatus Design and Realization," *Proc. SPIE* 1203:43-52.

Weinbeer, M. et al. (Nov. 25, 2013). "Behavioral Flexibility of the Trawling Long-Legged Bat, Macrophyllurn Macrophyllum (Phyllostomidae)," *Frontiers in Physiology* 4(Article 342):1-11.

What is Perfusion? A Summary of Different Typed of Perfusion. (Sep. 1, 2004). Located at, <http://www.perfusion.com/cgi-bin/absolutenm/templates/articledisplay.asp?articleid=1548#.Vo8Hv02FPGj>, last visited on Jan. 7, 2016, two pages.

Wise, R.G. et al. (Nov. 2005). "Simultaneous Measurement of Blood and Myocardial Velocity in the Rat Heart by Phase Contrast MRI Using Sparse q-Space Sampling" *Journal of Magnetic Resonance Imaging* 22(5):614-627.

Woitzik, J. et al. (Apr. 2005). "Intraoperative Control of Extracranial-Intracranial Bypass Patency by Near-Infrared Indocyanine Green Videoangiography," *J. Neurosurg.* 102(4):692-698.

Wollert, H.G. et al. (Dec. 1989). "Intraoperative Visualization of Coronary Artery Fistula Using Medical Dye," *The Thoracic and Cardiovascular Surg.* 46(6):382-383.

Wu, C. et al. (Apr. 15, 2005). "cGMP (Guanosine 3',5'-Cyclic Monophosphate) Transport Across Human Erythrocyte Membranes," *Biochemical Pharmacology* 69(8):1257-1262.

Yada, T. et al. (May 1993). "In Vivo Observation of Subendocardial Microvessels of the Beating Porcine Heart Using a Needle-Probe Videomicroscope with a CCD Camera," *Circulation Research* 72(5):939-946.

Yamaguchi, S. et al. (Apr. 2005). "Evaluation of Skin Perfusion After Nipple-Sparing Mastectomy by Indocyanine Green Dye" *Journal of Saitama Medical University*, Japan, 32(2):45-50, (With English Abstract).

Yoneya, S. et al. (Jun. 1998). "Binding Properties of Indocyanine Green in Human Blood," *IOVS* 39(7):1286-1290.

Yoneya, S. et al. (Sep. 1993). "Improved Visualization of the Choroidal Circulation with Indocyanine Green Angiography," *Arch Opthalmol.* 111(9):1165-1166.

Young. I.T. et al. (1993). "Depth of Focus in Microscopy," SCIA '93, Proc. of the 8th Scandinavian Conference on Image Analysis, Tromso, Norway, pp. 493-498, six pages.

Canadian Office Action dated Mar. 16, 2016, for CA Application No. 2,750,760 filed on Jan. 23, 2009, five pages.

Canadian Office Action dated Oct. 25, 2016 for Canadian Patent Application No. 2,811,847, filed on Sep. 20, 2011, three pages.

Canadian Office Action dated Sep. 30, 2015, for CA Application No. 2,811,847, filed on Sep. 20, 2011, four pages.

Chinese Office Action dated Jul. 3, 2012, issued in counterpart Chinese Application No. 200980123414.0—(with English Translation).

Chinese Office Action dated May 23, 2013, issued in counterpart Chinese Application No. 200980123414.0—(with English Translation).

Chinese Office Action dated Nov. 12, 2015, for Chinese Patent Application No. 201180057244.8, filed on Sep. 20, 2010, eight pages, (with English Translation).

Chinese Third Office Action dated Aug. 8, 2016 for Chinese Application No. 201180057244.8 filed on Sep. 20, 2011, eighteen pages, (with English Translation).

EP Communication in pursuant to Article 94(3) EPC dated Mar. 9, 2016 for European Patent Application No. 09739980.2 filed on May 1, 2009, five pages.

European Communication pursuant to Article 94(3) dated May 27, 2016 for EP Application No. 15160177.0 filed on Aug. 11, 2000, five pages.

European Communication pursuant to Rules 70(2) and 70a(2) EPC in EP Application No. 09732993.2 dated May 15, 2014.

European Decision in Opposition Proceeding Revoking (Jun. 10, 2010). European Patent No. 1 143 852, thirty pages.

European Notice of Allowance dated Oct. 21, 2015, for EP Application No. 11 826 475.3, filed on Sep. 20, 2010, eight pages.

European Notice of Allowance dated Oct. 29, 2015, for EP Application No. 09 704 642.9, filed on Jan. 25, 2008, two pages.

European Office Action dated Mar. 27, 2015, for EP Application No. 09 732 993.2, filed on Apr. 14, 2008, six pages.

European Opposition of European Patent No. EP1143852 lodged by Hamamatsu Photonics, Inc., Jul. 30, 2008.

European Summons to attend Oral Proceedings pursuant to Rule 115(1) EPC dated Apr. 25, 2016, for European patent application No. 09732993.2, filed Apr. 14, 2009, 5 pages.

Extended European Search Report dated Oct. 14, 2015 for EP Application No. 13806313.6 filed on Jun. 20, 2013, nine pages.

Extended European Search Report dated Apr. 28, 2014, for EP Application No. 09 732 993.2, filed on Apr. 14, 2008, eight pages.

Extended European Search Report dated Feb. 22, 2012, for EP Application No. 09 704 642.9, filed on Jan. 25, 2008, fifteen pages.

Extended European Search Report dated Jan. 28, 2014, for EP Application No. 11 826 475.3, filed on Sep. 20, 2010, six pages.

Final Office Action dated Apr. 10, 2008, for U.S. Appl. No. 11/106,154, filed Apr. 14, 2005, six pages.

Final Office Action dated Apr. 2, 2013, for U.S. Appl. No. 13/419,368, filed Mar. 13, 2012, five pages.

Final Office Action dated Apr. 20, 2016, for U.S. Appl. No. 14/543,429, filed Nov. 17, 2014, seven pages.

Final Office Action dated Apr. 27, 2011 for U.S. Appl. No. 11/515,419, filed Sep. 1, 2006, nine pages.

Final Office Action dated Aug. 10, 2012, for U.S. Appl. No. 11/912,877, filed Aug. 13, 2008, ten pages.

Final Office Action dated Dec. 4, 2014, for U.S. Appl. No. 12/776,835, filed May 10, 2010, thirteen pages.

Final Office Action dated Feb. 1, 2013, for U.S. Appl. No. 12/776,835, filed May 10, 2010, thirteen pages.

Final Office Action dated Feb. 13, 2015, for U.S. Appl. No. 14/543,429, filed Nov. 17, 2014, six pages.

Final Office Action dated Feb. 18, 2010, for U.S. Appl. No. 11/106,154, filed Apr. 14, 2005, six pages.

Final Office Action dated Feb. 4, 2015 for U.S. Appl. No. 13/314,418, filed Dec. 8, 2011, six pages.

Final Office Action dated Jul. 21, 2016 for U.S. Appl. No. 14/543,356, filed Nov. 17, 2014, seven pages.

(56) References Cited

OTHER PUBLICATIONS

Final Office Action dated Jul. 9, 2015, for U.S. Appl. No. 14/543,356, filed Nov. 17, 2014, eight pages.
Final Office Action dated Jun. 1, 2015, for U.S. Appl. No. 14/543,429, filed Nov. 17, 2014, nine pages.
Final Office Action dated Jun. 13, 2014, for U.S. Appl. No. 12/776,835, filed May 10, 2010, thirteen pages.
Final Office Action dated Jun. 25, 2014, for U.S. Appl. No. 12/933,477, filed Sep. 20, 2010, fifteen pages.
Final Office Action dated Mar. 28, 2013 for U.S. Appl. No. 12/063,349, filed May 12, 2010, twenty pages.
Final Office Action dated May 29, 2013, for U.S. Appl. No. 12/933,477, filed Sep. 20, 2010, twelve pages.
Final Office Action dated Nov. 6, 2013, for U.S. Appl. No. 13/419,368, filed Mar. 13, 2012, five pages.
Final Office Action dated Oct. 7, 2011 for U.S. Appl. No. 11/851,312, filed Sep. 6, 2007, ten pages.
Final Office Action dated Sep. 13, 2011, for U.S. Appl. No. 11/106,154, filed Apr. 14, 2005, five pages.
Final Office Action dated Sep. 17, 2014 for U.S. Appl. No. 11/515,419, filed Sep. 1, 2006, eleven pages.
Final Office Action dated Sep. 17, 2015, for U.S. Appl. No. 12/933,477, filed Sep. 20, 2010, six pages.
Final Office Action dated Sep. 23, 2004, for U.S. Appl. No. 09/744,034, filed Apr. 27, 2001, seven pages.
Final Office Action dated Sep. 29, 2016, for U.S. Appl. No. 13/922,996, filed Jun. 20, 2013, fourteen pages.
Indian Examination Report dated Sep. 22, 2016 for Indian Application No. 7566/DELNP/2010, filed Oct. 27, 2010, nine pages.
International Preliminary Examination Report completed on Jul. 1, 2001 for PCT/US00/22088, filed Aug. 11, 2000, three pages.
International Search Report and Written Opinion dated Jul. 29, 2009 for PCT/US2009/043975 filed on May 14, 2009, eleven pages.
International Search Report for Application No. PCT/EP2008/008547, dated Jun. 2, 2009; six pages.
International Search Report dated Dec. 3, 2015 for PCT Application No. PCT/CA2015/050973 filed on Sep. 28, 2015, three pages.
International Search Report dated Dec. 3, 2009, for PCT Patent Application No. PCT/IB2009/005700, filed on Apr. 14, 2009, three pages.
International Search Report dated Feb. 1, 2012, for PCT Patent Application No. PCT/IB2011/002381, filed on Sep. 20, 2011, five pages.
International Search Report dated Jan. 22, 2014, for PCT Application No. PCT/IB2013/001934, filed on Jun. 20, 2013, four pages.
International Search Report dated Jun. 8, 2009, for PCT Patent Application No. PCT/CA2009/000073, filed on Jan. 23, 2009, three pages.
International Search Report dated Oct. 18, 2000, for PCT Application No. PCT/US2000/22088, filed on Aug. 11, 2000, one page.
Japanese First Office Action dated Feb. 1, 2016 for Japanese Patent Application No. 2015-517876 filed on Jun. 20, 2013, eight pages, (with English Translation).
Japanese Notice of Allowance dated Sep. 16, 2016, for Japanese Patient Application No. 2015-517876 filed on Jun. 20, 2013, six pages, (with English Translation).
Japanese Office Action dated Jul. 30, 2013, issued in counterpart Japanese Application No. 2011-504574, filed on Apr. 14, 2009 six pages, (with English Translation).
Japanese Office Action dated Apr. 1, 2016, for Japanese Patent Application No. 2013-529729, filed on Mar. 21, 2013, seven pages, (with English Translation).
Japanese Office Action dated Sep. 14, 2015, for Japanese Patent Application No. 2011-504574, filed on Apr. 14, 2009, five pages, (with English Translation).
Korean Notice of Allowance dated Apr. 29, 2016, for Korean Patent Application No. 10-2010-7024977, filed on Apr. 14, 2009, three pages, (with English Translation).
Korean Office Action dated Nov. 30, 2015, for Korean Patent Application No. 10-2010-7024977, filed on Apr. 14, 2009, five pages, (with English Translation).
Korean Patent Office, Office Action dated Jun. 25, 2014 in Korean Patent Application No. 10-2013-7035027, filed on May 14, 2009, fifteen pages, (with English Translation).
Non-Final Office Action dated Apr. 1, 2015, for U.S. Appl. No. 12/933,477, filed Sep. 20, 2010, fourteen pages.
Non-Final Office Action dated Apr. 26, 2012, for U.S. Appl. No. 12/776,835, filed May 10, 2010, nine pages.
Non-Final Office Action dated Apr. 28, 2010, for U.S. Appl. No. 11/946,672, filed Nov. 28, 2007, nine pages.
Non-Final Office Action dated Aug. 29, 2014 for U.S. Appl. No. 12/063,349, filed May 12, 2010, nineteen pages.
Non-Final Office Action dated Dec. 20, 2013, for U.S. Appl. No. 12/933,477, filed Sep. 20, 2010, thirteen pages.
Non-Final Office Action dated Dec. 30, 2010, for U.S. Appl. No. 11/106,154, filed Apr. 14, 2005, six pages.
Non-Final Office Action dated Feb. 1, 2011 for U.S. Appl. No. 11/851,312, filed Sep. 6, 2007, seven pages.
Non-Final Office Action dated Feb. 5, 2016, for U.S. Appl. No. 14/543,356, filed Nov. 17, 2014, seven pages.
Non-Final Office Action dated Jan. 22, 2014, for U.S. Appl. No. 11/851,312, filed Sep. 6, 2007, ten pages.
Non-Final Office Action dated Jan. 27, 2012, for U.S. Appl. No. 11/912,877, filed Aug. 13, 2008, eleven pages.
Non-Final Office Action dated Jan. 9, 2009, for U.S. Appl. No. 11/106,154, filed Apr. 14, 2005, six pages.
Non-Final Office Action dated Jul. 22, 2015 for U.S. Appl. No. 13/314,418, filed Dec. 8, 2011, six pages.
Non-Final Office Action dated Jul. 8, 2014 for U.S. Appl. No. 13/314,418, filed Dec. 8, 2011, seven pages.
Non-Final Office Action dated Jun. 11, 2013 for U.S. Appl. No. 11/515,419, filed Sep. 1, 2006, eleven pages.
Non-Final Office Action dated Jun. 28, 2012 for U.S. Appl. No. 12/063,349, filed May 12, 2010, seventeen pages.
Non-Final Office Action dated Mar. 10, 2004, for U.S. Appl. No. 09/744,034, filed Apr. 27, 2001, seven pages.
Non-Final Office Action dated Mar. 13, 2015, for U.S. Appl. No. 14/543,356, filed Nov. 17, 2014, eight pages.
Non-Final Office Action dated Mar. 6, 2007, for U.S. Appl. No. 11/106,154, filed Apr. 14, 2005, eight pages.
Non-Final Office Action dated May 21, 2015, for U.S. Appl. No. 13/922,996, filed Jun. 20, 2013, fourteen pages.
Non-Final Office Action dated May 6, 2015 for U.S. Appl. No. 12/063,349, filed May 12, 2010, seventeen pages.
Non-Final Office Action dated Nov. 27, 2015, for U.S. Appl. No. 14/543,429, filed Nov. 17, 2014, six pages.
Non-Final Office Action dated Nov. 9, 2015, for U.S. Appl. No. 14/177,045, filed Feb. 10, 2014, seven pages.
Non-Final Office Action dated Oct. 12, 2016, for U.S. Appl. No. 14/543,429, filed Nov. 17, 2014, nine pages.
Non-Final Office Action dated Oct. 28, 2016, for U.S. Appl. No. 14/543,356, filed Nov. 17, 2014, eight pages.
Non-Final Office Action dated Oct. 3, 2013, for U.S. Appl. No. 12/776,835, filed May 10, 2010, twelve pages.
Non-Final Office Action dated Sep. 15, 2010, for U.S. Appl. No. 11/106,154, filed Apr. 14, 2005, six pages.
Non-Final Office Action dated Sep. 30, 2010 for U.S. Appl. No. 11/515,419, filed Sep. 1, 2006, eleven pages.
Non-Final Office Action dated Sep. 5, 2012, for U.S. Appl. No. 12/933,477, filed Sep. 20, 2010, seven pages.
Notice of Allowance dated Apr. 17, 2014, for U.S. Appl. No. 13/419,368, filed Mar. 13, 2012, five pages.
Notice of Allowance dated Aug. 7, 2014, for U.S. Appl. No. 13/850,063, filed Mar. 25, 2013, nine pages.
Notice of Allowance dated Jul. 13, 2016, for U.S. Appl. No. 14/598,832, filed Jan. 16, 2015, seven pages.
Notice of Allowance dated Mar. 15, 2016, for U.S. Appl. No. 14/598,832, filed Jan. 16, 2015, seven pages.
Notice of Allowance dated Mar. 7, 2005, for U.S. Appl. No. 09/744,034, filed Apr. 27, 2001, five pages.

(56) References Cited

OTHER PUBLICATIONS

Notice of Allowance dated May 26, 2016, for U.S. Appl. No. 14/177,045, filed Feb. 10, 2014, eight pages.
Notice of Allowance dated Nov. 25, 2015, for U.S. Appl. No. 14/598,832, filed Jan. 16, 2015, seven pages.
Notice of Allowance dated Nov. 30, 2010, for U.S. Appl. No. 11/946,672, filed Nov. 28, 2007, six pages.
Notice of Allowance dated Oct. 16, 2014, for U.S. Appl. No. 13/850,063, filed Mar. 25, 2013, eight pages.
Notice of Allowance dated Oct. 18, 2012, for U.S. Appl. No. 12/841,659, filed Jul. 22, 2010, seven pages.
Notice of Allowance dated Oct. 4, 2013, for U.S. Appl. No. 11/912,877, filed Aug. 13, 2008, nine pages.
Notice of Allowance dated Oct. 6, 2014, for U.S. Appl. No. 13/419,368, filed Mar. 13, 2012, five pages.
Notification of Transmittal of International Search Report and the Written Opinion of the International Searching Authority, or the Declaration dated Apr. 3, 2008 for PCT/US07/77892, filed on Sep. 7, 2007, ten pages.
Partial European Search Report dated Dec. 16, 2010 for European Application No. 10186218.3 filed on Aug. 11, 2000, seven pages.
Russian Decision on Grant dated Jul. 29, 2013, issued in counterpart Russian Application No. 2011111078.14, five pages, (with English Translation).
Russian Office Action dated Mar. 29, 2013, issued in counterpart Russian Application No. 2011111078.14, filed on three pages, (with English Translation).
Supplemental European Search Report dated Jul. 6, 2004 for EP Application No. 00955472.6, five pages.
Written Opinion for Application No. PCT/EP2008/008547, dated Jun. 2, 2009; eleven pages.
Written Opinion of the International Searching Authority dated Dec. 3, 2009, for PCT Patent Application No. PCT/IB2009/005700, filed on Apr. 14, 2009, six pages.
Written Opinion of the International Searching Authority dated Feb. 1, 2012, for PCT Patent Application No. PCT/IB2011/002381, filed on Sep. 20, 2011, four pages.
Written Opinion of the International Searching Authority dated Jan. 22, 2014, for PCT Application No. PCT/IB2013/001934, filed on Jun. 20, 2013, six pages.
Written Opinion of the International Searching Authority dated Jun. 8, 2009, for PCT Patent Application No. PCT/CA2009/000073, filed on Jan. 23, 2009, four pages.
Mexican Office Action dated May 30, 2013, issued in counterpart Mexican Application No. MX/a/2010/011249, no translation.
Declaration of Brian Wilson dated Aug. 22, 2017 for Inter Partes Review No. IPR2017-01426, twelve pages, [Exhibit 2002].
Definition of "Expose," Excerpt of Merriam Webster's Medical Desk Dictionary (1993), four pages, [Exhibit 2004].
Definition of "Graft," Excerpt of Stedman's Medical Dictionary for the Health Professions and Nursing; 6th Ed. (2008), three pages, [Exhibit 2003].
Enquist, L.W. et al. (2002). "Directional Spread of an α-Herpesvirus in the Nervous System," *Veterinary Microbiology* 86:5-16.
Falk, T. et al. (Apr. 15, 2001). "A Herpes Simplex Viral Vector Expressing Green Fluorescent Protein can be Used to Visualize Morphological Changes in High-density Neuronal Culture," *Electronic Journal of Biotechnology* 4(1):34-45.
Hyvärinen, L. et al. (1980). "Indocyanine Green Fluorescence Angiography." *Acta Ophthalmologica* 58(4):528-538. [Exhibit 1014].
Joseph, S. et al. (Mar. 1999). "Evaluation of the Circulation of Reconstructive Flaps Using Laser-induced Fluorescence of Indocyanine Green," *Annals of Plastic Surgery* 42(3):266-274. [Exhibit 1016].
Little, J.R. et al. (1979). "Superficial Temporal Artery to Middle Cerebral Artery Anastomosis: Intraoperative Evaluation by Fluorescein Angiography and Xenon-133 Clearance," *Journal of Neurosurgery* 50(5):560-569. [Exhibit 1002].

Novadaq Technologies Inc. (Jan. 19, 2005). 510(k) Summary—Showing X-Ray Fluoroscopy as Predicate Device, Fluorescent Angiographic System, six pages, [Exhibit 1012].
Canadian Notice of Allowance dated Jan. 4, 2018, for Canadian Application No. 2,750,760, filed on Jul. 25, 2008, one page.
Canadian Notice of Allowance dated Sep. 27, 2017, for Canadian Application No. 2,811,847, filed on Mar. 20, 2013, one page.
Canadian Office Action dated Feb. 27, 2017 for Canadian Application No. 2,750,760, filed on Jul. 25, 2011, three pages.
Canadian Office Action dated Jan. 19, 2017 for Canadian Application No. 2,914,778 filed on Dec. 8, 2015, four pages.
Canadian Office Action dated Nov. 28, 2017 for Canadian Application No. 2,914,778 filed on Dec. 8, 2015, six pages.
Chinese Fifth Office Action dated Dec. 19, 2017 for Chinese Application No. 201180057244.8 filed on Sep. 20, 2011, eleven pages.
Chinese First Office Action dated Apr. 6, 2017 for Chinese Application No. 201510214021.8, filed on May 14, 2009, fifteen pages.
Chinese Fourth Office Action dated Mar. 13, 2017 for Chinese Application No. 201180057244.8 filed on Sep. 20, 2011, twenty pages.
European Communication Pursuant to Article 94(3) EPC dated Aug. 31, 2017, for EP Application No. 09739980.2 filed on Nov. 30, 2010, four pages.
European Communication pursuant to Rules 70(2) and 70a(2) EPC in EP Application No. 16163909.1, dated Nov. 14, 2016, two pages.
European Communication Under Rule 71(3) EPC (Intention to Grant) dated Dec. 1, 2017, for European patent Application No. 09739980.2, filed on Nov. 30, 2010, seven pages.
European Communication under Rule 71(3) EPC (Intention to Grant) dated Nov. 21, 2017, for European Patent Application No. 15160177.0, filed on Aug. 11, 2000, seven pages.
European Decision of European Patent Office Technical Board of Appeal Revoking Counterpart Patent No. 1143852, dated Oct. 23, 2013. [Exhibit-1009].
European Decision to Grant dated Apr. 21, 2017 for EP Application No. 09732993.2, filed on Nov. 8, 2010, two pages.
European Summons to attend Oral Proceedings pursuant to Rule 115(1) EPC dated Dec. 16, 2016, for European patent application No. 15160177.0, filed on Aug. 11, 2000, seven pages.
Extended European Search report dated Sep. 16, 2016 for EP Application No. 16183434.6 filed on Aug. 9, 2016, ten pages.
Indian Examination Report dated Jul. 28, 2017 for Indian Application No. 1983/MUMNP/2007, filed on Nov. 27, 2007, seven pages.
International Preliminary Report on Patentability dated Apr. 4, 2017, for PCT Application No. PCT/CA2015/050973 filed on Sep. 28, 2015, six pages.
International Search Report and Written Opinion dated Oct. 24, 2017 for PCT Application No. PCT/CA2017/050564 filed on May 10, 2017, fourteen pages.
International Search report dated Jul. 4, 2008 for International Application No. PCT/US2007/080847, filed on Oct. 9, 2007, three pages.
Invitation to Pay Additional Fees and, Where Applicable, Protest Fee dated Jul. 4, 2017, for PCT/CA2017/050564, filed on May 10, 2017, two pages.
Japanese First Office Action dated Jul. 28, 2017 for Japanese Patent Application No. 2016-203798 filed on Oct. 17, 2016, four pages, (with English Translation).
Japanese Notice of Allowance dated Sep. 25, 2017 for Japanese Patent Application No. 2013-529729, filed on Mar. 21, 2013, six pages.
Japanese Office Action dated Mar. 3, 2017, for Japanese Patent Application No. 2016-014503, filed on Jan. 28, 2016, ten pages.
Japanese Office Action dated Mar. 31, 2017 for Japanese Patent Application No. 2013-529729, filed on Mar. 21, 2013, eleven pages.
Korean Notice of Allowance dated Apr. 27, 2017, for Korean Patent Application No. 10-2016-7007994, filed on Mar. 25, 2016, three pages.
Novadaq Technologies Inc.'s Preliminary Response filed on Aug. 23, 2017 to Petition for Inter Partes Review of U.S. Pat. No. 8,892, sixty one pages.

(56) References Cited

OTHER PUBLICATIONS

Partial European Search Report dated Jun. 28, 2016 for European Application No. 16163909.1 filed on Apr. 5, 2016, six pages.
Petition for Inter Partes Review of U.S. Pat. No. 8,892, (May 11, 2017), filed by Visionsense Corp., fifty four pages.
U.S. Final Office Action dated Apr. 12, 2017, for U.S. Appl. No. 14/543,429, filed Nov. 17, 2014, nine pages.
U.S. Final Office Action dated Apr. 4, 2017, for U.S. Appl. No. 12/933,477, filed Sep. 20, 2010, twelve pages.
U.S. Non-Final Office Action dated Dec. 16, 2016, for U.S. Appl. No. 14/868,369, filed Sep. 28, 2015, seven pages.
U.S. Non-Final Office Action dated Jan. 8, 2018, for U.S. Appl. No. 15/077,677, filed Mar. 22, 2016, nine pages.
U.S. Non-Final Office Action dated Nov. 18, 2016, for U.S. Appl. No. 12/933,477, filed Sep. 20, 2010, six pages.
U.S. Non-Final Office Action dated Oct. 13, 2017, for U.S. Appl. No. 13/922,996, filed Jun. 20, 2013, seventeen pages.
U.S. Non-Final Office Action dated Oct. 26, 2017, for U.S. Appl. No. 14/543,429, filed Nov. 17, 2014, nine pages.
U.S. Notice of Allowance dated Dec. 2, 2016, for U.S. Appl. No. 14/598,832, filed Jan. 16, 2015, seven pages.
U.S. Notice of Allowance dated Dec. 6, 2017, for U.S. Appl. No. 15/476,290, filed Mar. 31, 2017, nine pages.
U.S. Notice of Allowance dated Jul. 12, 2017, for U.S. Appl. No. 14/868,369, filed Sep. 28, 2015, nine pages.
U.S. Restriction Requirement dated Jun. 26, 2017, for U.S. Appl. No. 15/077,677, filed Mar. 22, 2016, seven pages.
Written Opinion of the International Searching Authority dated Jul. 4, 2008 for International Application No. PCT/US2007/080847, filed Oct. 9, 2007, six pages.
Written Opinion of the International Searching Authority dated Dec. 3, 2015 for PCT Application No. PCT/CA2015/050973 filed on Sep. 28, 2015, five pages.
U.S. Appl. No. 15/591,909, filed May 10, 2017, by Moore et al.

\* cited by examiner

METHODS FOR PRODUCTION AND USE OF SUBSTANCE-LOADED ERYTHROCYTES (S-IES) FOR OBSERVATION AND TREATMENT OF MICROVASCULAR HEMODYNAMICS

RELATED APPLICATIONS

This application is a continuation of U.S. patent application Ser. No. 12/917,849, filed Nov. 2, 2010, which is a continuation-in-part of PCT App. No. PCT/US2009/042606, filed May 1, 2009, which claims the benefit of priority under 35 U.S.C. § 119(e) to U.S. Prov. App. No. 61/126,344, filed May 2, 2008, the disclosures of which are incorporated herein by reference.

FIELD OF THE INVENTION

Disclosed herein are kits, compositions, and methods for the clinical use of erythrocytes in the fields of medical angiography and therapy. The erythrocytes have been preloaded with substances for observation of blood flow under physiological conditions to detect circulation abnormalities. The erythrocytes may also be used for delivery of therapeutic substances to localized vascular areas. This technology can be applied to any vasculature that can be directly visualized by an optical means, such as ocular vasculatures.

BACKGROUND

Medical angiographic imaging typically involves administration of a detectable substance to a subject (see U.S. Pat. No. 6,915,154). In some instances the detectable substance may also be a therapeutic agent (see U.S. Patent Publication No. 2004/0206364). Most often the detectable substance is administered directly to a subject by intravascular injection, in which case the detectable substance mixes with and is carried through the vasculature by plasma, along with the blood cells. When using conventional angiography methodology, wherein the detectable substance is a liquid dye, blood flow physiology is treated too simplistically, especially at the microvascular level (i.e., the arterioles, capillaries, and venules).

Blood is a shear-thinning, non-Newtonian fluid. However, in diagnostic applications, blood often is treated as if it were water-like (i.e., a Newtonian fluid), and not an homogeneous mixture of two distinctly different non-Newtonian fluids: (1) liquid (plasma) and (2) particles (blood cells, especially erythrocytes). Limitations inherent in conventional angiography contribute to ignoring that the dynamics of plasma movement do not necessarily reflect the dynamics of erythrocyte movement, especially at the microvascular level where their movement is far more important to the circulation's metabolic efficiency than that of plasma. For example, in conventional sodium fluorescein and indocyanine green angiography (SFA and ICGA) of the ocular vasculatures, observed fluorescence arises from dye molecules associated primarily with blood plasma, not erythrocytes. Even in capillaries, where they deform in order to pass through one-at-a-time in boxcar fashion, erythrocytes cannot be seen in conventional angiogram images, so metabolically significant phenomena such as vasomotion, which results in periodic suspension of erythrocyte movement through individual capillaries, cannot be directly visualized. Yet, it has been postulated that all the clinical findings concerning edema in diabetic maculopathy can be explained as a result of disturbances in retinal vasomotion (Bek 1999, *Acta Ophthalmol Scand* 77:376). Moreover, in conventional angiography, dye molecules leave the plasma and become associated with vessel walls, so those blood vessels rapidly exhibit steady-state fluorescence, thereby obscuring further visualization of blood movement. Consequently, conventional fluorescent dye angiography is limited as a diagnostic tool, since what hemodynamic information it conveys is misleading with respect to metabolic efficiency and capacity of microvascular blood flow. An example of this would be relying on observation of conventional angiograms to assay the metabolic capacity of blood flow through a choroidal neovascular (CNV) membrane. Due to the well-known phenomenon of plasma skimming (likely to occur where the CNV feeder vessel arises at an acute angle from the choroidal arterial vessel feeding it), only erythrocyte-deficient plasma would profuse the CNV, but this deficiency would not be reflected in the angiogram images since the fluorescence arises only from dye in the plasma, not the erythrocytes.

Alternatively, a detectable substance (e.g., sodium fluorescein dye) has been administered in a particle carrier, heat sensitive liposomes (Kiryu et al. 1994, *Invest Opthalmol Vis Sci* 35:3724). However, such artificial particles are rigid and are small to assure that they can pass unobstructed through the smallest capillary vessels. They may not serve as faithful models of erythrocyte dynamics.

SUMMARY OF THE INVENTION

Disclosed herein are kits, compositions, and methods that take advantage of the ability of erythrocytes to be preloaded with various substances, such as fluorescent dyes that facilitate medical imaging. Human erythrocytes, despite their large diameters and volumes, readily conform to the small capillary diameters, and they have been demonstrated to possess properties that make them useful as carriers of molecules other than haemoglobin. Erythrocytes are capable of reversible deformation, such as occurs when they are in hypotonic solution; their volumes increase, causing 200-500 Å pores to open transiently in the cells' membranes (Seeman, 1967, *J Cell Biology* 32:55), allowing two-way transmembrane exchange between their normal content (haemoglobin) and high-molecular-weight substances placed in their externally vicinity. Then, by returning the solution to normotonicity, the pores close, and the cells return to normal size, trapping the added substances inside; remaining non-entrapped substance can be washed away, leaving substance-loaded osmotically competent erythrocytes; these cells contain reduced amounts of hemoglobin, rendering them incompetent—or at least inefficient—with regard to oxygen delivery. Nevertheless, substance-loaded erythrocytes (S-IEs) appear to have a normal life span of up to 120 days, and they have been used for studying membrane morphology, physiology and biochemistry (see, e.g., Wu et al., 2005, *Biochem Pharmacol* 69(8): 1257; Rodnenkov et al., 2005, *Pathophysiology* 11(4):209). S-IEs have been used in the field of medical imaging (see, e.g., Thelwall et al., 2002, *Magnetic Resonance in Medicine* 48:649; Kleszcynska et al., *J. Flouresc.* 15(2):137).

One embodiment relates to the discovery that the amount of ICG dye inserted into each erythrocyte can produce detectable fluorescence without exceeding safe levels of retinal illumination. Another embodiment relates to the discovery that the amount needed to optimally induce fluorescence and the much larger amount needed to absorb sufficient energy to enhance photocoagulation are mutually exclusive. Yet another embodiment relates to the re-sealing of the cells of the substance-loaded erythrocytes.

One embodiment provides freeze-dried or lyophilized compositions comprising at least one fluorescent dye entrapped within erythrocytes. In one embodiment, this composition is formed from the method comprising:
(a) providing erythrocytes in a blood anti-coagulant solution;
(b) reducing the osmolality of the erythrocyte-containing solution in (a) by dialysis against a dialysis buffer having an osmolality less than 300 mOsm/kg to cause pores in the erythrocyte to open and form a dialyzed solution;
(c) combining the dialyzed solution in (b) with at least one fluorescent dye;
(d) combining the dye-containing solution in (c) with a resealing solution having an osmolality of at least 1000 mOsm/kg to increase the osmolality, thereby causing the erythrocyte pores to close and entrap the at least one fluorescent dye within the erythrocytes;
e) washing the erythrocytes in an isotonic saline washing solution containing glucose or trehalose to remove extracellular dye; and
(f) freezing or freeze-drying, the entrapped dye.

In one embodiment, the dialysis buffer is water. In another embodiment, the method further comprising introducing at least one saccharide prior to (d), where the at least one saccharide is selected from mannose, xylose, glucose, trehalose, sucrose and maltose.

One embodiment provides a method comprising:
(a) providing erythrocytes in a blood anti-coagulant solution;
(b) dialyzing the erythrocyte-containing solution in (a) against a dialysis buffer having an osmolality ranging from 50-70 mOsm/kg to cause pores in the erythrocyte to open and form a dialyzed solution;
(c) combining the dialyzed solution in (b) with at least one fluorescent dye;
(d) combining the dye-containing solution in (c) with a resealing solution having an osmolality of at least 1000 mOsm/kg to increase the osmolality, thereby causing the erythrocyte pores to close and entrap the at least one fluorescent dye within the erythrocytes;
e) washing the erythrocytes in an isotonic saline washing solution containing glucose or trehalose to remove extracellular dye; and
(f) freezing or freeze-drying, the entrapped dye.

Use of erythrocytes as a drug delivery system has been investigated (see, e.g., Rossi et al. 2001, *Biotechnol Appl Biochem* 33:85; Magnani et al., 1998, *Biotechnol Appl Biochem* 28:1). In the method disclosed, erythrocytes that had been loaded with various therapeutic substances were autologously re-injected into a subject and were subsequently distributed throughout the body; there they continuously released the encapsulated substance as the erythrocyte population gradually underwent normal cell death over a span of about 120 days. Although useful for delivery of certain drugs where maintenance of some level of substance throughout the circulation is desirable, this method does not readily facilitate targeted release of therapeutic substances in high concentration. Therefore, its use for delivery of substances to targeted vascular areas requiring therapeutic concentrations too high to be tolerated throughout the body may be prohibited. Another embodiment relates to the discovery that in situations where the targeted vascular area is optically accessible (e.g., the ocular vasculatures or the vasculatures of hollow organs such as the bladder), erythrocytes loaded with appropriate substances can be lysed by means of optical delivery of appropriate radiation, thereby delivering their entrapped contents to precisely localized areas.

Accordingly, another embodiment provides method for controlled release of a therapeutic agent, comprising:
(a) administering to a patient, a composition comprising erythrocytes having entrapped therein both the therapeutic agent and a fluorescent dye;
(b) applying radiation to a field of view of a vasculature of interest at a selected wavelength and power to cause the erythrocytes to fluoresce;
(c) applying an increased power level of the same fluorescence-stimulating radiation to a target vasculature area within the field of view, such that the increased power heats the erythrocytes due to absorption by the entrapped dye, causing them to lyse and release the entrapped therapeutic agent.

In one embodiment, a portion of the erythrocytes contain ICG at a concentration that maximizes fluorescence efficiency, and the remainder contains both the therapeutic agent and ICG at a dye concentration that enhances light absorption, rather than fluorescence.

Also disclosed herein are kits and methods for the relatively facile preparation of substance-loaded erythrocytes (S-IEs) for use in clinical application for autologous re-injection. Alternatively, pre-loaded erythrocytes suitable for homologous re-injection in an off-the-shelf form can be prepared. To that end, disclosed herein are methodologies for producing and stabilizing substance-loaded cells, for both diagnostic and therapeutic applications in human subjects, which can obviate need for end-user access to extensive laboratory facilities in order to obtain and process cells under blood-banking sterile conditions.

Another embodiment relates to the discovery that S-IEs having increased fluorescence (beyond that which can be achieved by optimal loading of dye alone into each erythrocyte) for cell detection can be achieved by incorporation of metallic silver colloids.

Another embodiment provides novel approaches to detection and controlled release of therapeutic substances encapsulated in S-IEs that result in delivery of high substance concentrations with respect to targeted vascular areas, but which at the same time amount to micro-dose concentrations with respect to the circulation as a whole; this makes possible use of substances that would otherwise be rejected due to the significant systemic toxicity they demonstrate when delivered by conventional intravenous injection. Various substances and combinations thereof can be pre-loaded into erythrocytes in ways that take into account a spectrum of desired biological, chemical, and physical properties of those elements in ways without which those combinations would not produce useful results.

One embodiment relates to the use of pre-loading substances into erythrocytes and use of S-IEs in ophthalmic diagnostic angiography and drug delivery. Alternatively, this technology can be applied to other vasculatures that can be directly visualized, as well as to other substances that facilitate similar ends in those other vasculatures.

BRIEF DESCRIPTION OF THE DRAWINGS

Various embodiments of the invention will be understood from the following description, the appended claims and the accompanying drawings, in which:

DETAILED DESCRIPTION

Preparation of Substance-Loaded Erythrocytes for Re-Injection

Figure 1A:
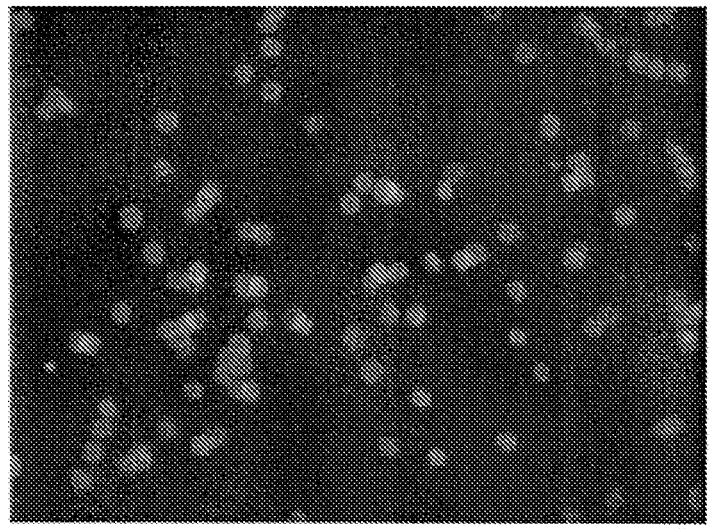
FIGS. 1A-1D are near-infrared fluorescence micrographs at 40× magnification of erythrocytes, comparing the brightness of cells "stained" with ICG (A—stained in 1 mM ICG solution for 30 min. and B—stained in 2 mM ICG solution for 60 min. to cells into which ICG has been loaded through pores in their membranes; C—stained plasma resulting from exposure for 20 min. to the stained erythrocytes from A; D—dialysed in 1 mM ICG solution for 30 min.)
Figure 1B:
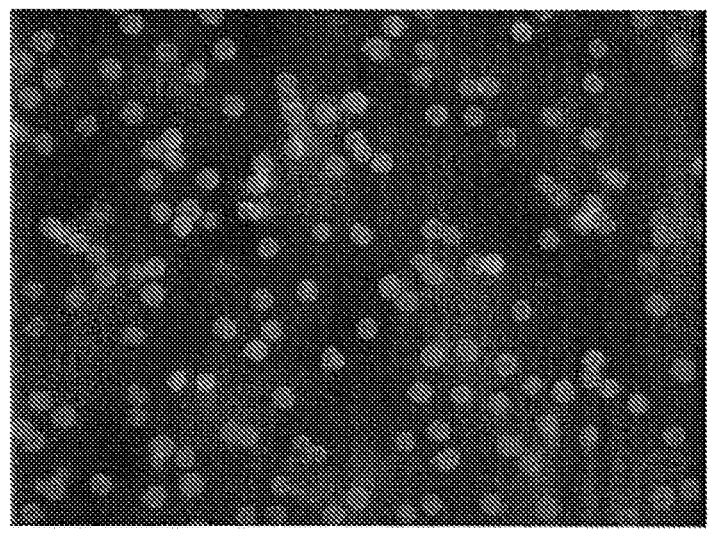
Figure 1C:
Figure 1D:
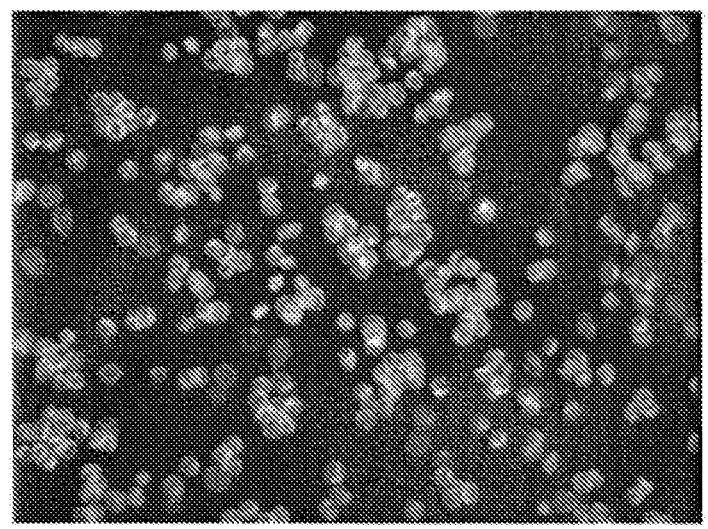
Figure 2A:
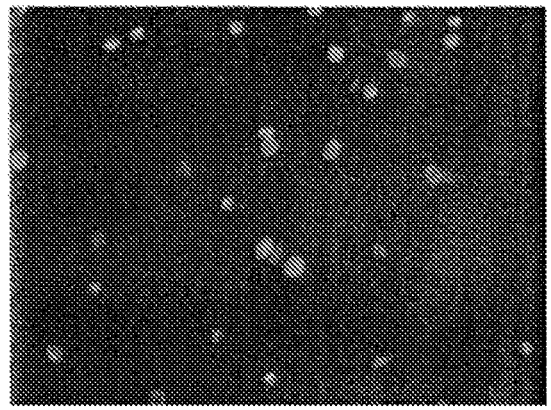
FIGS. 2A-C are near-infrared fluorescence micrographs at 40× magnification of erythrocytes into which ICG has been loaded, demonstrating the effect of introducing different dye concentrations into the dialyzed cell suspension.
Figure 2B:
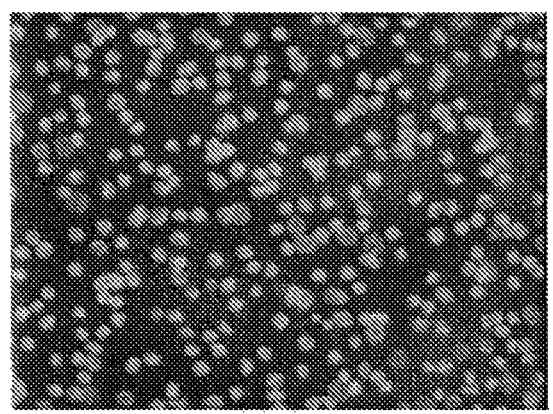
Figure 2C:
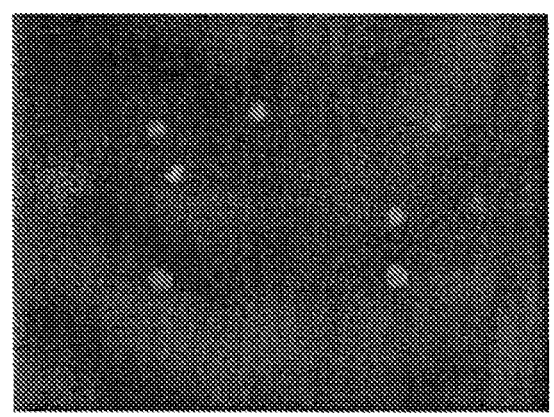
Figure 3A:
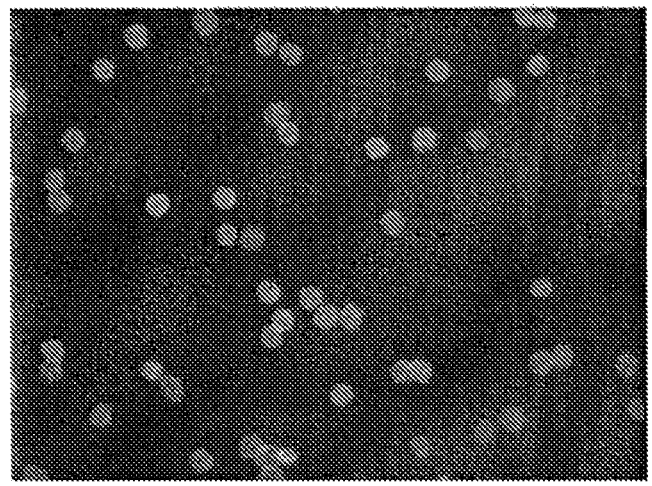
FIGS. 3A-3D are near-infrared fluorescence micrographs at 40× magnification comparing brightness of ICG-"stained" (A=initial brightness, B=brightness at 20 s) and ICG-loaded erythrocytes (C=initial brightness, D=brightness at 20 s) after continuous exposure to the same illumination, due to bleaching.
Figure 3B:
Figure 3C:
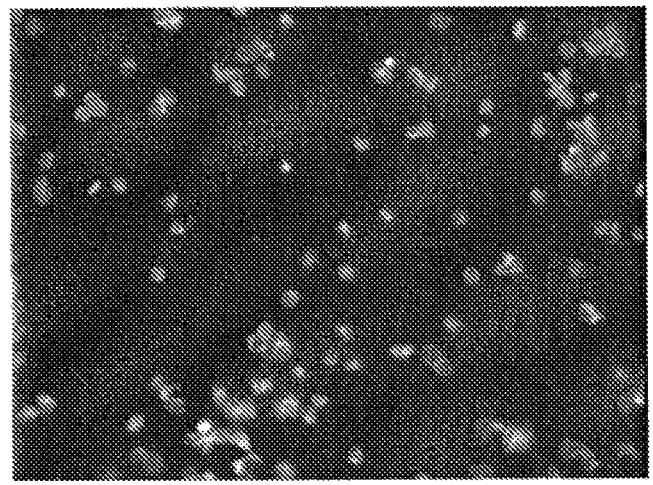
Figure 3D:
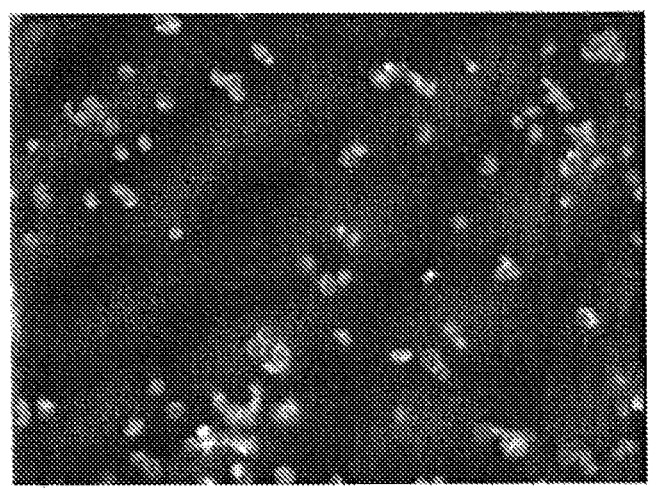

One embodiment relates to encapsulation of fluorescent dyes in erythrocytes for diagnostic observation. Optionally, the erythrocytes can be used for therapeutic substance delivery. In the former application, re-injection of S-IEs can improve performance of angiography by imaging movement of fluorescent erythrocytes, rather than dye-tagged plasma. In the latter application, the impetus for substance encapsulation in the cells is that many desirable substances do not bind well to the outer cell membrane (as is true for ICG dye). However, encapsulation of those substances in erythrocytes and localized release by laser-induced lysis facilitates delivery of high substance concentrations at the targeted areas, which amount only to micro-dose concentrations with respect to the circulation as a whole. This makes possible use of substances that otherwise may have had to be rejected. In the former application of diagnostic observation, the association of fluorescent dyes with erythrocytes may depend on one or more of three circumstances, each of which relates to why dye insertion into the cell rather than simply "staining" the outside of the cell is useful:

(1) Although many fluorescent dyes, such as ICG dye, do bind to the erythrocyte outer cell membrane, binding is weak and non-covalent, and regardless of the dye concentration and conjugation time, the maximum fluorescence brightness that can be achieved is considerably less than optimum (see FIG. 1). The erythrocytes in Frame B were "stained" by conjugation with ICG dye in a solution at twice the dye concentration and for twice as long as the cells in Frame A; yet the fluorescence brightness of both is the same since there only are a finite number of available cell-surface binding sites, regardless of the abundance of dye molecules in a particular solution. Frame C demonstrates that once "stained" cells come into contact with plasma proteins, ICG molecules are more attracted to plasma proteins than to the cell membrane, so "stained" cells become even less bright during circulation; this does not occur with dye-loaded cells. (2) Exposure to fluorescence excitation energy for diagnostic purposes must not exceed the safe maximum permissible exposure level for the sensory retina. Since ICG dye is a fairly weak emitter of fluorescence, care must be taken to ensure that the amount of ICG present post-loading is optimal, resulting in maximum fluorescence intensity possible at a given safe excitation energy level. This condition can be met by insertion of dye into the erythrocytes. FIG. 1, Frame D, demonstrates that ICG-loading of erythrocytes by dialysis in a dye solution having the same lower concentration used to stain the cells in Frame A. are considerably brighter; there are considerably more binding sites within a cell volume (including those associated with residual hemoglobin) than on its external surface. Moreover, since ICG is subject to concentration fluorescence quenching—even when inside erythrocytes—the amount of loaded dye must be controlled: too much or too little will not produce the maximum fluorescence. Equal brightness of cells in A and B demonstrates "staining" by conjugation in even high-concentration dye solution does not achieve the optimum brightness possible by dye insertion (D). Image C demonstrates that the affinity of ICG dye molecules is greater for plasma proteins than for the erythrocyte outer membrane; cells in A, B, and D are suspended in isotonic saline. Achieving optimal dye concentration is accomplished by controlling the amount of dye in the solution during dialysis once the pores in the cell membranes open; experimentation has determined the optimum amount to be approximately 1.0 µmol/mL dialysed cell-solution (see FIG. 2). After equilibrium is established between the solutions internal and external to the cells, the pores are closed by returning the hypotonic solution containing the cells to a normotonic level, fixing the entrapped dye concentration. This also has the advantage of preventing plasma dye-staining and the associated reduction of contrast between cell fluorescence and background brightness once the cells are re-injected. FIGS. 2A, 2B, and 2C have concentrations of 0.31 µmol/mL solution, 0.89 µmol/mL solution, and 6.14 µmol/mL solution giving rise to an average 8-bit-gray-scale brightness of 159, >255, and 165, respectively.

(3) ICG dye is subject to bleaching, potentially making detection and imaging of ICG-loaded erythrocytes difficult, due to the resulting reduced levels of fluorescence for a given level of illumination. This can be a problem, especially when it is desirable to make observations for periods of many seconds, as would be required for observing the effects on erythrocyte movement of vasomotion, wherein individual cell motion may be temporarily halted for up to 30 sec. It has been experimentally determined that, whereas ICG dye-"stained" cells are susceptible to bleaching, ICG-loaded cells are not (see FIG. 3). Again, it is the limited number of dye molecules on an erythrocyte's outer membrane, compared to the number within the cell volume that makes this phenomenon significantly visible in the "stained" cells, but not in the loaded cells.

In one embodiment, encapsulation of various substances in human erythrocytes is accomplished by a procedure of hypotonic dialysis, isotonic resealing and re-annealing. Placing washed erythrocytes in a hypotonic solution causes pores that can have a size ranging from 200-500 Å to open transiently in the cell membranes, thereby allowing substances (such as ICG dye) in the solution to cross the membranes. Making the hypotonic solution normotonic causes the pores close, and the cells (now with reduced hemoglobin content) return to an osmotically competent state, trapping the substances inside. Remaining un-entrapped substances can then be washed away, leaving only substance-loaded erythrocytes (S-IEs).

In one embodiment, the dye entrapping (or encapsulation) is as follows. Fresh blood in acid-citrate-dextrose anticoagulant is obtained under sterile conditions and centrifuged to obtain erythrocytes. These are then washed in a buffer to remove surface proteins, leukocytes and platelets and then centrifuging. The erythrocytes are then suspended at about 70% haematocrit (Ht) in the washing buffer solution inside a dialysis tube, where they are dialyzed against a dialysis buffer. ICG dye is then added to the dialyzed erythrocyte solution, and the mixture is incubated under gentle agitation. The erythrocytes (now with reduced hemoglobin content) are then resealed by returning the dialyzed erythrocyte solution to a normotonic state and incubating the cells. The resealed cells are washed several times and centrifuged each time. About 9 mL of whole blood yields 4 mL of packed (about 80% Ht) ICG-loaded erythrocytes. This same basic methodology has been elaborated to satisfy many approaches to providing S-IEs to be used in several different circumstances, but these approaches tend to be geared for laboratory implementation and do not, therefore, anticipate implementation in circumstances outside of a laboratory, wherein processing speed and maintenance of sterility are often critical. To overcome this shortcoming, disclosed herein are methods implementable by use of pre-prepared kits for ad hoc preparation of small volumes of substance-loaded erythrocyte ghost cells for autologous re-injection are possible. Modification and variations of such kits are possible. The kits as disclosed herein provide for such preparations in a manner that minimizes procedural steps, especially transfer of blood volumes, so that preparation can be made conveniently, quickly, and safely without access to extensive laboratory facilities.

1. Ad-Hoc Preparation of Small Volumes of S-IEs for Autologous Re-Injection:

One embodiment provides a method for an end-user who wants to use S-IEs for a specific subject, using the subject's own erythrocytes, or for introducing substances in a desired combination or concentration.

One embodiment provides method comprising:
(a) providing erythrocytes in a blood anti-coagulant solution;
(b) dialyzing the erythrocyte-containing solution in (a) against a dialysis buffer having an osmolality ranging from 50-70 mOsm/kg to cause pores in the erythrocyte to open;
(c) combining the dialyzed solution in (b) with at least one fluorescent dye; and
(d) combining the dye-containing solution in (c) with a resealing solution having an osmolality of at least 1000 mOsm/kg to increase the osmolality, thereby causing the erythrocyte pores to close and entrap the at least one fluorescent dye within the erythrocytes.

In one embodiment, the providing in step (a) comprises obtaining a blood sample from a subject.

In one embodiment, the dialyzed solution in (b) has an osmolality ranging from 80-90 mOsm/kg, e.g., an osmolality ranging from 85-87 mOsm/kg.

In one embodiment, the method further comprises washing the erythrocytes with an isotonic solution prior to the dialyzing in (b).

In one embodiment, the at least one fluorescent dye in (c) is indocyanine green dye having a concentration ranging from 0.25 to 3.0 µmoles/mL of dialyzed solution.

One embodiment provides a kit comprising:
a blood anti-coagulant;
a dialysis buffer having an osmolality ranging from 50-70 mOsm/kg;
a dialysis chamber;
at least one fluorescent dye; and
a resealing solution having an osmolality of at least 1000 mOsm/kg.

In one embodiment, the dialysis chamber has suspended from its top a dialysis tube with a molecular weight cut-off ranging from 12,000 to 14,000 Daltons. In one embodiment, the dialysis tube allows introduction of a blood-containing fluid into the tube, and a dialysis fluid can be introduced outside the suspended tube.

Small quantities of erythrocytes, such as would be needed for autologous re-injection into a single individual can be prepared under sterile conditions, using his own blood, in about 1.75 hours time. However, since laboratory sterile conditions are seldom conveniently available to locations where frequent diagnostic and therapeutic procedures are carried out, a convenient way to prepare or acquire the erythrocytes is a requirement if such procedures are to be broadly applied. One embodiment provides kits (one for each individual subject) each consisting of a series of disposable sterile containers, pre-loaded with appropriate amounts of chemicals. A freshly obtained volume of blood can be transferred, in sequence from one to another, until the substance-loading steps are completed (see FIGS. 9, 10, and 11). S-IEs prepared in this manner can be stored for use for several days at 4° C., until used.

A small refrigerator containing a small fixed-speed, fixed-time centrifuge can be used. The refrigerator space (accessible from its top, to keep the cold air reasonably contained) can be large enough to hold and pre-cool a kit and to provide a cool sterile workspace, as well as a place to temporarily store prepared S-IEs until used.

The advantage of this basic method of preparation is ad hoc introduction of substances or mixtures of substances (i.e., simultaneous introduction of two or more discrete substances, each at a different concentration). Also, autologous re-injection of a subject's cells assures that on contamination of incompatibility of human protein will be encountered. Although no further processing is required, so long as the cells are stored at proper temperature and that they are used within several days, the cells may be preserved for much longer periods by some of the methods described below. (See Examples)

Accordingly, another embodiment provides a kit, comprising:
a blood anti-coagulant;
a plurality of hypotonic solutions;
at least one fluorescent dye; and
a resealing solution having an osmolality of at least 1000 mOsm/kg.

In one embodiment, the kit provides a plurality of hypotonic solutions to successively diluting a blood sample and achieve a final osmolality ranging from 80-90 mOsm/kg, e.g., ranging from 85-87 mOsm/kg. In one embodiment, the plurality of solutions comprise at least three or at least four hypotonic solutions, each having a different osmolality. In one embodiment, the plurality of solutions can have the same or different osmolalities, so long as the maximum osmolality any of the solutions is 300 mOsm/kg and the minimum osmolality is 50 mOsm/kg.

In any kit embodiments disclosed herein, the kit further comprises an isotonic saline washing solution comprising glucose or trehalose, e.g., a 5 mM glucose solution or at least a 50 mM trehalose solution (e.g., a 50 mM trehalose solution).

Another embodiment provides a method, comprising:
(a) combining erythrocytes with a blood anti-coagulant to form a solution having an osmolality of at least 300 mOsm/kg;
(b) successively diluting the solution in (a) with at least two (e.g., Example 2) or at least three hypotonic solutions to the reduce the osmolality to less than 100 mOsm/kg to cause the erythrocyte pores to open;
(c) combining the diluted solution in (b) with at least one fluorescent dye; and
(d) combining the dye-containing solution in (c) with a resealing solution having an osmolality of at least 1000 mOsm/kg to increase the osmolality, thereby causing the erythrocyte pores to close and entrap the at least one fluorescent dye within the erythrocytes.

In one embodiment, the kits or methods disclosed herein include an isotonic resealing solution having an osmolality of at least 2000 mOsm/kg.

In one embodiment, after performing any method disclosed herein, after step (d), the method further comprises:
(e) washing the erythrocytes in an isotonic saline washing solution containing glucose or trehalose to remove extracellular dye.

In one embodiment, the washing is performed with a saline solution containing 50 mM trehalose.

Another embodiment provides a kit, comprising:
a blood anti-coagulant;
water as the sole hypotonic solution;
at least one fluorescent dye; and
a resealing solution having an osmolality of at least 1000 mOsm/kg.

Virtually all past and current methods for preparation of erythrocyte ghost cells or substance-loaded erythrocyte ghost cells (S-IEs) are based on suspending erythrocytes in an hypotonic solutions (e.g., solutions having an osmolality less than that of plasma, which is about 300 mOsm/kg). This causes fluid movement into the cells, until intra-cellular osmolality drops to equilibrium with that of the solution in which they are suspended; thus, the cells swell. As they swell, pores from about 200-500 Å in diameter transiently open in their membranes, permitting transit of fluids and substances out of and into the cells. Generally, cells exposed to osmolality of about 80 mOsm or less swell to the extent that complete lysis takes place, thereby destroying the cells' membranes. For example, erythrocytes placed in distilled $H_2O$ quickly swell until they rupture. However, cells exposed to osmolality greater than about 80 mOsm/kg shrink to their normal dimensions once the osmolality of the solution in which they are suspended is elevated to about 300 mOsm/kg, causing the pores in the membranes to close and entrapping whatever fluid and substances were inside them.

The majority of methods for production of erythrocyte ghost cells or S-IEs employ dialysis to gradually lower osmolality of the solution in which the cells are suspended; alternatively, cells can be transferred from one to another through a series of solutions of decreasing osmolality. But in both cases, always the aggregate cell volume is small, compared to that of the fluid in which they are suspended at any time. This approach, illustrated in Examples 3 and 4, is different from any other stated method to date for opening pores in the cells' membranes, depends essentially upon "surrounding" the cells with very small volumes of hypotonic solution, relative to the aggregate cell volume, as compared to the common practice of "suspending" them in large volumes; moreover, the solution that is added to the cell volume is distilled, de-ionized $H_2O$ (0 mOsm/kg), as compared to hypotonic solutions having osmolality greater than about 80 mOsm/kg.

This approach takes into account that after the steps of washing and centrifugation, the packed erythrocytes have about an 80% haematocrit, meaning the spaces between the cells are occupied by a fluid having an aggregate volume approximately equivalent to 20% of the packed cell volume. Technically, this method involves adding $H_2O$ to the cells, as opposed to adding the cells to $H_2O$. Addition of the distilled, de-ionized $H_2O$ can take place in a single step, or it can take place as staged addition in several steps, but in any event, the total amount added is calculated to be only large enough to swell the cells to the same extent as if they were suspended in a large volume of solution having an osmolality no less than about 100 mOsm/kg, e.g., no less than about 80 mOsm/kg. The yield of normal ghost cells produced by this approach is reduced, compared to approaches wherein the osmolality of the solution surrounding the erythrocytes is less suddenly changed, however, remnants of damaged cells are sequestered from the undamaged ones by centrifugation and discarded as part of the supernatant. A variation of this approach would be placing the packed cells inside a dialysis bag immersed in water and agitated. The net result is that the time and effort to produce erythrocyte ghost cells or S-IEs can be significantly reduced and simplified.

Accordingly, another embodiment provides a method, comprising:
(a) combining erythrocytes with a blood anti-coagulant to form a solution having an osmolality of at least 300 mOsm/kg;
(b) combining the solution in (a) with water to the reduce the osmolality to no less than about 100 mOsm/kg to cause the erythrocyte pores to open;
(c) combining the diluted solution in (b) with at least one fluorescent dye; and
(d) combining the dye-containing solution in (c) with a resealing solution having an osmolality of at least 1000 mOsm/kg to increase the osmolality, thereby causing the erythrocyte pores to close and entrap the at least one fluorescent dye within the erythrocytes.

In one embodiment, the kits or methods disclosed herein provide at least one fluorescent dye, such as indocyanine green (ICG) dye. In one embodiment, the dye concentration of a composition comprising the entrapped dye ranges from 0.25 to 1.5 mM. In another embodiment, the dye concentration ranges from 0.3 to 0.4 mM. In one embodiment, this concentration optimizes fluorescence intensity to facilitate visualization of the cells. In yet another embodiment, the dye concentration is greater than 0.4 mM. This concentration can facilitate absorption by the cells of infra-red wavelengths, thereby rendering the cells capable of lysing upon heating.

In one embodiment, the source of erythrocytes is O-type blood. In another embodiment, the erythrocyte source blood of A-type or B-type. In the latter embodiment, the method can further comprise adding α- and β-glucosidase to split off the erythrocyte surface A- and B-agglutinogens, respectively.

In one embodiment, the composition comprising the dye entrapped in the erythrocytes further comprises at least one biocompatible excipient. In one embodiment, the at least one excipient is polysucrose. In one embodiment, the at least one excipient concentration ranges from 0.5% to 5%.

2. Pre-Prepared Small Volumes of S-IEs for Universal Injection:

One embodiment provides a method for producing S-IEs for end-users who want access to S-IEs without having to acquire blood from their subjects. This method can be performed on a large scale and can supply multiple end-users.

In situations where application of the above basic methodology may be inconvenient due to constraints of facilities location or time, it is possible to instead make use of S-IEs obtained from a source other than the subject. Using the basic methodology, aliquots from large volumes of erythrocytes from human O-negative blood type donors pre-loaded with various substances or mixtures of substances, can be slowly frozen and maintained at cryogenic temperatures until needed for universal injection. Such an approach can be used to create substance-loaded cells that can be universally injected into human subjects, while obviating the necessity to first obtain the subject's own blood and the time required for perpetration. This approach is particularly suited to preparations of cells loaded with substances likely to be used frequently in numerous subjects, such as for performance of standardised diagnostic or therapeutic procedures, where ad hoc use of substances is not contemplated.

Alternatively, the pool of subjects that forms the source of erythrocytes for bulk preparation of universally injectable substance-loaded erythrocytes can be expanded beyond those having only type O-negative by using α- and β-glucosidase to split off the cell surface A- and B-agglutinogens respectively, at the beginning of the cell-loading process. There appears to be nothing definitive in the literature to indicate the threshold level at which any cell membrane surface antigens not removed by washing or other treatment would induce an immunologic reaction. Since it is anticipated, especially with regard to diagnostic use, that the maximum volume of processed cells re-injected will be on the order of only 1 or 2 mL, there is minimal likelihood of inducing an immunologic reaction.

3. Preparation of Off-the-Shelf S-IEs for Universal Injection

Freeze-drying S-IEs prepared for universal injection into which the desired substances have been inserted at desired concentrations results in an off-the-shelf preparation that is easily stored at room temperature for prolonged periods (in excess of a year). Reconstitution requires only addition of sterile water, making such a product the most convenient form of injectable S-IEs. This would appear to be the most convenient method for rendering the substance-loaded cells stable and easily reconstituted. Accordingly, one embodiment provides a lyophilized or freeze-dried composition comprising at least one fluorescent dye entrapped within erythrocytes. In one embodiment, the composition further comprises at least one therapeutic agent and/or at least one saccharide entrapped within the erythrocytes. Exemplary saccharides include those selected from mannose, xylose, glucose, trehalose, sucrose and maltose. In an alternative embodiment to the saccharide, any substance that reduces formation of ice crystals can be entrapped within the erythrocytes, as disclosed herein.

Past attempts to develop a method for freeze-drying erythrocytes such that reconstitution of the cells results in erythrocytes with an intact cytoskeleton and with biologically active hemoglobin (i.e., completely biologically viable cells) have proven illusive; the fact that such a preparation is not readily available underscores this. Generally, when erythrocytes have been lyophilized by previous methods, for example in either an aqueous or phosphate-buffered saline (PBS) solution, the reconstituted cells are damaged to the extent that they are not capable of metabolizing (that is, the cell hemoglobin cannot carry oxygen), and/or the yield of intact, non-deformed cells is unacceptably low. A factor in causing the damage may arise in the freezing process, where ice crystals form internal and external to the cells, thereby disrupting cell structure. Attempts to obviate this problem seem mainly to have included procedures that utilize cooling rates that are faster than ice crystal formation (see for example, U.S. Pat. No. 5,656,498), or inclusion in the cell suspension fluid a monosaccharide which may or may not diffuse into the cells, the presence of which suppresses ice crystallization during cooling (see for example, U.S. Pat. No. 5,340,592). However, it appears that these approaches have failed to produce sufficiently high yields of functional cells upon reconstitution to be useful in the clinical arena.

With this embodiment, the period that the cells are suspended in hypotonic solution with open pores in their membranes presents an opportunity to efficiently introduce controlled, sufficiently high amounts of monosucrose into the erythrocyte cells and eventually encapsulate it when the cells close.

In the methods disclosed herein, the entrapped dye is frozen or freeze-dried. This can be accomplished by freezing or freeze-drying compositions comprising the entrapped dye is frozen or freeze-dried. Accordingly, disclosed herein are frozen or freeze dried (lyophilized) compositions comprising a freeze dried (lyophilized) composition comprising at least one fluorescent dye entrapped within erythrocytes.

In one embodiment, the erythrocytes in (d) further entraps a substance (e.g., while in a hypotonic state) that inhibits the destructive formation of ice crystals during cooling. In one embodiment, the substance is a saccharide, e.g., trehalose. Accordingly, in one embodiment, erythrocytes can further entrap trehalose or at least one therapeutically effective agent.

Figure 4A:
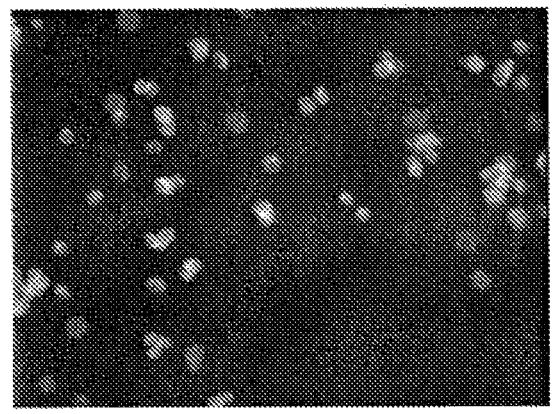
FIG. 4A is a near-infrared fluorescence micrograph at 40× magnification of ICG-loaded human erythrocytes.
Figure 4B:
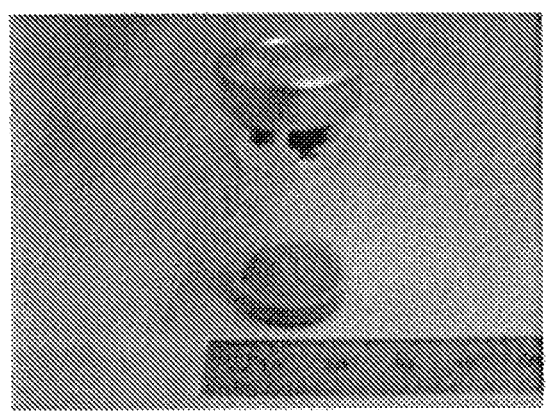
FIG. 4B is a photograph of a vial containing freeze-dried ICG-loaded human erythrocytes.
Figure 4C:
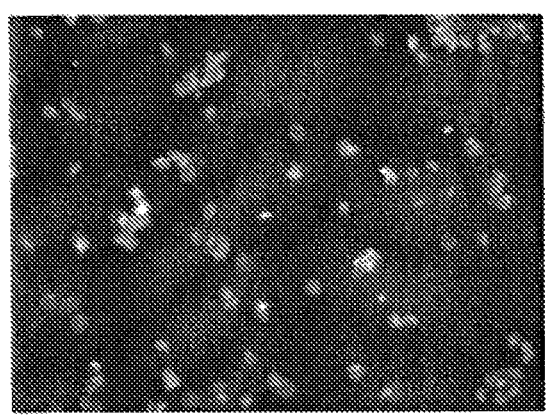
FIG. 4C is a near-infrared fluorescence micrograph at 40× magnification of freeze-dried ICG-loaded human erythrocytes reconstituted by addition of 1 mL of $H_2O$.

One embodiment relates to the recognition that obviating the problems encountered by these various previous attempts lies in recognition of two advantages associated with the methods of use and production of substance-loaded erythrocytes with respect to use and production methods aimed at long-term storage of metabolically functional blood. The first is that production of metabolically normal O2-carrying cells upon reconstitution is not important for the diagnostic and treatment applications of S-IEs; in fact, replacement of a portion of the cells' hemoglobin content is part of the loading process. Secondly, the methods of S-IE production all involve opening of pores in the cells' membranes to allow equilibrium between the cells' internal contents and the solution in which the cells are suspended. This latter situation readily facilitates controlled introduction of an adequate amount of substances that prevent crystal formation, as disclosed herein, e.g., saccharide (preferably, trehalose) to prevent ice crystal formation during the freeze-drying process; this is accomplished by substituting the 50 mM trehalose for the 5 mM glucose in the washing buffer solution composition described in the Example 1 Ad-hoc Preparation of ICG dye-loaded Human Erythrocytes for Autologous Re-injection. Once this is done, the finished substance-loaded cells are diluted in to a 50% "haematocrit" in the same trehalose washing buffer, polysaccharide (5%) is added as an excipient to reduce cell clumping upon reconstitution, when 1 mL of distilled, deionized water is added to the freeze-dried pellet in the stoppered vial. As demonstrated in FIG. 4, the reconstituted ICG-loaded human erythrocytes are equivalent in fluorescence intensity to that they possesses prior to freeze-drying.

Figure 12:
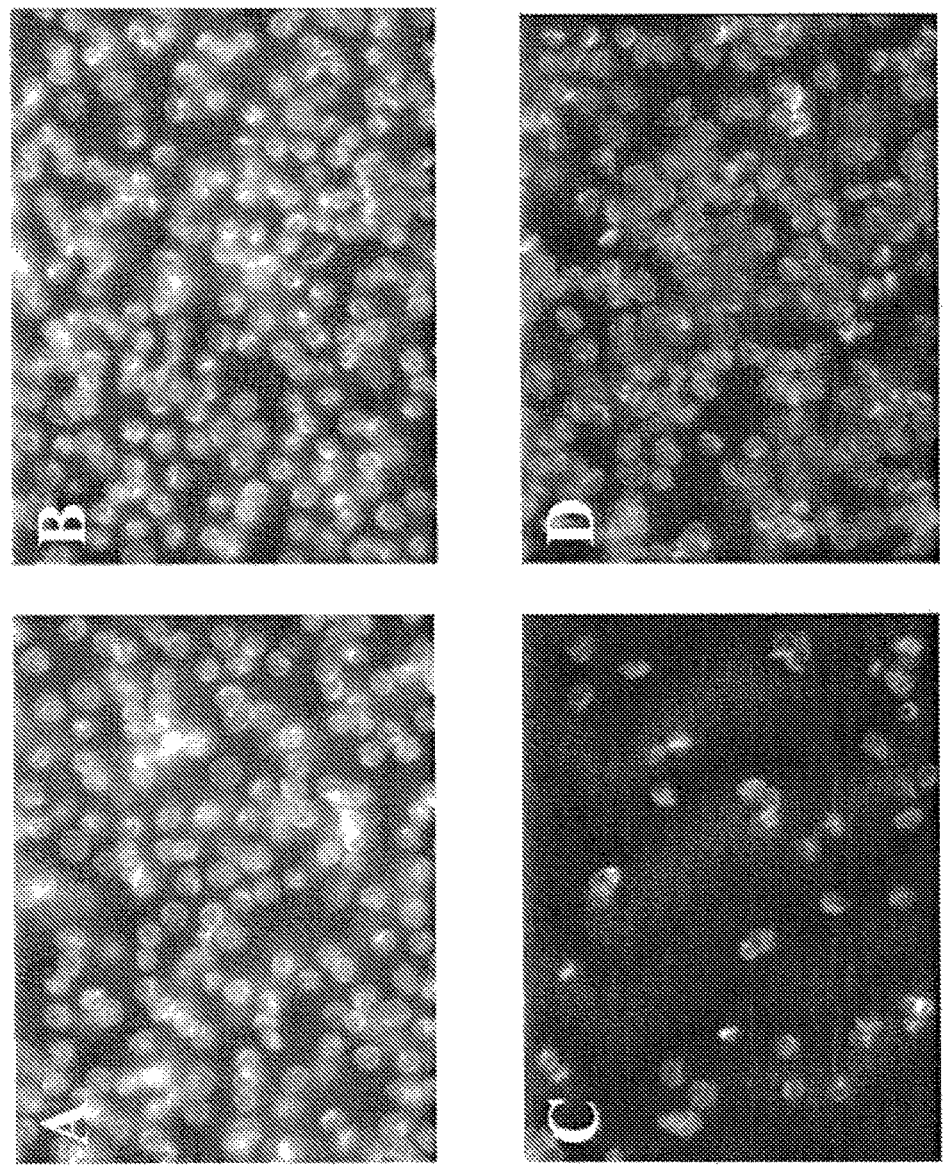
FIG. 12A is a fluorescence micrograph of ICG-loaded human erythrocyte ghost cells prior to freeze-drying.
FIG. 12B is a fluorescence micrograph of freeze-dried ICG-loaded human erythrocyte ghost cells following reconstitution by addition of sterile $H_2O$.
FIG. 12C is a fluorescence micrograph of freeze-dried ICG-loaded human erythrocyte ghost cells baked 24 hrs. at 80° C. following reconstitution by addition of sterile $H_2O$.
FIG. 12D is a fluorescence micrograph of freeze-dried ICG-loaded human erythrocyte ghost cells irradiated with 30 k gray following reconstitution by addition of sterile $H_2O$

In the freeze-dried state, substance-loaded erythrocyte ghost cells appear to be relatively unaffected by exposure to high levels of heat or ionizing irradiation, ultra violet radiation as evidenced by their normal appearance upon reconstitution following such exposures (see FIG. 12A-C), which is beneficial as exposure to one or more of these conditions could have sterilized the freeze-dried cells and/or de-activated any viruses that might be present.

Diagnostic Application of Fluorescent Dye-Loaded Erythrocytes

Medical angiographic imaging typically involves administration of a detectable substance to a subject, as described, e.g., in U.S. Pat. Nos. 6,915,154 and 6,351,663, the disclosures of which are incorporated herein by reference. In some instances the detectable substance may also be a therapeutic agent, as described in, e.g., U.S. Patent Publication No. 2004/0206364, the disclosure of which is incorporated herein by reference.

Aside from their role in supplying the metabolic requirements of the tissues they serve, among the naturally occurring particles in blood, as well as the artificial ones that have been introduced into blood circulation for various purposes, erythrocytes are well suited for use as substance carriers. They are the largest naturally occurring blood-borne particles, and from a hemodynamic point of view, they are essentially as passive as serum, adding only resistance to blood flow because of their size and mass. (By comparison, leukocytes and thrombocytes are biologically active, so their movements in flowing blood are influenced by other than serum fluid dynamics. For example, leukocytes, which are part of the immune system, exhibit a drag-and-roll behavior as they pass the endothelial surface of vessel walls.) Moreover, despite their large volumes, S-IEs retain the capability of the original erythrocytes to deform, allowing them to pass through small diameter capillaries; this feature overcomes the size limitation inherent in use of artificial carriers (such as liposomes) whose geometry always is rigid. These attributes of erythrocytes make them ideal for transporting the fluorescent dyes used in angiography. Unlike conventional angiograms showing dye-stained plasma movement, which often show a poorly defined wave front that transits only once, angiograms showing individual fluorescent erythrocytes can provide continuous information about blood flow speed and direction in a multitude of vessels simultaneously. There are several aspects of creating and using dye-loaded erythrocytes (e.g., ICG-loaded erythrocytes) for angiography:

1. Dye-loaded erythrocytes, rather than dye-stained ones, are desirable because dye binding to the outer erythrocyte membrane appears to be weak (i.e., not covalent binding). Energy imparted to those cells "stained" with dye as a result of turbulent blood flow, for example, is sufficient to break those weak bonds. Then dye molecules become available to bond with other nearby proteins, quickly resulting in plasma and blood vessel wall staining that diminishes contrast between the erythrocytes and their background, while at the same time diminishing the brightness of the erythrocytes themselves. Moreover, it is not possible to bind enough dye to the cell membranes to achieve the peak fluorescence intensity needed for adequate visualization of individual cells (see FIGS. 1A and 1B). On the other hand, the dye-loading process permits control of the amount of dye inserted into erythrocytes, such that the dye concentration inside the cells is very near—but does not exceed—the concentration at which fluorescence quenching occurs (cf. 1A and 1B to 1D). In the case of ICG, this is achieved by addition of 1 µmol of ICG dye to each milliliter of the dialysed erythrocyte solution at that point in the substance-loading procedure when the volumes of the cells have increased to the extent that pores in the cells' membranes have opened (see FIG. 2). With the pores open, transmembrane exchange of large molecules occurs; haemoglobin inside the cells moves to the outside until a dynamic equilibrium between inward and outward haemoglobin movement is reached. ICG dye added to the solution in which the cells are suspended binds with hemoglobin molecules, and in time, those molecules move into the cells and reach concentration equilibrium with those outside the cells. When the pores in the cells are closed and dye/haemoglobin molecules outside the cells are washed away, the remaining dye-loaded cells fluoresce optimally when stimulated by appropriate excitation light energy.

2. Once filled with dye-stained plasma, as in conventional fluorescent dye angiography, blood vessels exhibit only steady-state fluorescence, inhibiting visualization of any blood-borne particles, even if the particles themselves were fluorescent. However, it is possible to visualize individual erythrocytes in capillaries if they, rather than the plasma, are emitting fluorescence and if separation between adjacent erythrocytes exceeds the diffraction limited resolution of the optics of the eye (about 7 µm for the perifoveal capillaries and 11 µm for the choriocapillaris (see Flower R W. Optimizing treatment of choroidal neovascularization feeder vessels associated with age-related macular degeneration. Am J. Ophthalmol. 2002; 134:228-239.[8]). These conditions were met by entrapping ICG dye in erythrocytes, as described above, and re-injecting a small bolus of them. During transit to the ocular vasculatures, they are diluted in circulating blood to the extent that individual ICG-loaded cells were separated by more than 11 µm, making visualization of them possible. It has been discovered that using erythrocytes loaded so as to produce optimal fluorescence produces the strongest fluorescence signal for any given level of excitation light irradiance. For reasons of safety, it is desirable to remain as far below the maximum permissible exposure (MPE) for a given tissue as possible.

3. Visualization of circulating dye-loaded erythrocytes requires use of a device that irradiates the tissue field-of-view of interest with light energy at an appropriate wavelength (optimally, 805 nm for ICG). This can be efficiently done when that energy is applied as high-frequency trains of high-peak-power, short duration pulses of light, each of which illuminate the entire field-of-view of interest. This configuration results in a high image signal-to-noise ratio by requiring the lowest signal amplification, thereby minimizing introduction of electronic noise associated with amplification. Additionally, acquiring images during very short time periods in synchrony with short duration pulses of illumination acts essentially to freeze motion within each image, thereby obviating blurring associated with movement of erythrocytes within the field of view (FOV).

Accordingly, another embodiment provides method for controlled release of a therapeutic agent, comprising:
(a) administering to a patient, a composition comprising erythrocytes having entrapped therein both the therapeutic agent and a fluorescent dye;
(b) applying radiation to a field of view of a vasculature of interest at a selected wavelength and power to cause the erythrocytes to fluoresce;
(c) applying an increased power level of the same fluorescence-stimulating radiation to a target vasculature area within the field of view, such that the increased power heats the erythrocytes due to absorption by the entrapped dye, causing them to lyse and release the entrapped therapeutic agent.

In one embodiment, a portion of the erythrocytes contain ICG at a concentration that maximizes fluorescence efficiency, and the remainder contains both the therapeutic agent and ICG at a dye concentration that enhances light absorption, rather than fluorescence.

In the composition of (a), at least a portion (if not substantially all) of the erythrocytes each have both the therapeutic agent and fluorescent dye entrapped therein.

The efficacy of using dye-loaded erythrocytes has been successfully demonstrated in both rabbit and non-human primate eyes[9]. (see Flower R, Peiretti E, Magnani M, Rossi L, Serafini S, Gryczynski Z, Gryczynski I., Observation of erythrocyte dynamics in the retinal capillaries and choriocapillaris using ICG-loaded erythrocyte ghost cells. Invest. Ophthalmol. Vis. Sci. 2008; 49: 5510-5516, the disclosure of which is incorporated herein by reference). Moreover, the results reported validated the prediction by Bek that all the clinical findings concerning edema in diabetic maculopathy can be explained as a result of disturbances in retinal vasomotion[10]. Results have also been obtained from the first human subjects in a preliminary clinical study to demonstrate feasibility of autologous re-injection of ICG-loaded erythrocytes for angiography (see FIG. 5). The human study protocol required injecting very small volumes of ICG-loaded cells in the first subjects and gradually increasing the volume in subsequent ones, until reaching a level equivalent to that used in the monkeys. Consequently, there are significant differences between the appearance of the published monkey angiograms, where the methodology had been optimized, and these from these first human subjects. The main reason is that the fraction of circulating fluorescent erythrocytes in these first human subjects was about 4-times less than in the monkeys.

Figure 5A:
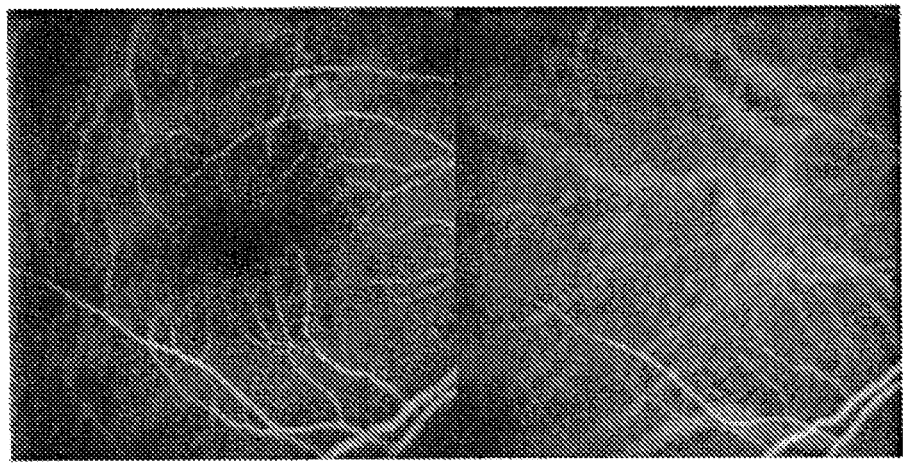
FIG. 5A is a sodium fluorescein angiogram image (left) and a conventional ICG angiogram image (right) for orientation of a patient's normal right eye.
Figure 5B:
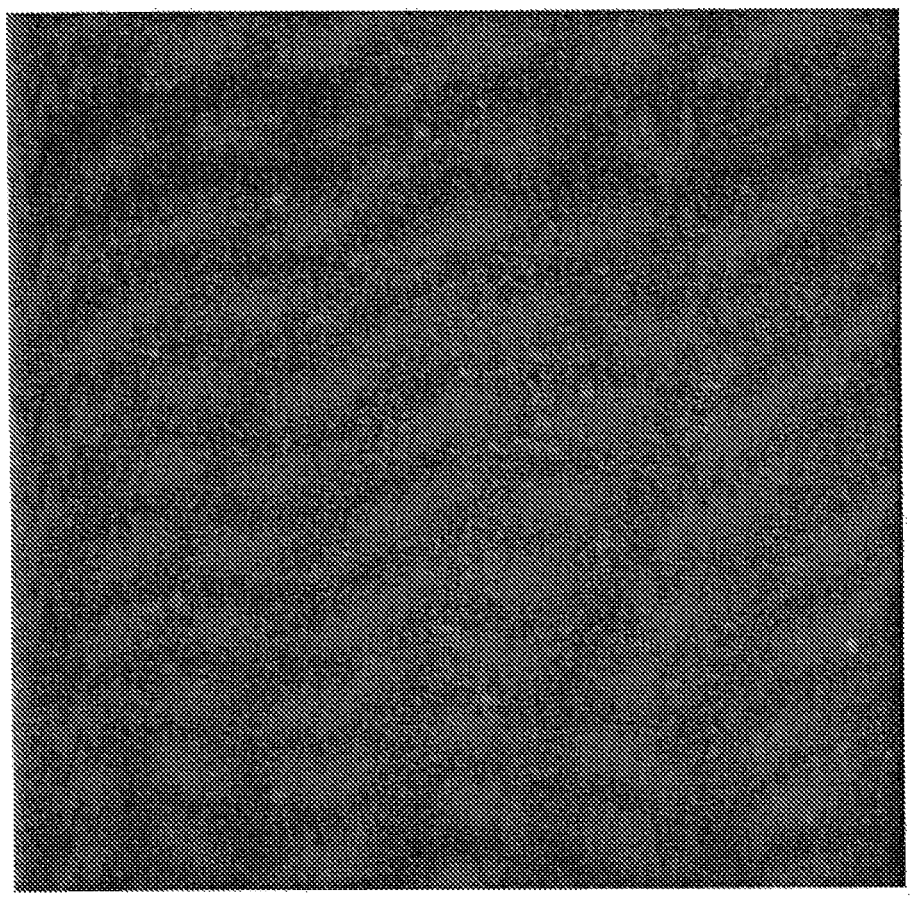
FIG. 5B is an angiogram image of ICG-loaded erythrocytes of the patient's normal right eye; individual erythrocytes appear as white dots.
Figure 5C:
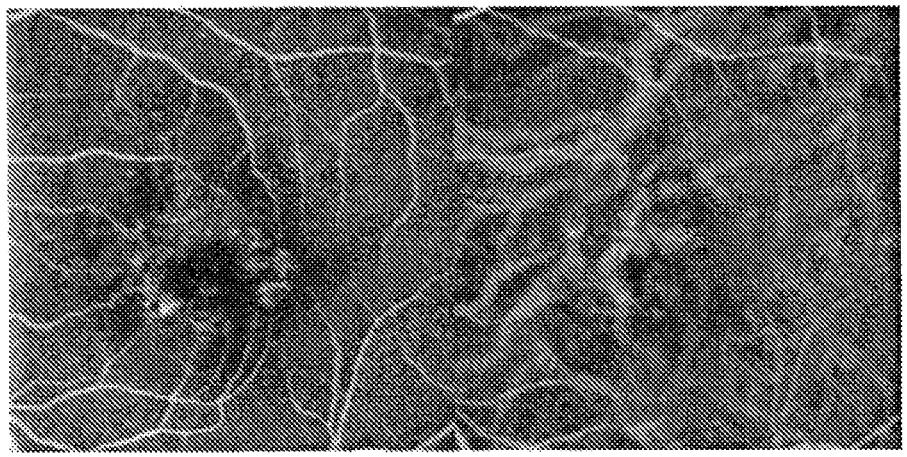
FIG. 5C is a sodium fluorescein angiogram image (left) and a conventional ICG angiogram image (right) for orientation of the patient's diseased left eye.
Figure 5D:
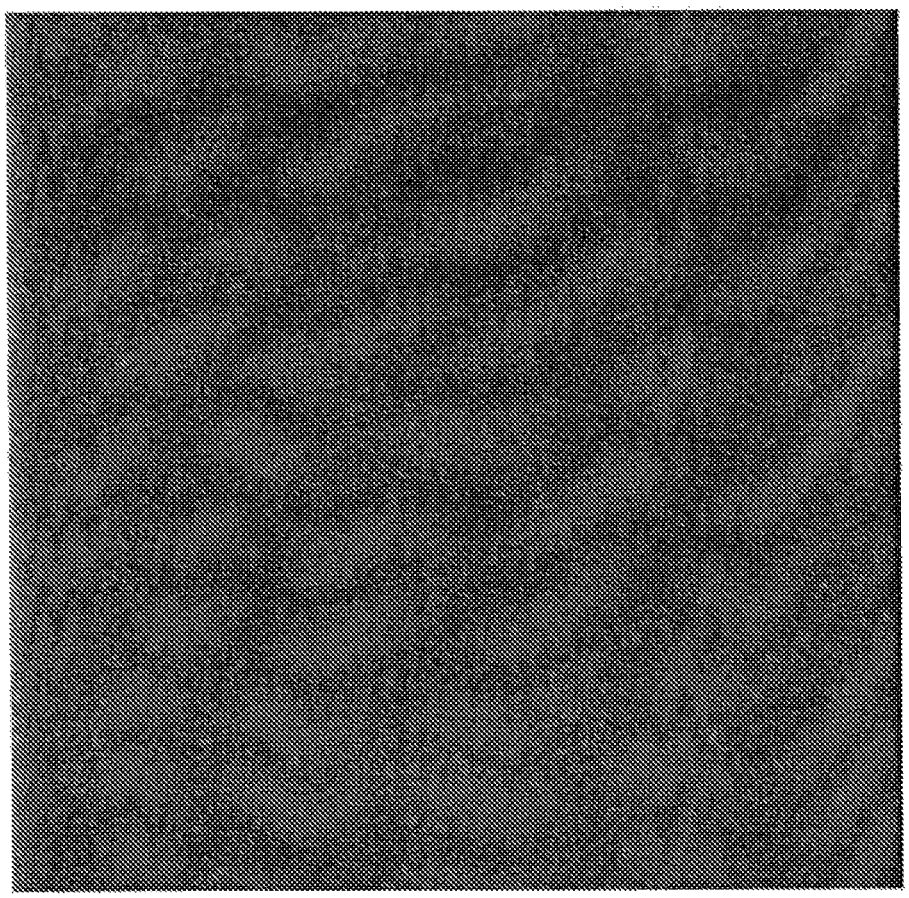
FIG. 5D is an angiogram of ICG-loaded erythrocytes of the patient's diseased left eye; individual erythrocytes appear as white dots.

Nevertheless, these first human angiograms support some of the findings in the more extensive monkey studies. FIGS. 5A and 5B are from the normal right-eye of an age-related macular edema subject; FIG. 5B shows a single ICG-loaded erythrocyte angiogram image of the 10°-area field of view. The distribution of stalled erythrocytes is relatively even, consistent with what was reported for the normal monkey eye[9]. In the diseased left eye (FIGS. 5C and 5D), the image from the angiogram is centered over the choroidal neovascular lesion (CNV). The distribution of stalled erythrocytes surrounding the CNV is similar to that of the normal fellow eye, but in the CNV no erythrocytes are apparent. When watching the actual angiogram movie, however, a few erythrocytes eventually do pass through the CNV area; but they do so at about half the speed as those erythrocytes which are not stalled in the area surrounding the CNV or those in the normal eye. (This may be the result of both plasma skimming and of higher CNV resistance to blood flow.) Minimally, the first human angiograms demonstrate that ICG-loaded erythrocytes can be acquired and that apparently the presence of vasomotion—or lack of it—can be determined thereby. Based on Bek's work[10], visualization of erythrocytes can be used as a predictor for retinal edema onset and for monitoring early efficacy of treatment. Also, clearly ability to track individual erythrocytes makes possible routine quantifiable assessment of blood flow in any vessel.

Exogenous Substances for S-IE Fluorescence Enhancement

In one embodiment, the methods disclosed herein further comprise the step of adding metallic colloids prior to step (d). In one embodiment, the metallic colloids are silver.

Metallic silver colloids in close proximity to weakly fluorescing dyes can markedly increase fluorescence yields. It has been shown that if ICG molecules are brought into close proximity by first binding silver colloids to amino groups that have been plated on a glass surface and then binding ICG/albumin conjugates to the same surfaces, fluorescence yields from the ICG increased more than 30-fold[11]. Subsequently, experiments were carried to determine if the same enhancement effect would occur in vivo in ICG angiograms made in rabbit eyes.

Figure 6A:
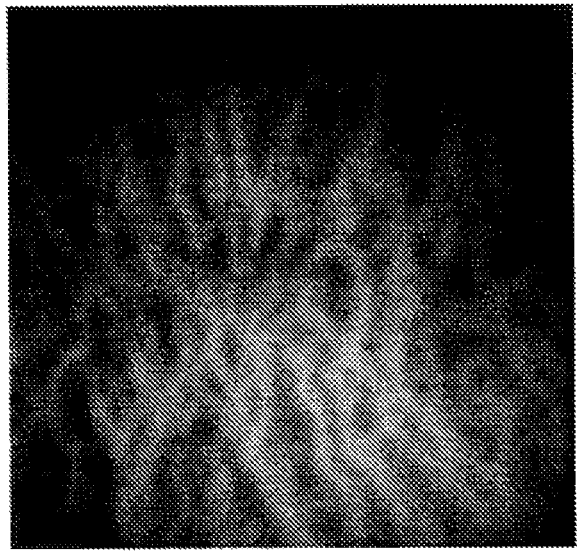
FIGS. 6A and 6B are angiogram images from the same rabbit eye comparing ICG fluorescence in the choroidal vasculature following conventional intravenous injection of a bolus of aqueous ICG dye (6A) and following injection of an identical bolus containing silver colloid (6B)
Figure 6B:
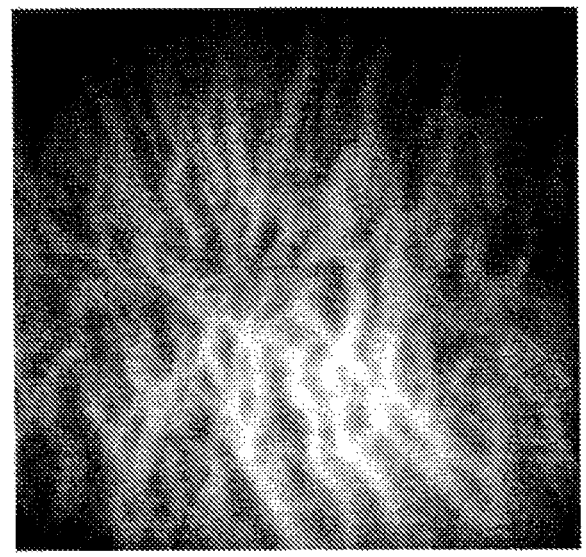

Samples of ICG dye alone and of dye/Ag-colloid suspension, containing identical concentrations of dye (0.250 mg/mL) were injected into rabbit ear veins, and ICG fluorescence angiograms recorded. The fundus of the eye was uniformly illuminated by pulsed laser diode light at 805 nm wavelength, and as the dye transited through the ocular vasculatures, the 835 nm wavelength fluorescence light emitted by the dye was digitally recorded. Comparison of dye only and dye/colloid-suspension angiograms from the same eyes were made, using images from the same phase of vascular dye filling in each case. As indicated by the example angiogram images in FIG. 6, the fluorescence intensity of the dye/suspension ranged from only two to three times greater than that from dye alone.

Figure 7:
FIG. 7 is an infrared fluorescence image comparing the fluorescence enhancement effect of silver colloid in 0.05 mg/mL ICG solutions; samples in the left-hand side contain no colloid, while those in the right-hand side contain colloid; samples at the top are in 1-cm thick tubes, while those at the bottom are 100 microns thick.
Figure 8:
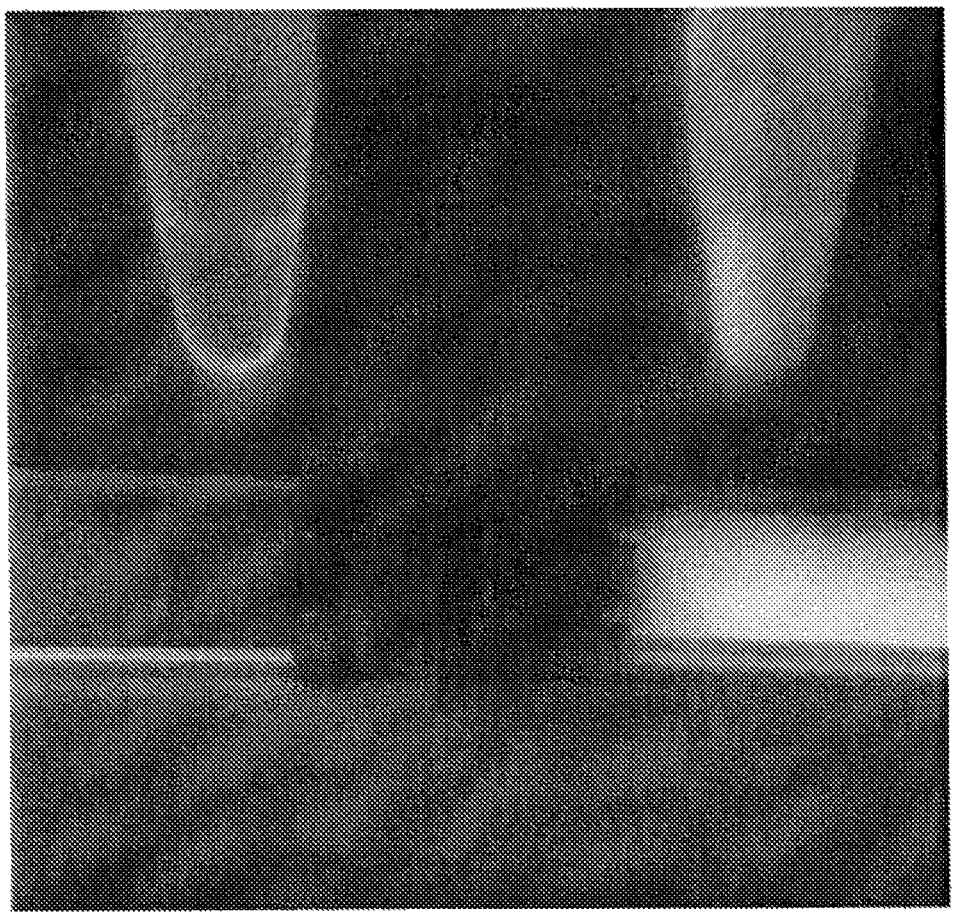
FIG. 8 is an infrared fluorescence image of the samples of FIG. 7 showing reflection of the 805-nm wavelength light used to stimulate fluorescence; no barrier filter was placed in front of the CCD camera in this case.

The disparity between fluorescence enhancement reported in the experiments made using glass surfaces on which the dye/colloid conjugates were bound with amino groups (30-fold) and those observed in the in vivo angiograms (2- to 3-fold) apparently was due to the fact that the colloid fluorescence-enhancement effect is manifest in very thin layers of the dye/suspension and suppressed in thick ones. This is demonstrated by comparing fluorescence from thick (1 cm) and thin (100 μm) layers of both samples, as shown in FIG. 7. In this figure, the thick samples are at the top, and the thin ones at the bottom; 0.250 mg/mL ICG in HAS is on the left, and 0.250 mg/mL ICG in HAS with 4.684 mg/mL Ag colloid on the right. The array of samples was uniformly illuminated with 805-nm wavelength light, and the ICG fluorescence image was captured. In the case of the thick samples, the ICG-only on the left is significantly brighter, while in the case of the thin samples, the dye/colloid suspension is significantly brighter. In part, the explanation for these relationships is that colloids in suspension scatter light, as shown in FIG. 8, wherein the same array of samples in FIG. 7 is uniformly illuminated with 810 nm wavelength light and an image made from the reflected light. Note that both the thick and thin dye/colloid samples reflected—rather than absorbed or transmitted—the incident light; that is, the observed light interactions with the dye/suspensions arise as a surface phenomenon. Consequently, more dye molecules in the ICG-only thick sample interacted with light than did those in the dye/suspension thick sample. In the case of the two thin samples, however, the fluorescence enhancement in the dye/suspension sample resulted in brighter fluorescence from the ICG dye molecules present than from the same density of molecules in the dye-only sample. This was because more of the incident light was transmitted by the dye-only sample than by the dye/colloid-suspension one.

Based on the above observations, achieving significant ICG fluorescence enhancement in angiography through association of the dye with metallic colloids requires not only that the dye molecules be held in close association with the colloids, but that the dye/colloid conjugation be contained in thin layers. These conditions can be met by containing the dye/colloid conjugates within S-IEs, wherein the small amount of hemoglobin remaining in the cells is sufficient to act as the ICG protein-binding site. Thus, significant and useful enhancement of the dye fluorescence from ICG-loaded S-IEs can be achieved by encapsulation of silver metallic colloid during the S-IE loading process.

Therapeutic Application of Substance-Loaded S-IEs

In one embodiment, the erythrocytes entrap at least one therapeutically effective agent. Since S-IEs essentially are closed-volume circulating containers in which the concentration of inserted molecules can be precisely controlled, S-IEs can be used to transport their contents, sequestered from the blood, to a given vascular location, where their presence can be detected and their contents released. Such a scenario assumes that the vascular location is visually accessible, that the S-IEs contain a detectable marker (such as a fluorescent dye) in addition to the transported substance, and that a means to release the S-IEs' contents exists.

Controlled substance release in targeted vascular areas by this method makes possible use of substances that would be prohibited if delivery were by conventional means. This is because when encapsulated in S-IEs and injected in a bolus of packed cells, the aggregate substance volume introduced is very small. So long as that aggregate volume is on the order of 1/100th of the threshold volume for producing a pharmacological effect (therapeutic or toxic), it generally is considered micro-dosing. (In Canada, Europe, and the U.S., now human experimental IND studies often can proceed on the basis of just small animal data. This puts such studies in a range more likely to be affordable by smaller companies.) Therefore, the spectrum of dyes that might be considered potentially usable is greatly expanded when administered as micro-doses.

S-IEs maintain the shape, behavior, and longevity of the erythrocytes from which they are derived, so they are able to deform in order to pass through small diameter capillaries, making them ideal vesicles for carrying and delivering substances intravascularly. Re-injected substance-loaded erythrocytes can circulate for up to about 120 days (the average lifetime of erythrocytes), during which time their contents will be released by one means or another. Because any population of S-IEs behaves the same as any population of normal erythrocytes with respect to eryptosis, unless externally triggered to do so, only a small fraction of injected cell contents will be released at any particular time, complete release being spread-out over approximately 120 days. And since only very small volumes of cells are injected, levels of molecules released into the body at any point in time—or even in the aggregate—should always be orders of magnitude below effect or toxic thresholds. Moreover, since the distribution of S-IEs eventually would be uniform throughout the total circulating blood volume, further diluting the concentration of gradually released substance to possibly undetectable (or at least, trace) levels.

During initial transit through the circulation, an injected packed S-IE bolus remains relatively intact. Within a few minutes following injection, the S-IEs become fairly distributed throughout the body, and unless somehow targeted in a specific area of the body, thereafter substance release is gradual over a 120-day period. In vasculatures that can be directly observed by optical means, release of the drug content of circulating S-IEs can be triggered by application of light energy, especially during initial and early transit. Such light energy could easily be focused to cover any desirable area, small enough to cover a single cell or large enough to cover the vasculature of an entire organ.

Direct visualization facilitates control over the amount of substance released, by taking into account that, for any given area of vasculature anywhere in the body, the density of circulating S-IEs will be greatest during initial transit and will rapidly diminish with passage of time until only a few cells will be present in each capillary of the visualized area. For example, if the light energy were applied to a certain vascular area during the initial passage of the injected cells, released substance concentration would be high; if applied a few minutes later, the concentration would be much less, but always in proportion to the ratio of S-IEs to normal circulating erythrocytes. Even though the aggregate volume of injected substance encapsulated in S-IEs may be at the micro-dose level, when released only within the blood volume of a small area of vasculature, substance concentration could be very high.

Accordingly, in combination with the methods disclosed herein wherein step (d) results in a first population of dye-entrapped erythrocytes, after step (d) the method further comprises:

(e) repeating steps (a) and (b) with a second sample of erythrocytes;

(f) repeating step (c) with at least one fluorescent dye at a concentration higher than that of step (c);

(g) repeating step (d) with the product of (f) to form a second population of dye-entrapped erythrocytes; and (h) combining the first and second populations.

In one embodiment, the method further comprising adding at least one therapeutically effective agent at step (e) or (f), wherein the second population further comprises agent-entrapped erythrocytes. Numerous therapeutically effective agents can be envisioned for pre-loading. Exemplary drugs include ganciclovir (antiretroviral), triamcinolone acetonide (steroid); fluocinolone and dexamethasone (ocular-specific steroids); pegaptanib sodium and rhuFab V2 (Anti-VEGF, anti-angiogenic); verteporfin (benzoporphyrin derivative) (Photodynamic:therapy); and carboplatin and topotecan (chemotherapeutic).

In one embodiment, the at least one dye in the first population has a concentration ranging from 0.3 to 0.4 mM, and the at least one dye in the second population has a concentration greater than 0.4 mM, wherein upon illumination with 805 nm laser energy, the erythrocytes of the first population will fluoresce, and wherein increasing the laser energy heats the erythrocytes of the second population due to their enhanced absorption, causing them to lyse and release the entrapped therapeutic agent.

Figure 13:
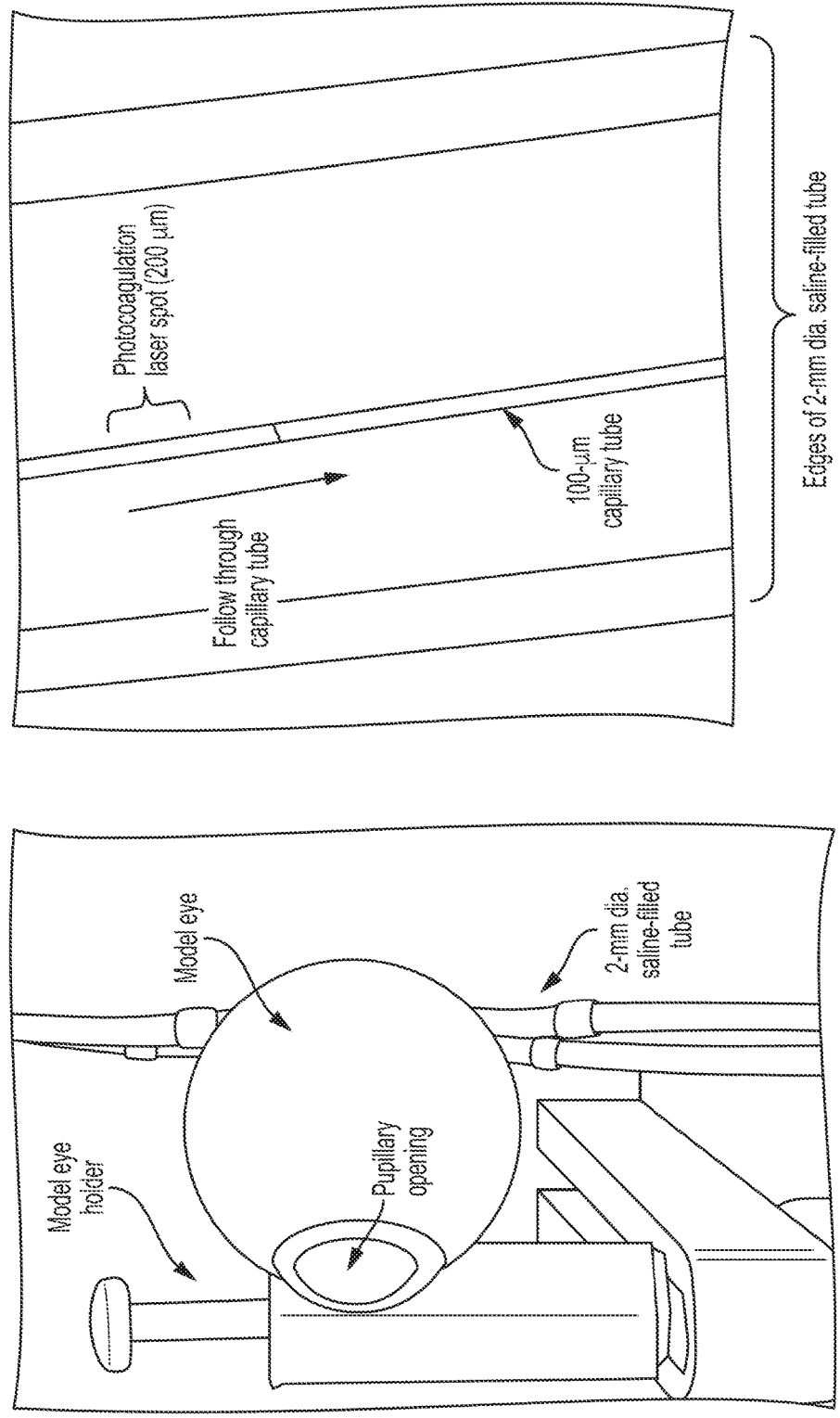
FIG. 13 shows the model eye system used to demonstrate release of ICG dye from ICG-loaded S-IEs induced by absorption of 805-nm wavelength laser energy when applied as a 200-μm dia. spot to a segment of a 100-μm dia. capillary tube with a mixture of high- and low-ICG-concentration loaded S-IEs flowing through it.
Figure 14:
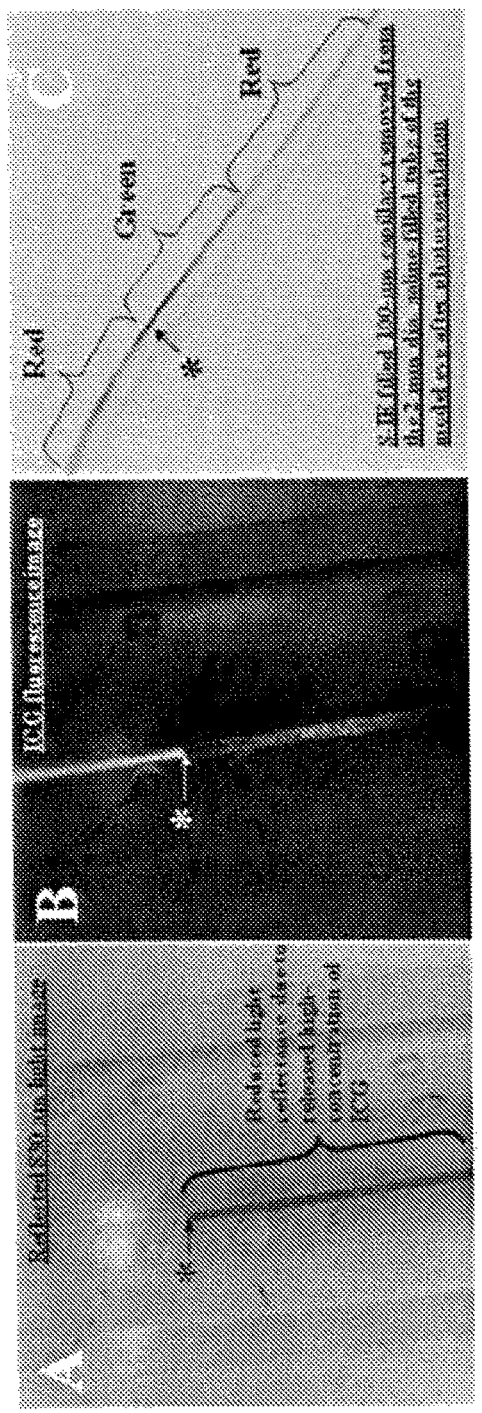
FIGS. 14A-14C show the capillary tube from the model eye in FIG. 13 following 805-nm laser-induced lysis of the ICG-loaded S-IEs in a 200-micron diameter area (spot) in the tube. 14D is a high-magnification fluorescence image of a portion of the tube not exposed to the laser light spot, wherein the broken-arrow indicates one of the S-IEs with ICG concentration so high that fluorescence is quenched, and the solid-arrow indicates one containing a lower concentration that fluoresces brightly.
Figure 14:
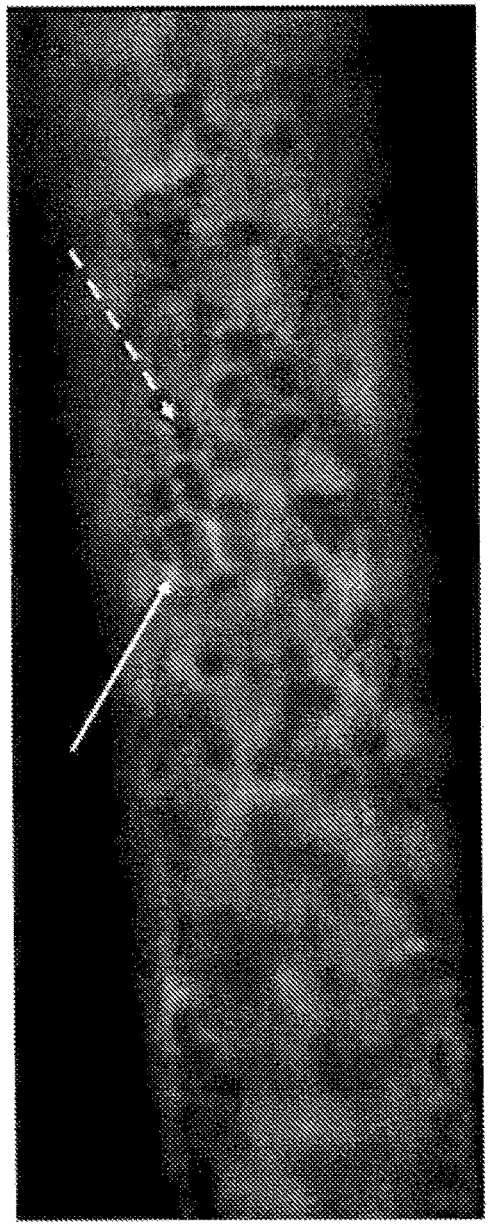

Proof-of-concept of this embodiment has been demonstrated in a model capillary system, as demonstrated in FIG. 13, wherein a spot of 805-nm wavelength laser energy impinged upon the mixture of high- and low-ICG concentration S-IEs in the capillary tube (see FIG. 14D), and the high-concentration-ICG-loaded cells absorbed the energy, heated-up, lysed, and released their contents. Immediately thereafter, when a reflected 830-nm light image of the capillary tube was acquired (FIG. 14A), the non-lysed dye-filled cells in clear saline (above "*") highly scattered the light, but the released dye in the saline (below "*") highly absorbed it, accounting for the dark portion of the capillary tube. The fluorescence image of the tube (FIG. 14B) shows fluorescence from the optimally fluorescing S-IEs containing lower ICG concentration (above "*"), but the released high concentration of dye in the saline directly below "*" only absorbs the near-IR light. Still further below, the concentration of released dye tapers off, and fluorescence of from non-lysed cells shows through. In addition to ICG dye, all the S-IEs contain hemoglobin, so in the clear saline (above "*" in FIG. 14C) they tend to scatter light and appear red in a color image of the capillary tube made after it was removed from the model eye. However, (below "*"), ICG dye was freed from the lysed cells, and the green dye-stained saline masked the non-lysed S-IEs. FIG. 14D shows a non-photolysed portion of the 100-µm capillary tube, wherein the dashed-arrow indicates a cell containing a high concentration of ICG, and the solid-arrow indicates a cell containing a low concentration of ICG. The S-IEs used in this demonstration were prepared by the method of Example 3 below.

Figure 15:
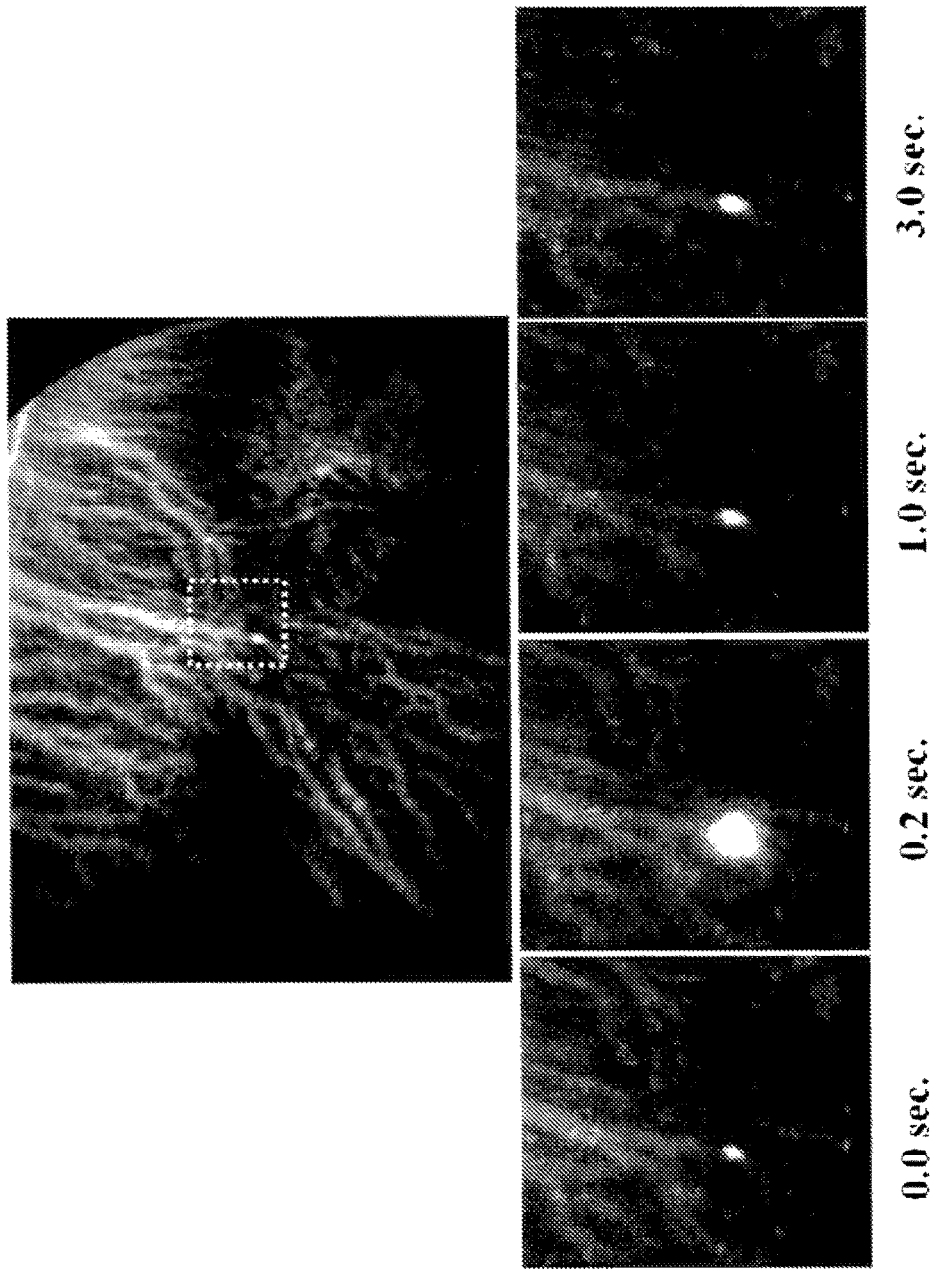
FIG. 15 shows 4 sequential frames from an angiogram made while exposing ICG-loaded S-IEs to focal laser energy during passage of an injected bolus of cells.

Proof-of-concept also was demonstrated in the vasculature of the rabbit eye, as demonstrated in FIG. 15, wherein the S-IEs were prepared by the method of Example 2 below, and wherein the release of ICG dye from the erythrocyte ghost cells (S-IEs) in which it was encapsulated resulted from application of a spot of 805-nm wavelength laser light during transit of a small intravenously-injected bolus of the cells. (The large image is for orientation on the rabbit eye fundus; the dashed-line box indicates the area shown in the row of smaller images. The bright off-center spot is the location of the laser aiming beam.) The first frame shows cells flowing upward through a vein at time 0 seconds. 0.2 seconds later, the laser fired, producing the larger, brighter spot. Up to 1 second thereafter, the brightness in the vessel was noticeably diminished presumably due to the release of entrapped dye (cf. FIG. 14). By 3 seconds later, the brightness of the flowing cells had recovered. It should be noted that the S-IEs used were not optimally loaded with ICG for maximum energy absorption, nor did vessel occlusion occur; this was necessary to allow continued blood flow so that brightness recovery could be assessed.

Ability to release an encapsulated substance from S-IEs requires ability to detect or observe presence of the cells in the target area, so that release-stimulating light energy can be applied precisely at the time the desired concentration of cells is present. This is accomplished by including a fluorescent dye (such as ICG) in the cells, along with the therapeutic substance. A software algorithm applied to the video images of the vasculature of interest can be used to track in real time the number—and hence, density—of S-IEs present in the vascular area of interest, and when the desired level is reached, it can automatically trigger application of the release-stimulating light energy. Knowing the density of cells present prior to triggering release may be necessary to assure that not so many cells simultaneously rupture that significant reduction or occlusion of blood flow occurs.

Accordingly, one embodiment provides a software algorithm applied to the video images of a vascular area of interest that can track in real time the number—and hence, density—of S-IEs present in the vascular area of interest. In one embodiment, when a predetermined level of S-IEs density is reached, application of light energy capable of causing the substance-loaded erythrocytes to release their contents will be triggered.

In another embodiment, a software algorithm takes into account the respective volumes of two different substance-loaded erythrocyte populations injected as a mixed bolus, the total volume of circulating blood, and the time elapsed following injection, will, based on the detection of S-IEs of one type, calculate the density of the other type present.

In one embodiment, where the type of S-IE detected is loaded with ICG dye, and the second type of S-IE present is loaded with a therapeutic agent as well as the highest possible concentration of ICG, the latter substance being entrapped to facilitate absorption of infra-red wavelengths, thereby heating and lysing the cells.

The applied light can interact with the S-IEs in a number of ways to cause release of the cells' contents. For example, the light can be selectively absorbed by the cells, thereby raising their temperatures to the point they rupture, or it might react with a specific molecule associated with the cell membrane that will compromise the membrane's structural integrity, causing rupture. Selective absorption of light energy can be accomplished by applying a wavelength that is efficiently absorbed by some substance associated with the substance-loaded cells. For instance, assuming those cells also contain a fluorescent dye to facilitate visualizing them, then a higher power level of the same fluorescence-stimulating light can be applied to just the target vascular area rather than the entire field of view. Of course, if this approach is used, then, it becomes desirable to have as much of the dye as possible present in the S-IEs for efficient light absorption.

If, however, the dye in question undergoes fluorescence concentration quenching, then there is an optimum concentration of its molecules, in any given volume and for any given illumination level at which optimum fluorescence occurs. Above or below that optimum concentration, reduced fluorescence intensity occurs, and exceeding the maximum permissible exposure (MPE) cannot compensate for that. (For example, the specific methodology employed to insert ICG into S-IEs is such that only the optimum concentration of dye molecules is present in the loaded cells, about 0.03 mg/mL; above that level fluorescence quenching occurs.) Thus, the optimum inter-cellular dye concentration for stimulating cell fluorescence is not necessarily high enough to act as an absorber of laser energy for purposes of heating the cells to the level that they lyse and release their contents; optimum absorption calls for the highest possible dye concentration. The solution to this dilemma is to inject a mixture of two species of S-IEs: one containing just the fluorescent dye at the optimum concentration for maximum fluorescence, and the second one containing both the therapeutic substance and the dye at the maximum concentration possible. The mixture would have fewer of the former type cells than the latter, since the purpose of the first type is only to indicate presence of the loaded S-IEs and to facilitate determining their concentration within the vascular area of interest.

EXAMPLES

Example 1

Ad-Hoc Preparation of ICG Dye-Loaded Human S-IEs for Autologous Re-Injection

Figure 9:
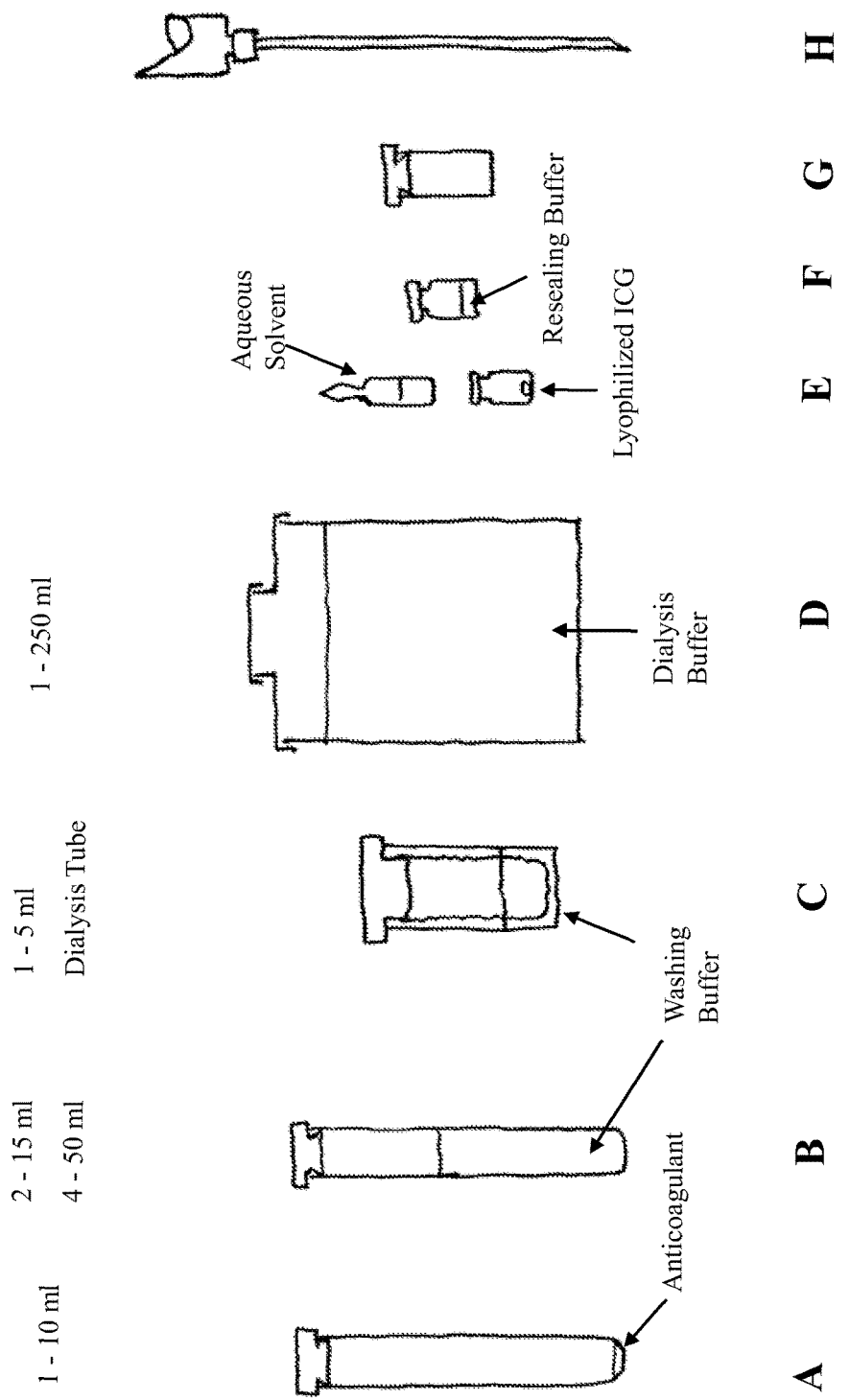
FIG. 9 is a schematic diagram of an embodiment of a kit containing sterile containers used in substance loading of erythrocytes (see Example 1)

ICG is encapsulated in human erythrocytes by a procedure of hypotonic dialysis, isotonic resealing and re-annealing. These steps are carried out using the various sterile containers (pre-loaded with appropriate fluids) included in a kit, as depicted in FIG. 9. Some of the containers are centrifuge tubes, and all containers and vials are disposable. FIG. 9 is a diagram of the sterile containers used in substance loading of erythrocytes. A: one 10-mL vacutainer containing an anticoagulant for acquisition of a blood sample. B: represents two 15-mL and two 50-mL centrifuge vacutainer tubes, each containing a pre-measured amount of isotonic saline washing buffer. C: a container having a rubber stopper top to which a length of dialysis tubing (sealed at its bottom) is affixed, such that an erythrocyte-containing solution can be introduced into the dialysis tube via an injection needle inserted through the rubber stopper. Outside the dialysis tube a small amount of washing solution keeps the dialysis tube membrane moist. D: a sealed container containing the volume of hypotonic dialysis buffer into which the dialysis tube containing the washed erythrocyte solution is lowered. In the center of this container's cover is a covered port into the rubber stopper of C fits. E: a rubber stoppered vial containing a pre-measured quantity of lyophilized ICG dye and a sealed vial containing a pre-measured volume of distilled, deionized $H_2O$ for reconstituting the dye. F: a rubber-stoppered vial containing a pre-measured amount of resealing solution. G: a rubber-stoppered vacutainer for storing the finished cells. H: one of a number of long (6") sterile needles for transferring cells from container to container.

Figure 10:
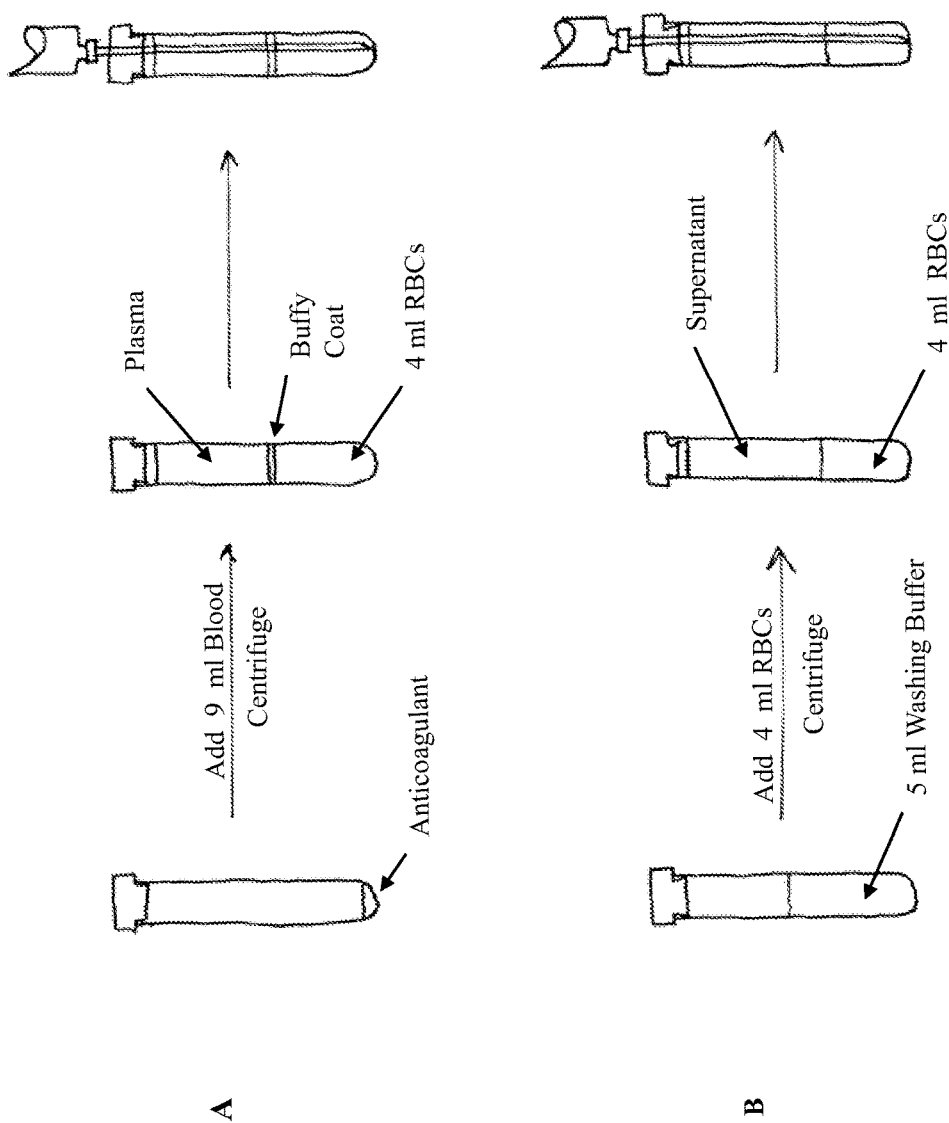
FIG. 10A is a schematic representation of the steps involved in removing a plasma- and leukocyte-free volume of erythrocytes from the bottom of the blood sample collection vacutainer after centrifugation, using a long needle.
FIG. 10B is a schematic representation of steps involved in removing a volume of erythrocytes from the bottom of the two 15-mL washing solution tubes after centrifugation, using a long needle.

Nine (9) mL of fresh blood, to which an anti-coagulant (acid-citrate-dextrose or ethylenediaminetetraacetic acid) is added, are obtained under sterile conditions and centrifuged at 2000 g for 5 min to obtain at least 4.0 mL of erythrocytes (see FIG. 10, A). Blood collection is done using a 10-mL vacutainer* pre-loaded with anti-coagulant. This same tube is then inserted into the centrifuge, and the blood is separated, with the erythrocytes at the bottom. Using a long needle connected to a syringe, the 4-mL erythrocyte sample is extracted from the bottom, so as to exclude any white cells in the overlying buffy coat and serum. (*Note: "vacutainer", as used throughout, refers to a variation of the sterilised rubber-stoppered evacuated test tube-like container commonly used for venipuncture. Each is constructed to withstand centrifugation, is sterilised, pre-filled with an appropriate fluid, and evacuated of air to form a vacuum.)

The erythrocytes are then washed twice in 10 mM HEPES (pH 7.4) containing 154 mM NaCl and 5 mM glucose (washing buffer) to remove leukocytes and platelets, centrifuging at 2000 g for 5 minutes each time. This is done by injecting the erythrocytes in the syringe, from the above step, into the first of two 15-mL vacutainer pre-loaded with 10 mL of washing solution and centrifuged, again at 2000 g for 4 min. Once the erythrocytes are again concentrated in the tube bottom, they are removed using the long needle and syringe (see FIG. 10, B) and transferred to the second 15-mL vacutainer pre-loaded with washing solution, centrifugation is repeated and the concentrated erythrocytes again collected in a syringe.

Figure 11:
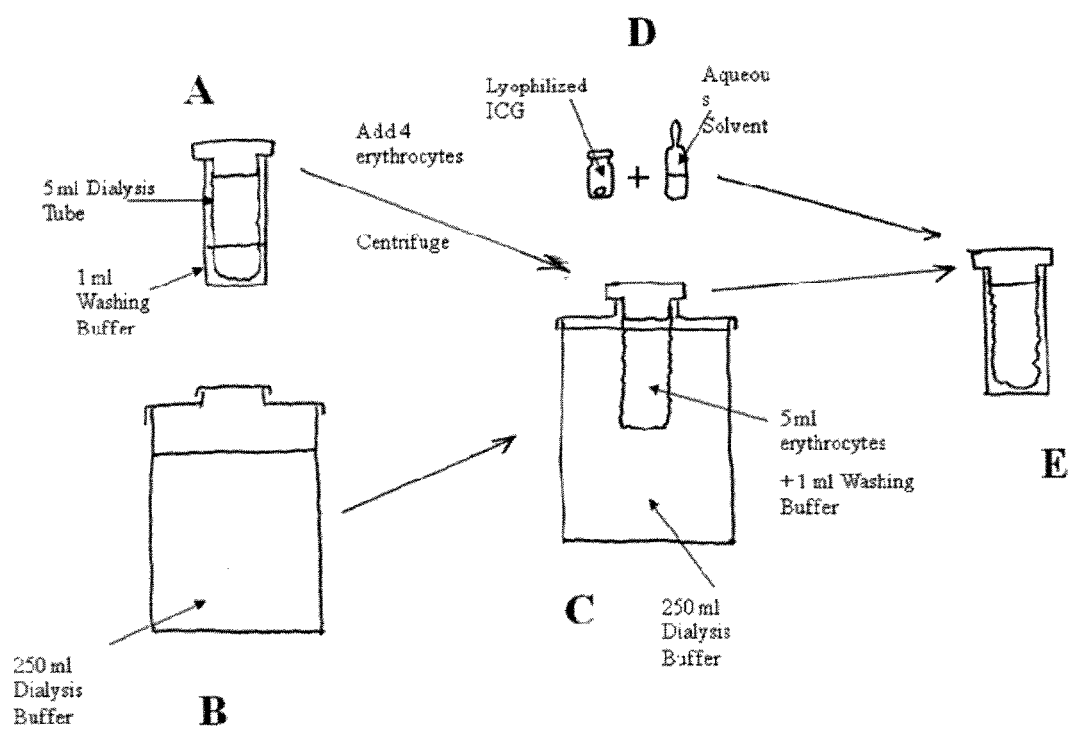
FIG. 11 is a schematic representation of the sequence ordered steps (A-E) detailing the use of those particular containers form the kit depicted in FIG. 9 to accomplish dialysis of the erythrocytes, including addition of ICG dye to the solution once dialysis is complete and pores in the cell membranes are open.

The erythrocytes then are suspended at 70% haematocrit (Ht) in the washing buffer solution inside a dialysis tube having a cut-off of 12-14 kD; this is done by injecting the syringe contents from the above step through the top and into the bottle containing the dialysis tube (see FIG. 11, A). The erythrocyte-containing dialysis tube is then removed from its bottle by lifting off the bottle top (to which the dialysis tube is attached) and transferring it to the large container (FIG. 11,B). The small lid of the large container is removed, and the dialysis bag is inserted through the opening and pressing it down to seal the container (see FIG. 11, C). Inside the large container, one volume of RBCs is dialysed for 90 min against 50 volumes of dialysis buffer (10 mM $NaH_2PO_4$, 10 mM $NaHCO_3$ and 20 mM glucose, pH 7.4) containing 3 mM reduced glutathione and 2 mM ATP. The osmolality of the buffer is about 60 mOsm, whereas that of the RBC solution reached about 87 mOsm at the end of the dialysis time. All these procedures are performed at 4° C.

The dialysis tube is then removed from the large container and returned to its original bottle, at which time 1 μmol of ICG dye is then added to each milliliter of the dialysed RBC solution (see FIG. 11,D), and the mixture is incubated for 30 min at 70° C. under gentle agitation. (The correct amount of lyophilised ICG is provided in a small vial to which a per-measured volume is added.)

The erythrocytes are resealed by adding 0.1 vol of, 100 mM inosine, 20 mM ATP, 4 mM $MgCl_2$, glucose anhydrous 100 mM, sodium pyruvate 100 mM, 190 mM NaCl, 1666 mM KCl and 33 mM $NaH_2PO_4$ (pH 7.4) per volume of dialysed erythrocyte solution (this solution is pre-measured and provided in a sterile ampoule). The dialysis bag in its bottle is placed in a small bath at 37° C., and the cells are incubated for 25 min.

The resealed cells are washed 4 times in the washing buffer (50 mL each time) and centrifuged each time for 10 min at 500 g; there is a cell recovery of about 40%. Typically about 32 mL of whole blood yields 16 mL of packed (70 Ht) ICG-loaded erythrocytes. This is done according to the same procedure shown in FIG. 10, B, and finally the processed ICG-loaded erythrocytes are injected into the provided sterile storage vial and stored at 4° C. until used for angiography on the subject from whom the cells were obtained.

Example 2

A Non-Dialysis Alternative to the Method in Example 1

ICG encapsulation in human erythrocytes by a procedure of hypotonic dialysis, isotonic resealing and re-annealing similar to the method described in Example 1 can be carried out without recourse to a dialysis step. This is done by decreasing the tonicity of the solution in which erythrocytes are suspended from 300 mOsm/kg to 87 mOsm/kg in four stages to open pores in the cells' membranes. These stages are all carried out in the same 50-mL centrifuge tube, at the completion of which ICG dye can be introduced to the cell suspension solution. As in Example 1, a kit consisting of various sterile containers and pre-measured fluids is utilised. In this case, the kit has different components than indicated in the one depicted in FIG. 9; this kit consists of:

1 10-mL vacutainer* containing an anti-coagulant (acid-citrate-dextrose)

(*Note: "vacutainer", as used throughout, refers to a variation of the sterilised rubber-stoppered evacuated test tube-like container commonly used for venipuncture. Each is constructed to withstand centrifugation, is sterilised, pre-filled with an appropriate fluid, and evacuated of air to form a vacuum.)

2 15-mL vacutainers, each containing 10 mL sterilised washing buffer
    1 50-mL vacutainer containing 4 mL of 198 mOsm/kg sterilised washing buffer
    1 vial containing 10 mL of 198 mOsm/kg sterilised washing buffer
    1 vial containing 20 mL of 99 mOsm/kg sterilised washing buffer
    1 vial containing 29.8 mg of lyophilised ICG dye
    1 syringe pre-loaded with 1.5 mL sterilised distilled $H_2O$ for reconstitution of the ICG
    1 vial containing 3.8 mL of sterilised resealing solution
    5 long (about 4 inch) sterile needles
    3 50-mL vacutainers, each containing 40 mL normotonic sterilised washing buffer
    1 5-mL rubber-stoppered, evacuated vial containing 1 mL of normotonic washing buffer Nine (9) mL of fresh blood, to which an anti-coagulant (acid-citrate-dextrose or ethylenediaminetetraacetic acid) is added, are obtained under sterile conditions and centrifuged at 2000 g for 5 min to obtain at least 4.0 mL of erythrocytes (see FIG. 10, A). Blood collection is done using a 10-mL vacutainer* pre-loaded with anti-coagulant. This same tube is then inserted into the centrifuge, and the blood is separated, with the erythrocytes at the bottom. Using one of the two supplied long needle connected to a syringe (see FIG. 9, H), the 4-mL erythrocyte sample is extracted from the bottom, so as to exclude any white cells in the overlying buffy coat and serum.

The erythrocytes are then washed twice in 10 mM HEPES (pH 7.4) containing 154 mM NaCl and 5 mM glucose (washing buffer) to remove leukocytes and platelets, centrifuging at 2000 g for 5 minutes each time. This is done by injecting the erythrocytes in the syringe, from the above step, into the first of two 15-mL vacutainer pre-loaded with 10 mL of washing solution and centrifuged, again at 2000 g for 4 min. Once the erythrocytes are again concentrated in the tube bottom, they are removed using one of the long needles and a syringe (see FIG. 10, B) and transferred to the second 15-mL vacutainer pre-loaded with washing solution, centrifugation is repeated and the concentrated erythrocytes again collected in a syringe.

Three (3) mL of the twice-washed erythrocytes are added to a 50-mL vacutainer containing 4 mL of 198 mOsm/kg washing buffer and gently agitated for 20 min.

The pre-measured 10 mL volume of 99 mOsm/kg washing buffer is added to a 50-mL vacutainer and gently agitated for an additional 20 min.

The pre-measured 20 mL volume of 49 mOsm/kg washing buffer is added to a 50-mL vacutainer and gently agitated for a final 20 min.; this will produce a mixture at about 87 mOsm/kg, causing pores in the erythrocytes to opened.

The pre-measured 1.5 mL volume of distilled $H_2O$ is added to the vial containing 29.8 mg vial of lyophilised ICG to reconstituted it, and the liquid dye is then added to the contents of the 50 mL vacutainer, resulting in a dye concentration of 1 μmol/mL. The 50-mL vacutainer is gently agitated in a 37° C. bath for 20 min.

The erythrocytes are resealed by adding the pre-measured 3.8 mL volume of, 100 mM inosine, 20 mM ATP, 4 mM $MgCl_2$, glucose anhydrous 100 mM, sodium pyruvate 100 mM, 190 mM NaCl, 1666 mM KCl and 33 mM $NaH_2PO_4$ (pH 7.4) to the solution in the 50-mL vacutainer to make the mixture normotonic; it is agitated and kept in the 37° C. bath for 20 min.

The 50-mL tube is centrifuged at 2000 g for 5 min, after which one of the supplied long needles and a syringe are used to remove the 3-mL volume of cells at the bottom of the tube and transfer them to a fresh 50-mL stoppered tube containing 40 mL of washing buffer. This tube is agitated and centrifuged at 2000 g for 4 min.

The procedure above is repeated twice more, after which 1-2 mL of the thrice-washed dye-loaded erythrocytes at the bottom of the tube are removed with the last of the long needles and a syringe and deposited in a sterile 5-mL rubber-stoppered, evacuated vial containing 1-2 mL of the normotonic washing buffer. These cells at about 50% Ht can be stored at 4° C. for up to several days prior to re-injection for angiography.

Example 3

An Alternative to the Non-Dialysis Method in Example 2

Encapsulation in erythrocyte ghost cells of a fluorescent dye, along with other substances, can be carried out using a kit of pre-loaded, sterilized tubes consisting of:

1 10-mL vacutainer* containing an anti-coagulant (acid-citrate-dextrose)
    1 15-mL vacutainer (empty)
    2 15-mL vacutainers each containing 11.5 mL of washing buffer
    1 15 mL vacutainer containing 2.0 mL of distilled $H_2O$
    1 vial containing 1 mL of distilled $H_2O$
    1 vial containing 29.8 mg of lyophilised ICG dye
1 syringe pre-loaded with 1.5 mL sterilised distilled $H_2O$ for reconstitution of the ICG 1 vial containing 260 µl of sterilised resealing solution
1 vial containing 50 mL of sterilised washing solution
   3 long (about 4 inch) sterile needles
   The method includes the steps of:
Acquire 8.5 mL blood in B-D Vacutainer containing ACD-solution A (294 mOsm/kg, pH 7.4)
The 8.5 mL sample is transferred to an empty 15 mL vacutainer and centrifuged at 2,000 g for 10 min.
Gently push the first long needle through the rubber stopper, supernate, and the packed cell layer; remove 3.5 mL of packed cells from bottom of tube.
Place the 3.5 mL of cells in a 15 mL vacutainer containing 11.5 mL of washing solution (300 mOsm/kg, pH 7.4), and centrifuge at 2,000 g for 10 min.
Gently push the second long needle through the rubber stopper, supernate, and the packed cell layer; remove 3.5 mL of packed cells from bottom of tube and introduced into new 15 mL vacutainer containing 2.0 mL of distilled, deionized $H_2O$ to cells, while agitating the tube and let cells sit for 15 minutes at room temperature; this produces 150 mOsm/kg.
Add an additional 1.0 mL of distilled, deionized $H_2O$, while agitating the tube, and let cells sit for 15 minutes more at room temperature; this produces 125 mOsm/kg.
Add 186 µl of ICG (25 mg/mL concentration), while agitating the tube, and let conjugate for 30 minutes at room temperature; then incubate for 5 minutes at 37° C. bath.
Add 260 µl of resealing solution, while agitating the tube; this produces 300 mOsm/kg. Keep tube in 37° C. bath for 15 minutes.
Fill tube to top by adding 9 mL of 300 mOsm/kg washing solution. Centrifuge at 500 g for 10 minutes.
Remove supernate, leaving packed cells at bottom of tube. Refill tube with 300 mOsm/kg washing solution and centrifuge at 500 g for 10 minutes.
Repeat above step 3 more times. At the end of this 4th wash, the supernate is clear, and 0.5 mL of packed, ICG-loaded cells are recovered from the bottom of the tube, using the third long needle;
If the cells are not injected immediately, they are diluted by addition of about 8.0 mL of 300 mOsm/kg washing solution and stored at 4° C. for up to 24 hours.

Example 4

Another Alternative to the Non-Dialysis Method in Example 2

Encapsulation in erythrocyte ghost cells of a fluorescent dye, along with other substances, can be carried out using a kit of pre-loaded, sterilized tubes consisting of:
1 10-mL vacutainer* containing an anti-coagulant (acid-citrate-dextrose)
  2 50-mL vacutainers, each containing 46.5 mL sterilised washing buffer
1 50-mL vacutainer containing 48 mL of sterilised washing buffer
   1 vial containing 260 µl of resealing solution
1 vial containing 3 mL of sterilised distilled, deionized $H_2O$
   1 vial containing 43.5 mL of sterilised washing buffer
   1 vial containing 29.8 mg of lyophilised ICG dye
1 syringe pre-loaded with 1.5 mL sterilised distilled, deionized $H_2O$ for reconstitution of the ICG
   4 long (about 4 inch) sterile needles
   The method includes the steps of:
8.5 mL of freshly-drawn blood are collected in a vacuum tube containing 0.5 mL of acid-citrate-dextrose anticoagulant and gently shaken. Then the tube is and centrifuged at 500 g for 10 min.

A first 4-in needle is pushed through the rubber stopper of the tube, through the plasma supernatant and buffy coat layers, and to the bottom of the packed cell layer. 3.5 mL of packed cells are then withdrawn from the bottom of tube and transferred to a first rubber-stoppered 50-mL tube containing 46.5 mL of 300 mOsm/kg, 7.4-pH washing buffer. The tube is gently shaken and then centrifuged at 500 g for 10 minutes.
A second 4-in needle is pushed through the stopper and through to the bottom of the packed cell layer, and 3.0 mL of packed cells are withdrawn from the bottom of the tube and place in the second rubber-stoppered 50-mL tube, containing 2.0 mL of 7.4-pH distilled, deionized $H_2O$. The tube is gently agitated, and then let stand for 15 minutes; the mixture will be about 150 mOsm/kg.
An additional 1.0 mL of 7.4-pH distilled, deionized $H_2O$, while agitating the tube, and let cells sit for 15 minutes more; the mixture will be about 125 mOsm/kg.
186 µL of 25 mg/mL concentration ICG dye are added to the tube, while agitating it. At this time, additional substances to be encapsulated in the erythrocyte ghost cells also can be added in small-volumes of high-concentrations to the tube. The tube is gently agitated, and let stand with occasional gentle agitation for 30 minutes at room temperature; then incubated for 5 minutes in a 37° C. bath.
260 µL of 7.4-pH, 3590 mOsm/kg cell resealing solution is then added to the tube, which is then gently agitated; this produces 300 mOsm/kg. The tube is kept in the 37° C. bath for 15 minutes.
Add 43.5 mL of 7.4-ph 300 mOsm/kg washing solution to the tube. The tube is shaken and centrifuged at 500 g for 10 minutes.
A third 4-in needle is pushed through the rubber stopper of the tube and to the bottom. 2.0 mL are withdrawn from the bottom of the tube and injected into a third 50-mL tube, which contains 48 mL of 7.4-ph 300 mOsm/kg washing solution. The tube is shaken and centrifuged at 500 g for 10 minutes.
A fourth 4-in needle is pushed through the stopper of the tube and to the bottom. 1.5 mL of packed cells are withdrawn from the bottom of the tube; these are ready for immediate injection.
If the cells are not injected immediately, they are diluted by addition of about 8.0 mL of 7.4-pH 300 mOsm/kg washing solution and stored at 4° C. for up to 24 hours.

REFERENCES

1. DeLoach R. Encapsulation of exogenous agents in erythrocytes and the circulating survival of carrier erythrocytes. J Appl Biochem. 1983; 5:149-57.
2. De Loach J R Sprandel U: Red blood cells as carriers for drugs. Basel Karger 1985; De Flora A PNAS 1986; 83:7029.
3. Ropars C, Chassaigne M, Nicolau C, Red Blood Cells as carriers for drugs. Potential therapeutic applications. Oxford, Pergamon Press, 1987.
4. Rossi L, Brandi G, Schiavano G F, Scarfi S, Millo E, Damonte G, Benatti U, De Flora A, Magnani M. Heterodimer-loaded RBCs as bioreactors for slow delivery of the antiviral drug azidothymidine and the antimycobacterial drug ethambutol. AIDS Res Hum Retrovir 1999; 15:345-353.
5. Rossi L, Serafini S, Cenerini L, Picardi F, Bigi L, Panzani I, Magnani M. RBC-mediated delivery of dexamethasone in patients with chronic obstructive pulmonary disease. Biotechnol Appl Biochem. 2001; 33:85-89.

6. Rossi L, Castro M, D'Orio F, Damonte G, Serafini S, Bigi L, Panzani I, Novelli G, Dallapiccola B, Panunzi S, Di Carlo P, Bella S, Magnani M. Low doses of dexamethasone constantly delivered by autologous RBCs slow the progression of lung disease in cystic fibrosis patients. Blood Cells Mol Dis. 2004; 33:57-63.
7. Annese V, Latiano A, Rossi L, Lombardi G, Dallapiccola B, Serafini S, Damonte G, Andriulli A, Magnani M. RBCs-mediated delivery of dexamethasone in steroid-dependent IBD patients-a pilot uncontrolled study. Am J Gastroenterol. 2005; 100:1370-1375.
8. Flower R W. Optimizing treatment of choroidal neovascularization feeder vessels associated with age-related macular degeneration. Am J. Ophthalmol. 2002; 134:228-239.
9. Flower R, Peiretti E, Magnani M, Rossi L, Serafini S, Gryczynski Z, Gryczynski I., Observation of erythrocyte dynamics in the retinal capillaries and choriocapillaris using ICG-loaded erythrocyte ghost cells. Invest. Ophthalmol. Vis. Sci. 2008; 49: 5510-5516.
10. Bek T. Diabetic maculopathy caused by disturbances in retinal vasomotion: a new hypothesis. Acta Ophthalmol Scand. 1999; 77:376-380.
11. Geddes C D, Haishi C, Gryczynski I, Gryczynski Z, Jiyu F, Lakowicz J R. Metal-Enhanced Fluorescence (MEF) Due to Silver Colloids on a Planar Surface: Potential Applications of Indocyanine Green to in Vivo Imaging. J Phys. Chem. A. 2003: 107:3443-3449.
12. "Erythrocyte Movement in the Capillaries", Macula 2009, New York, N.Y., Jan. 16-17, 2009. (Clinical lecture)
13. "Monitoring Erythrocyte Movement in Rhesus Monkey and Human Retinal Capillaries" 2009 RD Richards Lecture in Ophthalmology and Research Forum, Baltimore, Md., Feb. 27, 2009. (Clinical lecture)

The invention claimed is:

1. A method of making a freeze-dried composition of erythrocytes comprising indocyanine green (ICG), the method comprising:
   (a) providing erythrocytes in a blood anti-coagulant solution to form an erythrocyte-containing solution;
   (b) reducing the osmolality of the erythrocyte-containing solution from step (a) by adding distilled, de-ionized water directly to the erythrocyte-containing solution to reduce the osmolality of the erythrocyte-containing solution to 100-125 mOsm/kg to form a hypotonic solution to cause pores in the erythrocytes to open;
   (c) before performing step (d), combining the hypotonic solution from step (b) with ICG and an at least 50 mM saccharide solution comprising a first saccharide to form an ICG-containing solution;
   (d) combining the ICG-containing solution from step (c) with a resealing solution having an osmolality of at least 1000 mOsm/kg to increase the osmolality of the ICG-containing solution, thereby causing the pores in the erythrocytes to close and entrap the ICG and the first saccharide within the erythrocytes;
   (e) washing the erythrocytes from step (d) in an isotonic saline washing solution comprising a second saccharide to remove extracellular ICG; and
   (f) freeze-drying the washed erythrocytes containing the entrapped ICG from step (e).

2. The method of claim 1, wherein the first saccharide is selected from the group consisting of mannose, xylose, glucose, trehalose, sucrose, and maltose.

3. The method of claim 1, wherein the step of providing erythrocytes comprises obtaining a blood sample from a subject.

4. The method of claim 1, further comprising washing the erythrocytes with an isotonic solution prior to adding the distilled, de-ionized water in step (b).

5. The method of claim 1, wherein a concentration of the ICG entrapped in step (d) ranges from 0.25 to 1.5 mM.

6. The method of claim 1, wherein a concentration of the ICG entrapped in step (d) ranges from 0.3 to 0.4 mM.

7. The method of claim 1, wherein a concentration of the ICG entrapped in step (d) is greater than 0.4 mM.

8. The method of claim 1, wherein the ICG has a concentration ranging from 0.25 to 3.0 μmol/mL of hypotonic solution.

9. The method of claim 1, further comprising adding at least one therapeutically effective agent prior to step (d) to entrap the at least one agent within the erythrocytes.

10. The method of claim 1, wherein the resealing solution has an osmolality of at least 2000 mOsm/kg.

11. The method of claim 1, wherein a source of the erythrocytes in step (a) is O-type blood.

12. The method of claim 1, wherein a source of the erythrocytes in step (a) is A-type or B-type blood.

13. The method of claim 1, wherein after step (a), the method further comprises adding α- and β-glucosidase to split off the erythrocyte surface A- and B-agglutinogens, respectively.

14. The method of claim 1, wherein the erythrocytes in step (d) entrap a substance that inhibits a destructive formation of ice crystals during cooling.

15. The method of claim 14, wherein the substance is the first saccharide.

16. The method of claim 15, wherein the first saccharide is trehalose.

17. The method of claim 15, wherein the first saccharide is a monosaccharide.

* * * * *